US012753237B2

(12) United States Patent
Katagiri et al.

(10) Patent No.: US 12,753,237 B2

(45) Date of Patent: Oct. 6, 2026

(54) ANTIBODY RECOGNIZING EXTRACELLULAR REGION OF ALK2/ACVR1

(71) Applicant: Saitama Medical University, Iruma-gun (JP)

(72) Inventors: Takenobu Katagiri, Saitama (JP); Sho Tsukamoto, Saitama (JP); Mai Kuratani, Saitama (JP)

(73) Assignee: Saitama Medical University, Saitama (JP)

( * ) Notice: Subject to any disclaimer, the term of this patent is extended or adjusted under 35 U.S.C. 154(b) by 1293 days.

(21) Appl. No.: 17/629,715

(22) PCT Filed: Jul. 22, 2020

(86) PCT No.: PCT/JP2020/028465

§ 371 (c)(1),
(2) Date: Jan. 24, 2022

(87) PCT Pub. No.: WO2021/020282

PCT Pub. Date: Feb. 4, 2021

(65) Prior Publication Data

US 2022/0267453 A1 Aug. 25, 2022

(30) Foreign Application Priority Data

Jul. 26, 2019 (JP) ................................ 2019-138312

(51) Int. Cl.
*C07K 16/28* (2006.01)

(52) U.S. Cl.
CPC ...... *C07K 16/2863* (2013.01); *C07K 2317/33* (2013.01); *C07K 2317/565* (2013.01); *C07K 2317/76* (2013.01)

(58) Field of Classification Search
CPC ............ C07K 16/2863; C07K 2317/33; C07K 2317/565; C07K 2317/76; C07K 2317/56; C07K 16/2896; A61K 2039/505; A61P 19/08; A61P 25/00; A61P 35/00
See application file for complete search history.

(56) References Cited

U.S. PATENT DOCUMENTS

2018/0118835 A1* 5/2018 Katagiri et al. . A61K 2039/505

FOREIGN PATENT DOCUMENTS

WO WO-2016/121908 A1 8/2016

OTHER PUBLICATIONS

Funaba et al., "Immunolocalization of Type I or Type II Activin Receptors in the Rat Brain," Journal of Neuroendocrinology, 1997, 9:105-111.

Katagiri et al. "Heterotopic Bone Formation Induced by Bone Morphogenetic Protein Signaling: Fibrodysplasia Ossificans Progressiva," J. Oral Biosci., 2010, 52(1):33-41.

Katagiri et al., "Identification of Amino Acid Residues of ALK2 Extracellular Region Important for Activity of Binding and Inhibition of Anti-ALK2 Inhibitory Antibody," Programs and Abstracts of the Annual Meeting of the Japanese Society for Bone and Mineral Research, 2019, 37:216, O-136, with English translation.

Katagiri et al., "Recent topics in fibrodysplasia ossificans progressiva," Journal of Oral Biosciences, Aug. 17, 2012, 54:119-123.

Katagiri et al., "The unique activity of bone morphogenetic proteins in bone: a critical role of the Smad signaling pathway," Biol. Chem., 2013, 394(6):703-714.

Shore et al., "A recurrent mutation in the BMP type I receptor ACVR1 causes inherited and sporadic fibrodysplasia ossificans progressiva," Nature Genetics, May 2006, 38(5):525-527.

International Search Report dated Sep. 29, 2020 in PCT/JP2020/028465.

Fujimoto et al., "Establishment of a novel model of chondrogenesis using murine embryonic stem cells carrying fibrodysplasia ossificans progressiva-associated mutant ALK2," Biochemical and Biophysical Research Communications, Nov. 15, 2014, 455(3):347-352.

Lin et al., "AMPK downregulates ALK2 via increasing the interaction between Smurf1 and Smad6, leading to inhibition of osteogenic differentiation," BBA-Molecular Cell Research, Aug. 25, 2017, 1864(12):2369-2377.

Supplementary Partial European Search Report dated May 15, 2023 in EP 20848302.4.

* cited by examiner

*Primary Examiner* — Thomas J. Visone

(74) *Attorney, Agent, or Firm* — Foley & Lardner LLP

(57) ABSTRACT

This application provides: an antibody or an antigen-binding fragment thereof which can be used not only as a therapeutic drug but as a tool of immunological and immunohistological analysis such as immunostaining or Western blot, specifically recognizes an extracellular region polypeptide of human, mouse and rat ALK2, and inhibits BMP signal transduction, and an antibody or an antigen-binding fragment thereof which has a property of specifically binding to an extracellular region of ALK2 to form an ALK2 homodimer and a property of inhibiting the formation of an ALK2-type II receptor heterodimer, and inhibits the activation of ALK2 kinase, or inhibits BMP signal transduction; and a method for inhibiting the activation of ALK2 kinase or a method for inhibiting BMP signal transduction using the antibody or the antigen-binding fragment thereof.

12 Claims, 8 Drawing Sheets

Specification includes a Sequence Listing.

ANTIBODY RECOGNIZING EXTRACELLULAR REGION OF ALK2/ACVR1

CROSS-REFERENCE TO RELATED APPLICATIONS

This application is the U.S. National Stage of PCT/JP2020/028465, filed Jul. 22, 2020, which claims priority to JP 2019-138312, filed Jul. 26, 2019.

The instant application contains a Sequence Listing which has been submitted in ASCII format via EFS-WEB and is hereby incorporated by reference in its entirety. Said ASCII copy, created on Jan. 21, 2022, is named sequence.txt and is 51,969 bytes.

TECHNICAL FIELD

The present invention relates to an antibody that recognizes an extracellular region of ALK2/ACVR1 (hereinafter, referred to as "ALK2" unless otherwise specified). Specifically, the present invention relates to an antibody that further inhibits ALK2 kinase activity, or an antibody that further inhibits BMP signal transduction.

The present invention also relates to a method for inhibiting ALK2 kinase activity or a method for inhibiting BMP signal transduction, in a cell expressing ALK2, using the above-described antibody.

BACKGROUND ART

ALK2 is an abbreviation of activin like kinase 2. This protein is also called activin A type I receptor 1 (ACVR1) and is a receptor of bone morphogenetic protein (BMP).

Human or mouse ALK2 is a single-pass transmembrane protein consisting of 509 amino acids and having a signal peptide and functions as a transmembrane type of serine-threonine kinase receptor binding to BMPs (Non Patent Literatures 1 to 3). ALK2 binds to BMPs at its N-terminal extracellular region and activates the downstream intracellular signal transduction system through an intracellular serine-threonine kinase.

Activated ALK2 having an amino acid substitution has been found from cases of familial and sporadic FOP (fibrodysplasia ossificans progressiva), a genetic disease which causes cartilage tissues or bone tissues to be ectopically formed, and its gene has received attention as a responsible gene for FOP (Non Patent Literature 4).

As for an antibody that specifically binds to ALK2 and inhibits BMP signal transduction, for example, Patent Literature 1 discloses anti-ALK2 antibodies and use thereof in the treatment of ectopic ossification and/or bone dysplasia.

CITATION LIST

Patent Literature

Patent Literature 1: International Publication No. WO2016/121908

Non Patent Literature

Non Patent Literature 1: T. Katagiri, J. Oral Biosci., 52, 33-41 (2010)

Non Patent Literature 2: T. Katagiri, J. Oral Biosci., 54, 119-123 (2012)

Non Patent Literature 3: T. Katagiri and S. Tsukamoto, Biol. Chem., 394, 703-714 (2013)

Non Patent Literature 4: E. M. Shore et al., Nat. Genet., 38, 525-527 (2006)

SUMMARY OF INVENTION

Technical Problem

The present inventors have previously developed anti-ALK2 antibodies. It has been found that these antibodies recognize human or mouse ALK2 and inhibit ligand-dependent intracellular signals in a dose-dependent manner, but cannot recognize ALK2 in immunohistological analysis using tissue sections or Western blot analysis using reduced denatured ALK2.

Thus, an object of the present invention is to provide an anti-ALK2 antibody that is useful not only as a therapeutic drug but as a tool of immunological and immunohistological analysis.

Solution to Problem

In order to attain the object, many clones producing rat monoclonal antibodies against human ALK2 were prepared, and anti-ALK2 antibodies useful as tools of immunological and immunohistological analysis were found from among them. These antibodies also include antibodies that recognized human, mouse and rat ALK2. Such antibodies were also found this time to bring about incomplete or loose conformational change in BMP receptor (tetramer composed of ALK2 and type II receptor) and thereby inhibit the interaction between ALK2/ACVR1 (type I receptor) and type II receptor, thereby exerting an inhibitory effect on receptor activation.

Thus, the present invention encompasses the following features.

[1] An antibody or an antigen-binding fragment thereof which specifically recognizes polypeptides consisting of the following amino acid sequences (a) to (c) and inhibits BMP signal transduction:

(a) an amino acid sequence consisting of amino acid numbers 21 to 123 of the amino acid sequence of SEQ ID NO: 1;

(b) an amino acid sequence consisting of amino acid numbers 21 to 123 of the amino acid sequence of SEQ ID NO: 2; and (c) an amino acid sequence consisting of amino acid numbers 21 to 123 of the amino acid sequence of SEQ ID NO: 3.

[2] The antibody or the antigen-binding fragment thereof according to [1], wherein the antibody or the antigen-binding fragment thereof binds to an epitope comprising arginine at amino acid number 64 in the amino acid sequence of SEQ ID NO: 3.

[3] The antibody or the antigen-binding fragment thereof according to [1] or [2], wherein the heavy chain sequence comprises a variable region comprising CDR sequences consisting of the amino acid sequences of SEQ ID NO: 13 (CDRH1), SEQ ID NO: 14 (CDRH2) and SEQ ID NO: 15 (CDRH3), and the light chain sequence comprises a variable region comprising CDR sequences consisting of the amino acid sequences of SEQ ID NO: 16 (CDRL1), SEQ ID NO: 17 (CDRL2) and SEQ ID NO: 18 (CDRL3).

[4] The antibody or the antigen-binding fragment thereof according to [3], wherein the antibody comprises a heavy chain variable region sequence consisting of the amino acid sequence of SEQ ID NO: 9 and a light chain variable region sequence consisting of the amino acid sequence of SEQ ID NO: 11.

[5] The antibody or the antigen-binding fragment thereof according to [1] or [2], wherein the antibody or the antigen-binding fragment thereof cross-competes, for binding to an extracellular region of ALK2 protein, with an antibody or an antigen-binding fragment thereof according to [3] or [4].

[6] The antibody or the antigen-binding fragment thereof according to any of [1] to [5], wherein the antibody or the antigen-binding fragment thereof is a monoclonal antibody, a polyclonal antibody, a rat antibody, a chimeric antibody, a humanized antibody, a human antibody, a diabody, a multispecific antibody, Fab, $F(ab)_2$, Fab', Fv, or scFv.

[7] The antibody or the antigen-binding fragment thereof according to any of [1] to [5], wherein an isotype of the heavy chain constant region is IgG2b.

[8] A pharmaceutical composition comprising at least any one antibody or antigen-binding fragment thereof according to any of [1] to [7].

[9] The pharmaceutical composition according to [8], wherein the pharmaceutical composition is a therapeutic and/or prophylactic drug for ectopic ossification and/or diffuse intrinsic pontine glioma (DIPG).

[10] The pharmaceutical composition according to [9], wherein the ectopic ossification is fibrodysplasia ossificans progressiva (FOP).

[11] An antibody or an antigen-binding fragment thereof having binding activity to ALK2 protein, where the antibody or the fragment is: an antibody or an antigen-binding fragment thereof in which the heavy chain sequence comprises a variable region comprising CDR sequences consisting of the amino acid sequences of SEQ ID NO: 13 (CDRH1), SEQ ID NO: 14 (CDRH2) and SEQ ID NO: 15 (CDRH3), and the light chain sequence comprises a variable region comprising CDR sequences consisting of the amino acid sequences of SEQ ID NO: 16 (CDRL1), SEQ ID NO: 17 (CDRL2) and SEQ ID NO: 18 (CDRL3); or an antibody or an antigen-binding fragment thereof which cross-competes, for binding to the ALK2 protein, with the antibody or the antigen-binding fragment.

[12] An antibody or an antigen-binding fragment thereof having binding activity to ALK2 protein, where the antibody or the fragment is: an antibody or an antigen-binding fragment thereof in which the heavy chain sequence comprises a variable region comprising CDR sequences consisting of the amino acid sequences of SEQ ID NO: 23 (CDRH1), SEQ ID NO: 24 (CDRH2) and SEQ ID NO: 25 (CDRH3), and the light chain sequence comprises a variable region comprising CDR sequences consisting of the amino acid sequences of SEQ ID NO: 26 (CDRL1), SEQ ID NO: 27 (CDRL2) and SEQ ID NO: 28 (CDRL3); or an antibody or an antigen-binding fragment thereof which cross-competes, for binding to the ALK2 protein, with the antibody or the antigen-binding fragment.

[13] An antibody consisting of a heavy chain comprising a heavy chain variable region sequence consisting of the amino acid sequence of SEQ ID NO: 9 and a light chain comprising a light chain variable region sequence consisting of the amino acid sequence of SEQ ID NO: 11, or an antigen-binding fragment thereof, or an antibody or an antigen-binding fragment thereof which cross-competes, for binding to ALK2 protein, with the antibody or the antigen-binding fragment.

[14] An antibody consisting of a heavy chain comprising a heavy chain variable region sequence consisting of the amino acid sequence of SEQ ID NO: 19 and a light chain comprising a light chain variable region sequence consisting of the amino acid sequence of SEQ ID NO: 21, or an antigen-binding fragment thereof, or an antibody or an antigen-binding fragment thereof which cross-competes, for binding to ALK2 protein, with the antibody or the antigen-binding fragment.

[15] Use of an antibody or an antigen-binding fragment thereof according to any of [1] to [7], [11], and [13] in immunostaining.

[16] The use according to [15], wherein the immunostaining employs a frozen section or a paraffin section of a tissue.

[17] Use of an antibody or an antigen-binding fragment thereof according to [12] or [14] in immunostaining or Western blotting.

[18] Use of an antibody or an antigen-binding fragment thereof according to any of [1] to [7], [11], and [13] as a therapeutic and/or prophylactic drug for ectopic ossification and/or diffuse intrinsic pontine glioma (DIPG).

[19] Use of an antibody or an antigen-binding fragment thereof according to any of [1] to [7], [11], and [13] as a phosphorylation inhibitor for SMAD1, SMAD5 and/or SMAD8.

[20] A polynucleotide encoding an antibody or an antigen-binding fragment thereof according to any of [1] to [7] and [11] to [14].

[21] A vector comprising a polynucleotide according to [20].

[22] A method for inhibiting the activation of ALK2 kinase, comprising inhibiting the activation of the ALK2 kinase by allowing an antibody to act on a cell expressing ALK2 protein on cell surface, the antibody having a property of specifically binding to an extracellular region of ALK2 to form an ALK2 homodimer, and a property of inhibiting the formation of an ALK2-type II receptor heterodimer.

[23] A method for inhibiting BMP signal transduction, comprising inhibiting the BMP signal transduction by allowing an antibody to act on a cell expressing ALK2 protein on cell surface, the antibody having a property of specifically binding to an extracellular region of ALK2 to form an ALK2 homodimer, and a property of inhibiting the formation of an ALK2-type II receptor heterodimer.

[24] The method according to [22] or [23], wherein the amino acid residue at amino acid number 330 of ALK2 is proline.

[25] The method according to [22] or [23], wherein ALK2 has an activating mutation.

[26] The method according to [25], wherein the activating mutation in ALK2 is at least one selected from L196P, delP197_F198insL, R2021, R206H, Q207E, R258S, R258G, G325A, G328E, G328R, G328W, G356D, R375P, and K400E.

[27] The method according to [25], wherein the activating mutation in ALK2 is R206H mutation.

[28] The method according to any of [22] to [27], wherein the antibody is a monoclonal antibody or an antigen-binding fragment thereof.

[29] The method according to any of [22] to [28], wherein the monoclonal antibody or the antigen-binding fragment thereof is at least one antibody or antigen-binding fragment thereof indicated in the following (1) to (5):

(1) an antibody comprising a heavy chain variable region comprising CDRs consisting of the amino acid sequences of SEQ ID NO: 13 (CDRH1), SEQ ID NO: 14 (CDRH2) and SEQ ID NO: 15 (CDRH3), and a light chain variable region comprising CDRs consisting of the amino acid sequences of SEQ ID NO: 16 (CDRL1), SEQ ID NO: 17 (CDRL2) and SEQ ID NO: 18 (CDRL3), or an antigen-binding fragment thereof, or an antibody or an antigen-binding fragment thereof which cross-competes, for binding to an extracellular region of ALK2 protein, with the antibody or the antigen-binding fragment thereof;

(2) an antibody comprising a heavy chain variable region comprising CDRs consisting of the amino acid sequences of SEQ ID NO: 29 (CDRH1), SEQ ID NO: 30 (CDRH2) and SEQ ID NO: 31 (CDRH3), and a light chain variable region comprising CDRs consisting of the amino acid sequences of SEQ ID NO: 32 (CDRL1), SEQ ID NO: 33 (CDRL2) and SEQ ID NO: 34 (CDRL3), or an antigen-binding fragment thereof, or an antibody or an antigen-binding fragment thereof which cross-competes, for binding to an extracellular region of ALK2 protein, with the antibody or the antigen-binding fragment thereof;

(3) an antibody comprising a heavy chain variable region comprising CDRs consisting of the amino acid sequences of SEQ ID NO: 35 (CDRH1), SEQ ID NO: 36 (CDRH2) and SEQ ID NO: 37 (CDRH3), and a light chain variable region comprising CDRs consisting of the amino acid sequences of SEQ ID NO: 38 (CDRL1), SEQ ID NO: 39 (CDRL2) and SEQ ID NO: 40 (CDRL3), or an antigen-binding fragment thereof, or an antibody or an antigen-binding fragment thereof which cross-competes, for binding to an extracellular region of ALK2 protein, with the antibody or the antigen-binding fragment thereof;

(4) an antibody comprising a heavy chain variable region comprising CDRs consisting of the amino acid sequences of SEQ ID NO: 41 (CDRH1), SEQ ID NO: 42 (CDRH2) and SEQ ID NO: 43 (CDRH3), and a light chain variable region comprising CDRs consisting of the amino acid sequences of SEQ ID NO: 44 (CDRL1), SEQ ID NO: 45 (CDRL2) and SEQ ID NO: 46 (CDRL3), or an antigen-binding fragment thereof, or an antibody or an antigen-binding fragment thereof which cross-competes, for binding to an extracellular region of ALK2 protein, with the antibody or the antigen-binding fragment thereof; and (5) an antibody comprising a heavy chain variable region comprising CDRs consisting of the amino acid sequences of SEQ ID NO: 47 (CDRH1), SEQ ID NO: 48 (CDRH2) and SEQ ID NO: 49 (CDRH3), and a light chain variable region comprising CDRs consisting of the amino acid sequences of SEQ ID NO: 50 (CDRL1), SEQ ID NO: 51 (CDRL2) and SEQ ID NO: 52 (CDRL3), or an antigen-binding fragment thereof, or an antibody or an antigen-binding fragment thereof which cross-competes, for binding to an extracellular region of ALK2 protein, with the antibody or the antigen-binding fragment thereof.

Alternatively, the present invention has the following features.

[1'] An antibody or an antigen-binding fragment thereof which specifically recognizes polypeptides consisting of the following amino acid sequences (a) to (c) and inhibits BMP signal transduction:

(a) an amino acid sequence consisting of amino acid numbers 21 to 123 of the amino acid sequence of SEQ ID NO: 1;

(b) an amino acid sequence consisting of amino acid numbers 21 to 123 of the amino acid sequence of SEQ ID NO: 2; and (c) an amino acid sequence consisting of amino acid numbers 21 to 123 of the amino acid sequence of SEQ ID NO: 3.

[2'] The antibody or the antigen-binding fragment thereof according to [1'], wherein the antibody or the antigen-binding fragment thereof binds to an epitope comprising arginine at amino acid number 64 in the amino acid sequence of SEQ ID NO: 3.

[3'] The antibody or the antigen-binding fragment thereof according to [1'] or [2'], wherein the heavy chain sequence comprises a variable region comprising CDR sequences consisting of the amino acid sequences of SEQ ID NO: 13 (CDRH1), SEQ ID NO: 14 (CDRH2) and SEQ ID NO: 15 (CDRH3), and the light chain sequence comprises a variable region comprising CDR sequences consisting of the amino acid sequences of SEQ ID NO: 16 (CDRL1), SEQ ID NO: 17 (CDRL2) and SEQ ID NO: 18 (CDRL3).

[4'] The antibody or the antigen-binding fragment thereof according to [3'], wherein the antibody comprises a heavy chain variable region sequence consisting of the amino acid sequence of SEQ ID NO: 9 and a light chain variable region sequence consisting of the amino acid sequence of SEQ ID NO: 11.

[5'] The antibody or the antigen-binding fragment thereof according to [1'] or [2'], wherein the antibody or the antigen-binding fragment thereof cross-competes, for binding to an extracellular region of ALK2 protein, with an antibody or an antigen-binding fragment thereof according to [3'] or [4'].

[6'] The antibody or the antigen-binding fragment thereof according to any of [1'] to [5'], wherein the antibody or the antigen-binding fragment thereof is a monoclonal antibody, a polyclonal antibody, a rat antibody, a chimeric antibody, a humanized antibody, a human antibody, a diabody, a multispecific antibody, Fab, $F(ab)_2$, Fab', Fv, or scFv.

[7'] The antibody or the antigen-binding fragment thereof according to any of [1'] to [5'], wherein an isotype of the heavy chain constant region is IgG2b.

[8'] A pharmaceutical composition comprising at least any one antibody or antigen-binding fragment thereof according to any of [1'] to [7'].

[9'] The pharmaceutical composition according to [8'], wherein the pharmaceutical composition is a therapeutic and/or prophylactic drug for ectopic ossification and/or diffuse intrinsic pontine glioma (DIPG).

[10'] The pharmaceutical composition according to [9'], wherein the ectopic ossification is fibrodysplasia ossificans progressiva (FOP).

[11'] An antibody or an antigen-binding fragment thereof having binding activity to ALK2 protein, where the antibody or the fragment is: an antibody or an antigen-binding fragment thereof in which the heavy chain sequence comprises a variable region comprising CDR sequences consisting of the amino acid sequences of SEQ ID NO: 13 (CDRH1), SEQ ID NO: 14 (CDRH2) and SEQ ID NO: 15 (CDRH3), and the light chain sequence comprises a variable region comprising CDR sequences consisting of the amino acid sequences of SEQ ID NO: 16 (CDRL1), SEQ ID NO: 17 (CDRL2) and SEQ ID NO: 18 (CDRL3); or an antibody or an antigen-binding fragment thereof which cross-competes, for binding to the ALK2 protein, with the antibody or the antigen-binding fragment.

[12'] An antibody or an antigen-binding fragment thereof having binding activity to ALK2 protein, where the antibody or the fragment is: an antibody or an antigen-binding fragment thereof in which the heavy chain sequence comprises a variable region comprising CDR sequences consisting of the amino acid sequences of SEQ ID NO: 23 (CDRH1), SEQ ID NO: 24 (CDRH2) and SEQ ID NO: 25 (CDRH3), and the light chain sequence comprises a variable region comprising CDR sequences consisting of the amino acid sequences of SEQ ID NO: 26 (CDRL1), SEQ ID NO: 27 (CDRL2) and SEQ ID NO: 28 (CDRL3); or an antibody or an antigen-binding fragment thereof which cross-competes, for binding to the ALK2 protein, with the antibody or the antigen-binding fragment.

[13'] An antibody consisting of a heavy chain comprising a heavy chain variable region sequence consisting of the amino acid sequence of SEQ ID NO: 9 and a light chain comprising a light chain variable region sequence consisting of the amino acid sequence of SEQ ID NO: 11, or an antigen-binding fragment thereof, or an antibody or an antigen-binding fragment thereof which cross-competes, for binding to ALK2 protein, with the antibody or the antigen-binding fragment.

[14'] An antibody consisting of a heavy chain comprising a heavy chain variable region sequence consisting of the amino acid sequence of SEQ ID NO: 19 and a light chain comprising a light chain variable region sequence consisting of the amino acid sequence of SEQ ID NO: 21, or an antigen-binding fragment thereof, or an antibody or an antigen-binding fragment thereof which cross-competes, for binding to ALK2 protein, with the antibody or the antigen-binding fragment.

[15'] Use of an antibody or an antigen-binding fragment thereof according to any of [1'] to [7'], [1'], and [13'] in immunostaining.

[16'] Use of an antibody or an antigen-binding fragment thereof according to [12'] or [14'] in immunostaining or Western blotting.

[17'] The use according to [15'] or [16'], wherein the immunostaining employs a frozen section or a paraffin section of a tissue.

[18'] Use of an antibody or an antigen-binding fragment thereof according to any of [1'] to [7'], [11'], and [13'] as a therapeutic and/or prophylactic drug for ectopic ossification and/or diffuse intrinsic pontine glioma (DIPG).

[19'] Use of an antibody or an antigen-binding fragment thereof according to any of [1'] to [7'], [11'], and [13'] as a phosphorylation inhibitor for SMAD1, SMAD5 and/or SMAD8.

[20'] A polynucleotide encoding an antibody or an antigen-binding fragment thereof according to any of [1'] to [7'] and [11'] to [14'].

[21'] A vector comprising a polynucleotide according to [20'].

[22'] A method for inhibiting the activation of ALK2 kinase, comprising inhibiting the activation of the ALK2 kinase by allowing an antibody to act on a cell expressing ALK2 protein on cell surface, the antibody having a property of specifically binding to an extracellular region of ALK2 to form an ALK2 homodimer, and a property of inhibiting the formation of an ALK2-type II receptor heterodimer.

[23'] A method for inhibiting BMP signal transduction, comprising inhibiting the BMP signal transduction by allowing an antibody to act on a cell expressing ALK2 protein on cell surface, the antibody having a property of specifically binding to an extracellular region of ALK2 to form an ALK2 homodimer, and a property of inhibiting the formation of an ALK2-type II receptor heterodimer.

[24'] The method according to [22'] or [23'], wherein the amino acid residue at amino acid number 330 of ALK2 is proline.

[25'] The method according to [22'] or [23'], wherein ALK2 has an activating mutation.

[26'] The method according to [25'], wherein the activating mutation in ALK2 is at least one selected from L196P, delP197_F198insL, R2021, R206H, Q207E, R258S, R258G, G325A, G328E, G328R, G328W, G356D, R375P, and K400E.

[27'] The method according to [25'], wherein the activating mutation in ALK2 is R206H mutation.

[28'] The method according to any of [22'] to [27'], wherein the antibody is a monoclonal antibody or an antigen-binding fragment thereof.

[29'] The method according to any of [22'] to [28'], wherein the antibody or the antigen-binding fragment thereof is at least one antibody or antigen-binding fragment thereof described in the following (1) to (5):

(1) an antibody comprising a heavy chain variable region comprising CDRs consisting of the amino acid sequences of SEQ ID NO: 13 (CDRH1), SEQ ID NO: 14 (CDRH2) and SEQ ID NO: 15 (CDRH3), and a light chain variable region comprising CDRs consisting of the amino acid sequences of SEQ ID NO: 16 (CDRL1), SEQ ID NO: 17 (CDRL2) and SEQ ID NO: 18 (CDRL3), or an antigen-binding fragment thereof, or an antibody or an antigen-binding fragment thereof which cross-competes, for binding to an extracellular region of ALK2 protein, with the antibody or the antigen-binding fragment thereof;

(2) an antibody comprising a heavy chain variable region comprising CDRs consisting of the amino acid sequences of SEQ ID NO: 29 (CDRH1), SEQ ID NO: 30 (CDRH2) and SEQ ID NO: 31 (CDRH3), and a light chain variable region comprising CDRs consisting of the amino acid sequences of SEQ ID NO: 32 (CDRL1), SEQ ID NO: 33 (CDRL2) and SEQ ID NO: 34 (CDRL3), or an antigen-binding fragment thereof, or an antibody or an antigen-binding fragment thereof which cross-competes, for binding to an extracellular region of ALK2 protein, with the antibody or the antigen-binding fragment thereof;

(3) an antibody comprising a heavy chain variable region comprising CDRs consisting of the amino acid sequences of SEQ ID NO: 35 (CDRH1), SEQ ID NO: 36 (CDRH2) and SEQ ID NO: 37 (CDRH3), and a light chain variable region comprising CDRs consisting of the amino acid sequences of SEQ ID NO: 38 (CDRL1), SEQ ID NO: 39 (CDRL2) and SEQ ID NO: 40 (CDRL3), or an antigen-binding fragment thereof, or an antibody or an antigen-binding fragment thereof which cross-competes, for binding to an extracellular region of ALK2 protein, with the antibody or the antigen-binding fragment thereof;

(4) an antibody comprising a heavy chain variable region comprising CDRs consisting of the amino acid sequences of SEQ ID NO: 41 (CDRH1), SEQ ID NO: 42 (CDRH2) and SEQ ID NO: 43 (CDRH3), and a light chain variable region comprising CDRs consisting of the amino acid sequences of SEQ ID NO: 44 (CDRL1), SEQ ID NO: 45 (CDRL2) and SEQ ID NO: 46 (CDRL3), or an antigen-binding fragment thereof, or an antibody or an antigen-binding fragment thereof which cross-competes, for binding to an extracellular region of ALK2 protein, with the antibody or the antigen-binding fragment thereof; and (5) an antibody comprising a heavy chain variable region comprising CDRs consisting of the amino acid sequences of SEQ ID NO: 47 (CDRH1), SEQ ID NO: 48 (CDRH2) and SEQ ID NO: 49 (CDRH3), and a light chain variable region comprising CDRs consisting of the amino acid sequences of SEQ ID NO: 50 (CDRL1), SEQ ID NO: 51 (CDRL2) and SEQ ID NO: 52 (CDRL3), or an antigen-binding fragment thereof, or an antibody or an antigen-binding fragment thereof which cross-competes, for binding to an extracellular region of ALK2 protein, with the antibody or the antigen-binding fragment thereof.

[30'] A method for obtaining an antibody that inhibits the activation of ALK2 kinase, comprising the steps of:

(a) using a cell expressing ALK2 protein on cell surface to obtain an antibody that specifically binds to an extracellular region of the ALK2 protein;

(b) measuring the anti-ALK2 antibody selected in the step (a) for ability of the ALK2 protein to form a homodimer;

(c) measuring the anti-ALK2 antibody selected in the step (a) for ability to inhibit the formation of an ALK2-type II receptor heterodimer; and (d) when an ALK2 homodimer is formed and the formation of an ALK2-type II receptor heterodimer is inhibited, determining the anti-ALK2 antibody as having a property of inhibiting the activation of ALK2 kinase, and selecting the antibody.

[31'] A method for obtaining an antibody that inhibits ALK2-mediated BMP signal transduction, comprising the steps of:

(a) using a cell expressing ALK2 protein on cell surface to obtain an antibody that specifically binds to an extracellular region of the ALK2 protein;

(b) measuring the anti-ALK2 antibody selected in the step (a) for ability of the ALK2 protein to form a homodimer;

(c) measuring the anti-ALK2 antibody selected in the step (a) for ability to inhibit the formation of an ALK2-type II receptor heterodimer; and (d) when an ALK2 homodimer is formed and the formation of an ALK2-type II receptor heterodimer is inhibited, determining the anti-ALK2 antibody as having a property of inhibiting ALK2-mediated BMP signal transduction, and selecting the antibody.

The present specification encompasses the contents disclosed in Japanese Patent Application No. 2019-138312 from which the present application claims the priority.

The anti-ALK2 antibody of the present invention includes an antibody that recognizes human, mouse and rat ALK2, and is useful not only as a therapeutic drug but as a tool of immunological and immunohistological analysis.

DESCRIPTION OF EMBODIMENTS

Figure 1:
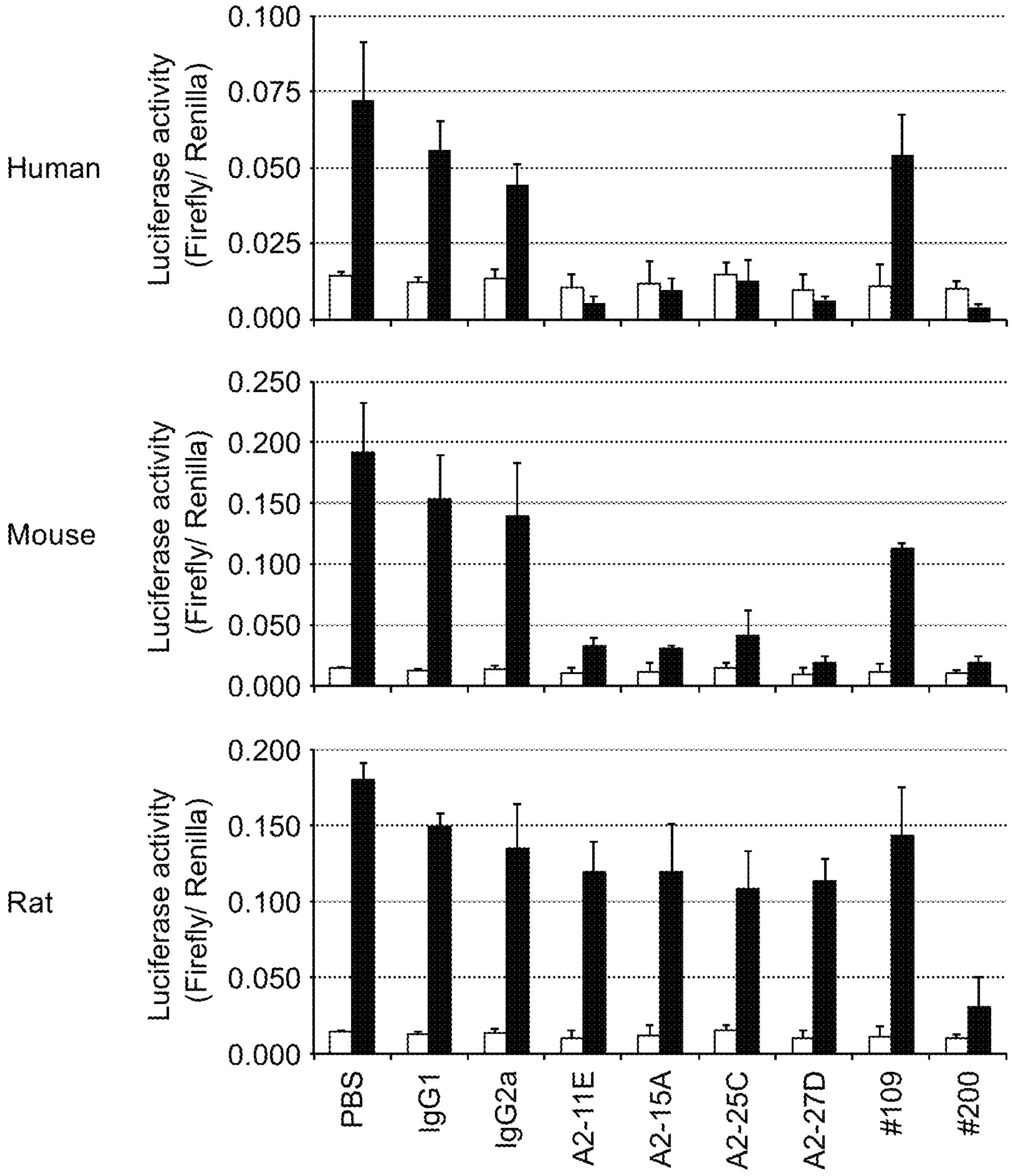
FIG. 1 This figure shows the BMP signaling inhibitory activity of various rat anti-human ALK2 antibodies. ALK2 is human, mouse and rat ALK2. The antibodies are IgG1, IgG2a, A2-11E, A2-15A, A2-25C, A2-27D, #109, and #200, and PBS (phosphate buffered saline) is a control. The BMP signal activity was measured using a BMP-specific luciferase reporter. The luciferase activity of each ALK2 is indicated by activity in the absence of BMP7 (open columns) and activity in the presence of BMP7 (filled columns).

The present invention will be described in more detail.

1. Definition

As used herein, the term "gene" includes not only DNA but mRNA, cDNA, and cRNA.

As used herein, the term "polynucleotide" is used with the same meaning as a nucleic acid and also includes, for example, DNA, RNA, probes, oligonucleotides, and primers.

As used herein, the "polypeptide" and the "protein" are used interchangeably with each other.

As used herein, the "RNA fraction" refers to a fraction containing RNA.

As used herein, the "cell" also includes cells within animal individuals and cultured cells.

As used herein, "ALK2" is used with the same meaning as ALK2 protein and includes wild-type ALK2 and mutants (also referred to as "mutant" ALK2).

As used herein, the "antigen-binding fragment of an (the) antibody", also called "functional fragment of an (the) antibody", means a partial fragment of the antibody having an activity binding to the antigen and includes, for example, Fab, $F(ab)_2$, Fab', Fv, scFv, diabodies, linear antibodies, single-chain Fvs, and multispecific antibodies formed from antibody fragments. However, the antigen-binding fragment is not limited to these molecules as long as the antigen-binding fragment has an ability to bind to ALK2 (or a property of binding to the ALK2), as in the anti-ALK2 antibody. Preferably, the antigen-binding fragment of the antibody further has an ability to inhibit BMP signal transduction (or a property of inhibiting BMP signal transduction), as in the anti-ALK2 antibody. Such an antigen-binding fragment includes not only a fragment obtained by treating a full-length molecule of the antibody protein with an appropriate enzyme but a protein produced in appropriate host cells using a genetically modified antibody gene.

As used herein, the "epitope", also called "antigenic determinant", generally refers to an antibody-binding antigenic site consisting of at least 7 amino acids, at least 8 amino acids, at least 9 amino acids, or at least 10 amino acids, of an antigen. As used herein, the epitope means a partial peptide or a partial conformation of ALK2 to which a particular anti-ALK2 antibody binds. The epitope as a partial peptide of ALK2 can be determined by a method well known to those skilled in the art such as immunoassay and can be determined, for example, by the following method: various partial structures of ALK2 are prepared. For the preparation of the partial structures, an oligopeptide synthesis technique known in the art can be used. For example, a series of polypeptide fragments having an appropriate length are prepared in order from the C or N terminus of ALK2 by use of a gene recombination technique well known to those skilled in the art. Then, the reactivity of the antibody therewith is studied to roughly determine a recognition site. Then, shorter peptides are synthesized, and the reactivity of the antibody with these peptides can be studied to determine the epitope. Alternatively, the epitope as a partial conformation of ALK2 to which a particular ALK2 antibody binds can be determined by identifying amino acid residues of ALK2 adjacent to the antibody by X-ray crystal structure analysis. Provided that a second anti-ALK2 antibody binds to a partial peptide or a partial conformation that is bound by a first anti-ALK2 antibody, the first antibody and the second antibody can be determined to share an epitope. If the specific sequence or structure of an epitope is not determined, the first antibody and the second antibody can be determined to share the epitope by confirming that the second anti-ALK2 antibody (cross-)competes with the first anti-ALK2 antibody for binding to ALK2 (i.e., that the second antibody interferes with the binding of the first antibody to ALK2). When the first antibody and the second antibody bind to a common epitope and the first antibody has an activity such as inhibitory activity against ALK2-mediated BMP signal transduction, the second antibody can also be expected to have similar activity.

As used herein, the term "compete" or "cross-compete" means that a particular antibody or an antigen-binding fragment thereof having an activity of binding to an extracellular region of ALK2 protein and another antibody interfere with each other for binding to the ALK2 protein in standard binding assay, and similarity in epitope between these two antibodies can be determined by this assay.

As used herein, the term "recognize" means that, for example, a particular antibody identifies an antigen site that is bound thereby, and interacts with or binds to the antigen site.

The heavy and light chains of an antibody molecule are known to each have three complementarity determining regions (CDRs). The complementarity determining regions, also called hypervariable domains, are located in the variable regions of the antibody heavy and light chains. These sites have a particularly highly variable primary structure and are separated at three places on the respective primary structures of heavy and light chain polypeptide chains. As used herein, the complementarity determining regions of an antibody are referred to as CDRH1, CDRH2, and CDRH3 from the amino terminus of the heavy chain amino acid sequence for the complementarity determining regions of the heavy chain and as CDRL1, CDRL2, and CDRL3 from the amino terminus of the light chain amino acid sequence for the complementarity determining regions of the light chain. These sites are proximal to each other on the conformation and determine specificity for the antigen to be bound.

As used herein, the term "several" in the phrase "one or several" refers to 2 to 10. The term "several" is preferably 10 or less, more preferably 5 or 6 or less, further preferably 2 or 3.

In the present invention, the "cross-linking ability" or the "ability to cross-link" refers to the ability of one antibody or antigen-binding fragment to bind to the respective extracellular regions of two molecules of the ALK2 protein and cross-link these molecules. Typically, ALK2 (type I receptor) forms a complex (homodimer) in the presence of a BMP ligand, followed by formation of a tetramer from the ALK2 homodimer and type II receptor homodimer, thereby activating downstream SMAD1/5/8. The anti-ALK2 antibody induces the cross-link between two molecules of ALK2, probably leading to complex-like formation even in the absence of the ligand.

The "promotion of BMP signal transduction" refers to the activation of a downstream intracellular signal transduction system via ALK2 receptor molecules.

In the present invention, the "patient" is not only a human affected by a disease, but may also be a human suspected of being affected by a disease, or may be a mammal other than a human (e.g., a dog, a cat, a mouse, and a rat).

Examples of the "sample" used in the present invention include cells expressing ALK2, and body fluids (e.g., blood, serum, plasma, urine, lymph, exudate, and cerebrospinal fluid) and tissues (normal tissues and disease tissues (e.g., tumor and organs)) containing the cells. Alternatively, the sample may be protein extracts or nucleic acid extracts (e.g., mRNA extracts and a cDNA preparation and a cRNA preparation prepared from the mRNA extracts) obtained from these samples.

In the present invention, the "immunohistochemistry (IHC)" means a histological (histochemical) approach of detecting an antigen in a tissue preparation. This term is synonymous with "immuno-antibody method" and is used interchangeably with "immunostaining".

2. ALK2

ALK2 is a transmembrane serine-threonine kinase receptor that binds to a ligand of the transforming growth factor-β (TGF-β) family and activates intracellular signals. ALK2 binds to bone morphogenetic protein (BMP) at the N-terminal extracellular region and activates a downstream intracellular signal transduction system through intracellular serine-threonine kinase. In this respect, it is known that type II receptor phosphorylates the GS (rich in glycine and serine) domain of ALK2 (type I receptor) and thereby activates ALK2 (T. Katagiri, J. Oral Biosciences 54 (2012): 119-123).

BMP is a multifunctional growth factor belonging to the TGF-β superfamily, and approximately 20 BMP family members have been identified. BMP has been confirmed to induce ectopic bone formation in soft tissues including skeletal muscle tissues and is therefore considered to participate in diseases promoting abnormal bone formation. BMP2 and BMP4 are considered to have higher affinity for ALK3 than that for ALK2. Since ALK3 is expressed ubiquitously as compared with ALK2, BMP2 or BMP4 seems to be often used in general in experiments of inducing ectopic ossification at various sites. On the other hand, BMP7 has relatively high affinity for ALK2. BMP9 is generally considered to have high affinity for ALK1 and has also been found to have relatively high affinity for ALK2. In FOP, ectopic ossification occurs via ALK2. Therefore, the presence or absence of therapeutic and/or prophylactic effects on FOP can probably be confirmed by testing efficacy for ectopic osteoinduction caused by the activation of ALK2-mediated signals by BMP7 and BMP9.

In recent years, fibrodysplasia ossificans progressiva (FOP) which causes ectopic ossification in soft tissues such as skeletal muscle tissues, diffuse idiopathic skeletal hyperostosis (DISH) involving the ossification of enthesis, and diffuse intrinsic pontine glioma (DIPG) have been revealed as genetic diseases that increase intracellular signals by a mutation associated with an amino acid substitution in ALK2 gene. Since any antibody that can specifically recognize in vivo ALK2 has not previously been established, a cell population or biochemical signals involved in the onset of these diseases still remain unclear and any effective treatment method therefor has not yet been established.

The ALK2 gene is a responsible gene for FOP, and encodes a receptor of BMP that induces ectopic bone formation in soft tissues including skeletal muscle tissues. Mutant ALK2 having amino acid substitutions has been found from familial and sporadic FOP cases. For example, L196P (mutation that substitutes leucine at position 196 by proline), delP197_F198insL (also referred to as "PF197-8L") (mutation that deletes proline at position 197 and phenylalanine at position 198 and inserts leucine), R202I (mutation that substitutes arginine at position 202 by isoleucine), R206H (mutation that substitutes arginine at position 206 by histidine), Q207E (mutation that substitutes glutamine at position 207 by glutamic acid), R258S (mutation that substitutes arginine at position 258 by serine), R258G (mutation that substitutes arginine at position 258 by glycine), G325A (mutation that substitutes glycine at position 325 by alanine), G328E (mutation that substitutes glycine at position 328 by glutamic acid), G328R (mutation that substitutes glycine at position 328 by arginine), G328W (mutation that substitutes glycine at position 328 by tryptophan), G356D (mutation that substitutes glycine at position 356 by aspartic acid), and R375P (mutation that substitutes arginine at position 375 by proline) in the amino acid sequence of SEQ ID NO: 1 are known as activating mutations in human ALK2. K400E (mutation that substitutes lysine at position 400 by glutamic acid) is known from DISH cases.

Mutant ALK2 having an amino acid substitution has also been found from DIPG cases. R206H, R258G, G328E, G328V (mutation that substitutes glycine at position 328 by valine), G328W, G356D, and the like in the amino acid sequence of SEQ ID NO: 1 are known as activating mutations in human ALK2.

ALK2 can be obtained by in vitro synthesis or by production from host cells through gene manipulation. Specifically, ALK2 cDNA is inserted into a vector that permits expression. Then, the ALK2 protein can be obtained by synthesis in a solution containing enzymes, substrates, and energy substances necessary for transcription and translation, or by expression of the ALK2 cDNA in other prokaryotic or eukaryotic host cells transformed with the vector.

ALK2 used herein is ALK2 derived from a mammal including a human or a mouse. For example, the amino acid sequence and nucleotide sequence of human ALK2 are available with reference to GenBank Accession No. NM-001105. Herein, the amino acid sequence is also disclosed as SEQ ID NO: 1. The amino acid sequence and nucleotide sequence of mouse ALK2 are available with reference to GenBank Accession No. NP-001103674. Herein the amino acid sequence is also disclosed as SEQ ID NO: 2. Furthermore, the amino acid sequences of monkey, rat and dog ALK2s are available with reference to GenBank Accession Nos. NM-001260761, NP_077812 (SEQ ID NO: 3), and XM_549615.5, respectively. ALK2, as mentioned above, is also called ACVR1 (activin A type I receptor 1) or ACTR1 (activin receptor type 1), and all of these terms represent the same molecules.

The ALK2 cDNA can be obtained by, for example, a so-called PCR method which involves carrying out polymerase chain reaction (hereinafter, referred to as "PCR") (Saiki, R. K., et al., Science, (1988) 239, 487-49), for example, using a cDNA library expressing the ALK2 cDNA as a template and using primers specifically amplifying the ALK2 cDNA.

3. Anti-ALK2 Antibody and Production Thereof

The anti-ALK2 antibody of the present invention can be obtained by establishing hybridomas producing monoclonal antibodies that recognize an extracellular region of ALK2, and selecting a clone having a feature that has not previously been obtained, for example, a clone that strongly inhibits the activity of human or mouse ALK2 as well as rat ALK2, a clone that exhibits a positive image as to the localization, etc. of ALK2 by immunostaining using frozen sections, paraffin sections or the like of mouse tissues, or a clone that can recognize ALK2 in Western blot, from among many hybridoma clones.

The anti-ALK2 antibody of the present invention can be obtained by a method described in, for example, WO2009/

091048, WO2011/027808, or WO2012/133572. Specifically, nonhuman animals are immunized with the antigen of interest. Lymphs, lymph tissues, blood samples, or bone marrow-derived cells are collected from the animals after establishment of immunity. Plasma cells and/or plasmablasts of the nonhuman animals specifically binding to the antigen of interest are selected. A gene of an antibody to the antigen of interest is collected from the obtained plasma cells and/or plasmablasts, and its nucleotide sequence is identified. The antibody or an antibody fragment thereof can be obtained on the basis of the identified nucleotide sequence of the gene. Alternatively, the antibody or the antibody fragment can be obtained by obtaining plasma cells and/or plasmablasts in the same way as above from the blood of a human infected patient.

The anti-ALK2 antibody of the present invention encompasses, for example, the following antibody or antigen-binding fragment thereof.

An antibody or an antigen-binding fragment thereof which specifically recognizes polypeptides consisting of the following amino acid sequences (a) to (c) and inhibits BMP signal transduction:

(a) an amino acid sequence consisting of amino acid numbers 21 to 123 of the amino acid sequence of SEQ ID NO: 1;

(b) an amino acid sequence consisting of amino acid numbers 21 to 123 of the amino acid sequence of SEQ ID NO: 2; and (c) an amino acid sequence consisting of amino acid numbers 21 to 123 of the amino acid sequence of SEQ ID NO: 3.

The amino acid sequences of SEQ ID NOs: 1, 2, and 3 represent those of human ALK2, mouse ALK2, and rat ALK2, respectively, and their amino acid sequences from positions 21 to 123 correspond to an extracellular region of ALK2. When the amino acid sequences of the regions shown in FIG. 2A are compared, the mouse and human regions have very high sequence identity (approximately 98%) and the human and rat regions have sequence identity of approximately 94%.

Although antibodies that recognize the amino acid sequences (a) and (b) have previously been obtained, any antibody that can also recognize the amino acid sequence (c) has not been obtained. The conventional antibodies are difficult to use in tissue staining by immunostaining or in Western blot for measuring the presence or amount of ALK2. On the other hand, the anti-ALK2 antibody having the properties described above can recognize human, mouse and rat ALK2 and besides, permits its use in immunostaining.

As shown in the results of FIG. 2B, the amino acid residue at amino acid number 64 in the amino acid sequence of ALK2 influences the BMP signal transduction inhibitory activity of an antibody. In FIG. 2B, the antibody used was A2-27D. Therefore, the amino acid residue at amino acid number 64 in the amino acid sequence of ALK2 that is recognized thereby is histidine. The antibody of the present invention is capable of binding to an epitope comprising arginine at the amino acid number 64 in the amino acid sequence of SEQ ID NO: 3 and has BMP signal transduction inhibitory activity.

The antibody of the present invention encompasses, for example, at least one of the following:

(1) an antibody or an antigen-binding fragment thereof in which the heavy chain sequence comprises a variable region comprising CDR sequences consisting of the amino acid sequences of SEQ ID NO: 13 (CDRH1), SEQ ID NO: 14 (CDRH2) and SEQ ID NO: 15 (CDRH3), and the light chain sequence comprises a variable region comprising CDR sequences consisting of the amino acid sequences of SEQ ID NO: 16 (CDRL1), SEQ ID NO: 17 (CDRL2) and SEQ ID NO: 18 (CDRL3);

(2) an antibody comprising a heavy chain variable region sequence consisting of the amino acid sequence of SEQ ID NO: 9 and a light chain variable region sequence consisting of the amino acid sequence of SEQ ID NO: 11, or an antigen-binding fragment thereof;

(3) an antibody or an antigen-binding fragment thereof which cross-competes, for binding to an extracellular region of ALK2 protein, with the antibody or the antigen-binding fragment thereof described in (1) or (2);

(4) an antibody or an antigen-binding fragment thereof which comprises an amino acid sequence having at least 95% identity to any of the amino acid sequences in (1) to (3);

(5) an antibody or an antigen-binding fragment thereof which comprises an amino acid sequence having at least 99% identity to any of the amino acid sequences in (1) to (3); and (6) an antibody or an antigen-binding fragment thereof which comprises an amino acid sequence comprising a substitution(s), a deletion(s), or an addition(s) of one or several amino acid residues in any of the amino acid sequences in (1) to (3).

In the present invention, other anti-ALK2 antibodies that may be used in immunostaining or Western blot encompass, for example, at least one of the following antibodies or antigen-binding fragments thereof:

(7) an antibody or an antigen-binding fragment thereof having binding activity to ALK2 protein, where the antibody or the fragment is: an antibody or an antigen-binding fragment thereof in which the heavy chain sequence comprises a variable region comprising CDR sequences consisting of the amino acid sequences of SEQ ID NO: 23 (CDRH1), SEQ ID NO: 24 (CDRH2) and SEQ ID NO: 25 (CDRH3), and the light chain sequence comprises a variable region comprising CDR sequences consisting of the amino acid sequences of SEQ ID NO: 26 (CDRL1), SEQ ID NO: 27 (CDRL2) and SEQ ID NO: 28 (CDRL3); or an antibody or an antigen-binding fragment thereof which cross-competes, for binding to an extracellular region of the ALK2 protein, with the antibody or the antigen-binding fragment;

(8) an antibody consisting of a heavy chain comprising a heavy chain variable region sequence consisting of the amino acid sequence of SEQ ID NO: 19 and a light chain comprising a light chain variable region sequence consisting of the amino acid sequence of SEQ ID NO: 21, or an antigen-binding fragment thereof, or an antibody or an antigen-binding fragment thereof which cross-competes, for binding to an extracellular region of the ALK2 protein, with the antibody or the antigen-binding fragment;

(9) an antibody or an antigen-binding fragment thereof which comprises an amino acid sequence having at least 95% identity to any of the amino acid sequences in (7) and (8); (10) an antibody or an antigen-binding fragment thereof which comprises an amino acid sequence having at least 99% identity to any of the amino acid sequences in (7) and (8); and (11) an antibody or an antigen-binding fragment thereof which comprises an amino acid sequence comprising a substitution(s), a deletion(s), or an addition(s) of one or several amino acid residues in any of the amino acid sequences in (7) and (8).

In an embodiment of the present invention, the antibody and the antigen-binding fragment thereof can be, for example, a monoclonal antibody or a polyclonal antibody, preferably a monoclonal antibody, or a rat antibody, a chimeric antibody, a humanized antibody, a human antibody, a diabody, a multispecific antibody, Fab, $F(ab)_2$, Fab', Fv, or scFv (single-chain Fv).

In another embodiment of the present invention, the isotype of the heavy chain constant region can be, for example, IgG2b.

Other anti-ALK2 antibodies that may be used in the present invention have the following properties.

An antibody or an antigen-binding fragment thereof having a property of specifically binding to an extracellular region of ALK2 to form an ALK2 homodimer, a property of inhibiting the formation of an ALK2-type II receptor heterodimer, and a property of inhibiting the activation of ALK2 kinase.

Alternatively, an antibody or an antigen-binding fragment thereof having a property of specifically binding to an extracellular region of ALK2 to form an ALK2 homodimer, a property of inhibiting the formation of an ALK2-type II receptor heterodimer, and a property of inhibiting BMP signal transduction.

The antibody having these properties may be obtained by a method comprising the following steps (a) to (d) (see e.g., Examples 9 and 10 mentioned later):

(a) using a cell expressing ALK2 protein on cell surface to obtain an antibody that specifically binds to an extracellular region of the ALK2 protein;

(b) measuring the anti-ALK2 antibody selected in the step (a) for ability of the ALK2 protein to form a homodimer;

(c) measuring the anti-ALK2 antibody selected in the step (a) for ability to inhibit the formation of an ALK2-type II receptor heterodimer; and (d) when an ALK2 homodimer is formed and the formation of an ALK2-type II receptor heterodimer is inhibited, determining the anti-ALK2 antibody as having a property of inhibiting the activation of ALK2 kinase, or a property of inhibiting ALK2-mediated BMP signal transduction, and selecting the antibody.

Examples thereof include the following antibodies:

a1) the aforementioned antibody or antigen-binding fragment thereof having binding activity to an extracellular region of ALK2 protein, where the antibody or the fragment is: an antibody or an antigen-binding fragment thereof in which the heavy chain sequence comprises a variable region comprising CDR sequences consisting of the amino acid sequences of SEQ ID NO: 13 (CDRH1), SEQ ID NO: 14 (CDRH2) and SEQ ID NO: 15 (CDRH3), and the light chain sequence comprises a variable region comprising CDR sequences consisting of the amino acid sequences of SEQ ID NO: 16 (CDRL1), SEQ ID NO: 17 (CDRL2) and SEQ ID NO: 18 (CDRL3); or an antibody or an antigen-binding fragment thereof which cross-competes, for binding to the extracellular region of the ALK2 protein, with the antibody or the antigen-binding fragment.

a2) the aforementioned antibody consisting of a heavy chain comprising a heavy chain variable region sequence consisting of the amino acid sequence of SEQ ID NO: 9 and a light chain comprising a light chain variable region sequence consisting of the amino acid sequence of SEQ ID NO: 11, or an antigen-binding fragment thereof, or an antibody or an antigen-binding fragment thereof which cross-competes, for binding to an extracellular region of ALK2 protein, with the antibody or the antigen-binding fragment.

a3) an antibody or an antigen-binding fragment thereof having binding activity to an extracellular region of ALK2 protein, where the antibody or the fragment is: an antibody or an antigen-binding fragment thereof in which the heavy chain sequence comprises a variable region comprising CDR sequences consisting of the amino acid sequences of SEQ ID NO: 29 (CDRH1), SEQ ID NO: 30 (CDRH2) and SEQ ID NO: 31 (CDRH3), and the light chain sequence comprises a variable region comprising CDR sequences consisting of the amino acid sequences of SEQ ID NO: 32 (CDRL1), SEQ ID NO: 33 (CDRL2) and SEQ ID NO: 34 (CDRL3); or an antibody or an antigen-binding fragment thereof which cross-competes, for binding to the extracellular region of the ALK2 protein, with the antibody or the antigen-binding fragment.

a4) an antibody or an antigen-binding fragment thereof having binding activity to an extracellular region of ALK2 protein, where the antibody or the fragment is: an antibody or an antigen-binding fragment thereof in which the heavy chain sequence comprises a variable region comprising CDR sequences consisting of the amino acid sequences of SEQ ID NO: 35 (CDRH1), SEQ ID NO: 36 (CDRH2) and SEQ ID NO: 37 (CDRH3), and the light chain sequence comprises a variable region comprising CDR sequences consisting of the amino acid sequences of SEQ ID NO: 38 (CDRL1), SEQ ID NO: 39 (CDRL2) and SEQ ID NO: 40 (CDRL3); or an antibody or an antigen-binding fragment thereof which cross-competes, for binding to the extracellular region of the ALK2 protein, with the antibody or the antigen-binding fragment.

a5) an antibody or an antigen-binding fragment thereof having binding activity to an extracellular region of ALK2 protein, where the antibody or the fragment is: an antibody or an antigen-binding fragment thereof in which the heavy chain sequence comprises a variable region comprising CDR sequences consisting of the amino acid sequences of SEQ ID NO: 41 (CDRH1), SEQ ID NO: 42 (CDRH2) and SEQ ID NO: 43 (CDRH3), and the light chain sequence comprises a variable region comprising CDR sequences consisting of the amino acid sequences of SEQ ID NO: 44 (CDRL1), SEQ ID NO: 45 (CDRL2) and SEQ ID NO: 46 (CDRL3); or an antibody or an antigen-binding fragment thereof which cross-competes, for binding to the extracellular region of the ALK2 protein, with the antibody or the antigen-binding fragment.

a6) an antibody or an antigen-binding fragment thereof having binding activity to an extracellular region of ALK2 protein, where the antibody or the fragment is: an antibody or an antigen-binding fragment thereof in which the heavy chain sequence comprises a variable region comprising CDR sequences consisting of the amino acid sequences of SEQ ID NO: 47 (CDRH1), SEQ ID NO: 48 (CDRH2) and SEQ ID NO: 49 (CDRH3), and the light chain sequence comprises a variable region comprising CDR sequences consisting of the amino acid sequences of SEQ ID NO: 50 (CDRL1), SEQ ID NO: 51 (CDRL2) and SEQ ID NO: 52 (CDRL3); or an antibody or an antigen-binding fragment thereof which cross-competes, for binding to the extracellular region of the ALK2 protein, with the antibody or the antigen-binding fragment.

a7) an antibody or an antigen-binding fragment thereof which comprises an amino acid sequence having at least 95% identity to any one amino acid sequence selected from the amino acid sequences in a1) to a6);

a8) an antibody or an antigen-binding fragment thereof which comprises an amino acid sequence having at least 99% identity to any one amino acid sequence selected from the amino acid sequences in a1) to a6); and a9) an antibody or an antigen-binding fragment thereof which comprises an amino acid sequence comprising a substitution(s), a deletion(s), or an addition(s) of one or several amino acid residues in any one amino acid sequence selected from the amino acid sequences in a1) to a6).

The antibody used in the present invention against an extracellular region of ALK2 can be obtained according to methods known in the art (e.g., Kohler and Milstein, Nature (1975) 256, p. 495-497; and Kennet, R. ed., Monoclonal Antibodies, p. 365-367, Plenum Press, N.Y. (1980)). Specifically, the monoclonal antibody can be obtained by fusing antibody-producing cells that produce the antibody against an extracellular region of ALK2 with myeloma cells to establish hybridomas. The obtained antibody can be tested for its binding activity and cross-linking ability to ALK2, etc. to select suitable antibodies.

Several methods are known for the determination of CDR sequences. Examples thereof include the definition of Abm, the definition of Chothia, the definition of Kabat, and the definition of Imgt® (The international ImMunoGeneTics information System®). The CDR sequences of the antibody of the present invention may be defined by any method.

The antibody used in the present invention include monoclonal antibodies against an extracellular region of ALK2 described above as well as, for example, polyclonal antibodies, recombinant antibodies artificially modified for the purpose of, for example, reducing heterogeneous antigenicity against humans, for example, chimeric antibodies, humanized antibodies, human antibodies, and the like. These antibodies can be produced by use of known methods.

Examples of the chimeric antibody can include chimeric antibodies comprising variable regions and constant regions (Fc) of antibodies derived from different species, for example, the variable regions of a mouse- or rat-derived antibody joined to human-derived constant regions (see Proc. Natl. Acad. Sci. U.S.A., 81, 6851-6855, (1984)).

Examples of the humanized antibody can include an antibody comprising CDRs alone integrated into a human-derived antibody (see Nature (1986) 321, p. 522-525), and an antibody comprising the CDR sequences as well as amino acid residues of a portion of frameworks grafted into a human antibody by a CDR grafting method (International Publication No. WO90/07861).

A CDR-modified humanized antibody prepared by substitution of 1 to 3 amino acid residues in each CDR by other amino acid residues is also included in the antibody used in the present invention as long as the humanized antibody has an activity of binding to ALK2.

Further examples of the antibody used in the present invention can include a human antibody. The anti-ALK2 human antibody means a human antibody produced from only human chromosome-derived antibody gene sequences. The anti-ALK2 human antibody can be obtained by a method using human antibody-producing mice carrying human chromosome fragments that comprise human antibody heavy and light chain genes (see e.g., Tomizuka, K. et al., Nature Genetics (1997), 16, p. 133-143; Kuroiwa, Y. et al., Nuc. Acids Res. (1998), 26, p. 3447-3448; Yoshida, H. et al., Animal Cell Technology: Basic and Applied Aspects vol. 10, p. 69-73 (Kitagawa, Y., Matsuda, T. and Iijima, S. eds.), Kluwer Academic Publishers, 1999; and Tomizuka, K. et al., Proc. Natl. Acad. Sci. USA (2000), 97, p. 722-727).

Specifically, such a human antibody-producing mouse can be created as a recombinant animal in which the endogenous immunoglobulin heavy and light chain gene loci have been disrupted and instead human immunoglobulin heavy and light chain gene loci are integrated via a vector, for example, a human artificial chromosome (HAC) vector or a mouse artificial chromosome (MAC) vector, by preparing a knock-out animal or a transgenic animal or by crossing these animals.

Alternatively, eukaryotic cells may be transformed with cDNAs encoding the heavy and light chains, respectively, of such a human antibody, preferably with vectors comprising the cDNAs, by a gene recombination technique. The transformed cells producing a recombinant human monoclonal antibody are cultured. This antibody can be obtained from the culture supernatant. In this context, for example, eukaryotic cells, preferably mammalian cells such as CHO cells, lymphocytes, or myeloma cells, can be used as hosts.

Also, a method for obtaining a phage display-derived human antibody selected from a human antibody library is known (see e.g., Wormstone, I. M. et al., Investigative Ophthalmology & Visual Science (2002), 43 (7), p. 2301-2308; Carmen, S. et al., Briefings in Functional Genomics and Proteomics (2002), 1 (2), p. 189-203; and Siriwardena, D. et al., Ophthalmology (2002), 109 (3), p. 427-431).

For example, a phage display method (Nature Biotechnology (2005), 23, (9), p. 1105-1116) can be used, which involves allowing the variable regions of a human antibody to be expressed as single-chain Fv (scFv) on phage surface and selecting a phage binding to the antigen. The phage selected on the basis of its ability to bind to the antigen can be subjected to gene analysis to determine DNA sequences encoding the variable regions of the human antibody binding to the antigen. If the DNA sequence of scFv binding to the antigen is determined, an expression vector having this sequence can be prepared and transferred to appropriate hosts, followed by expression to obtain the human antibody (WO92/01047, WO92/20791, WO93/06213, WO93/11236, WO93/19172, WO95/01438, WO95/15388, Annu. Rev. Immunol (1994), 12, p. 433-455; and Nature Biotechnology (2005), 23 (9), p. 1105-1116).

When an antibody binds to or recognizes a partial conformation of an antigen, the epitope for this antibody can be determined by identifying amino acid residues on the antigen adjacent to the antibody by use of X-ray structure analysis. For example, the antibody or a fragment thereof and the antigen or a fragment thereof can be bound to each other, crystallized, and structurally analyzed to identify amino acid residues on the antigen having an interaction distance between the amino acid residue and the antibody. The interaction distance is 8 angstroms or smaller, preferably 6 angstroms or smaller, more preferably 4 angstroms or smaller. One or more amino acid residues having such an interaction distance with the antibody can constitute the epitope (antigenic determinant) for the antibody. When the number of such amino acid residues is two or more, these amino acids may not be necessarily adjacent to each other on the primary sequence.

The antibody described above can be evaluated for its activity of binding to the antigen by, for example, a method described in Example 2, Example 6, Example 9 or Example 10 of WO2016/121908 to select suitable antibodies. The dissociation constant ($K_D$) of the antibody is, for example, $1\times10^{-6}$ to $1\times10^{-12}$ M or less, though not limited to this range as long as the therapeutic or prophylactic effect of interest is obtained. The dissociation constant of the antibody for the antigen (ALK2) can be measured using Biacore T200 (GE Healthcare Bio-Sciences Corp.) based on surface plasmon resonance (SPR) as detection principles. For example, the antibody set to an appropriate concentration is reacted as an analyte with the antigen immobilized as a ligand on a solid phase. The association and dissociation therebetween can be measured to obtain an association rate constant ka1, a dissociation rate constant kd1, and a dissociation constant (KD; KD=kd1/ka1). The evaluation of binding activity to ALK2 is not limited by use of Biacore T200 and may be conducted using, for example, an instrument based on surface plasmon resonance (SPR) as detection principles, KinExA (Sapidyne Instruments Inc.) based on kinetic exclusion assay as detection principles, BLItz system (Pall Corp.) based on bio-layer interferometry as detection principles, or ELISA (enzyme-linked immunosorbent assay).

For the antibody described above, for example, a fusion of ALK2 and LgBiT or SmBiT is expressed in in vitro cells using NanoLuc® Binary Technology: NanoBiT® (Promega Corp.), and the interaction of the ALK2 protein with the antibody can be detected from luminescence brought about by structural complementarity of LgBiT and SmBiT (e.g., ACS Chem. Biol. 2012, 7, 1848-1857; and ACS Chem. Biol. 2016, 11, 400-408).

One example of another indicator for comparing the properties of antibodies can include the stability of the antibodies. Differential scanning calorimetry (DSC) is a method that can rapidly and accurately measure a transition midpoint (Tm), which serves as a good indicator for the relative structural stability of proteins. Tm values can be measured using DSC and compared to determine difference in thermal stability. The preservation stability of an antibody is known to correlate with the thermal stability of the antibody to some extent (Lori Burton, et al., Pharmaceutical Development and Technology (2007) 12, p. 265-273). A suitable antibody can be selected with its thermal stability as the indicator. Examples of other indicators for selecting the antibody can include high yields in appropriate host cells and low aggregation in an aqueous solution. For example, an antibody having the highest yield does not always exhibit the highest thermal stability. Therefore, it is necessary to select an antibody most suitable for administration to humans by comprehensive judgment based on the indicators mentioned above.

A method for obtaining a single-chain immunoglobulin by linking the full-length sequences of antibody heavy and light chains using an appropriate linker is also known (Lee, H-S, et al., Molecular Immunology (1999) 36, p. 61-71; and Shirrmann, T. et al., mAbs (2010), 2, (1) p. 1-4). Such single-chain immunoglobulins can be dimerized to retain a structure and activity similar to those of antibodies which are originally tetramers. Alternatively, the antibody used in the present invention may be an antibody that has a single heavy chain variable region and lacks a light chain sequence. Such an antibody, called single-domain antibody (sdAb), nanobody or llama antibody (heavy chain antibody), has actually been observed in camels or llamas and has been reported to maintain the ability to bind to an antigen (Muyldemans S. et al., Protein Eng. (1994) 7 (9), 1129-35; and Hamers-Casterman C. et al., Nature (1993) 363 (6428) 446-8). These antibodies may also be interpreted as an antigen-binding fragment of the antibody according to the present invention.

The antibody-dependent cellular cytotoxic activity of the antibody used in the present invention can be enhanced by adjusting the modification of the sugar chain bound with the antibody. For example, methods described in WO99/54342, WO2000/61739, and WO2002/31140 are known as such a technique of adjusting the sugar chain modification of the antibody, though this technique is not limited thereto.

Specific examples of the antibody gene include a gene (or a polynucleotide) encoding a heavy chain sequence and a gene (or a polynucleotide) encoding a light chain sequence of the antibody described above, and a combination of these genes (or polynucleotides).

In the case of preparing an antibody by isolating the antibody gene and then transferring the gene to an appropriate host, the appropriate host can be used in combination with an expression vector comprising the gene (or the polynucleotide).

For the transformation of host cells, a heavy chain sequence gene (or polynucleotide) and a light chain sequence gene (or polynucleotide) may be inserted in a same expression vector or may be inserted in separate expression vectors. In the case of using host eukaryotic cells, animal cells, plant cells, or eukaryotic microorganisms can be used. Examples of the animal cells can include mammalian cells, for example, monkey COS cells (Gluzman, Y., Cell (1981) 23, p. 175-182, ATCC CRL-1650), mouse fibroblast NIH3T3 (ATCC No. CRL-1658), and dihydrofolate reductase-deficient cell lines (Urlaub, G. and Chasin, L. A., Proc. Natl. Acad. Sci. U.S.A. (1980) 77, p. 4126-4220) of Chinese hamster ovary cells (CHO cells, ATCC CCL-61). In the case of using prokaryotic cells, examples thereof can include *E. coli* and *Bacillus subtilis*. The antibody gene of interest is transferred to these cells by transformation, and the transformed cells are cultured in vitro to obtain antibodies. Such culture methods may differ in yield depending on the sequences of the antibodies. An antibody that is easy to produce as a drug can be selected with its yield as an indicator from among antibodies having equivalent binding activity.

The isotype of the antibody used in the present invention can be any isotype having the ability to bind to ALK2. Examples thereof can include, but are not limited to, IgG (IgG1, IgG2, IgG3, and IgG4), IgM, IgA (IgA1 and IgA2), IgD, and IgE. Preferred examples of the isotype can include IgG and IgM, more preferably IgG1, IgG2, and IgG4.

In the case of using IgG1 as an isotype of the antibody used in the present invention, the effector functions can be adjusted by substitution of a part of amino acid residues in constant regions (see WO88/07089, WO94/28027, and WO94/29351). Examples of such a variant of IgG1 include IgG1 LALA (IgG1-L234A, L235A) and IgG1 LAGA (IgG1-L235A, G237A). IgG1 LALA is preferred.

In the case of using IgG4 as an isotype of the antibody used in the present invention, splitting unique to IgG4 can be suppressed so as to give extended half-life by substitution of a part of amino acid residues in constant regions (see Molecular Immunology, 30 (1): 105-108 (1993)). Examples of such a mutant of IgG4 include IgG4 pro (IgG4-S241P).

The antibody used in the present invention may be an antigen-binding fragment of the antibody having the antigen-binding site of the antibody, or a modified form thereof. A fragment of the antibody can be obtained by treating the antibody with a proteolytic enzyme such as papain or pepsin or by expressing a genetically altered antibody gene in appropriate cultured cells. Among such antibody fragments, a fragment that maintains the whole or a portion of the functions possessed by the full-length molecule of the antibody can be referred to as an antigen-binding fragment of the antibody. Examples of the functions of the antibody can generally include antigen binding activity, activity of inhibiting the activity of the antigen, activity of enhancing the activity of the antigen, antibody-dependent cellular cytotoxic activity, complement-dependent cytotoxic activity, and complement-dependent cellular cytotoxic activity. The function possessed by the antigen-binding fragment of the antibody according to the present invention is binding activity to ALK2, a property of forming an ALK2 homodimer (e.g., cross-linking ability), and/or a property of inhibiting the formation of an ALK2-type II receptor heterodimer. The binding activity to ALK2 is antibody's or antigen-binding fragment's property of (preferably, specifically) binding to the ALK2 molecule, and is preferably an activity of inhibiting the kinase activity of ALK2, more preferably an activity of inhibiting ALK2-mediated BMP signal transduction.

The antibody used in the present invention may have enhanced affinity for the antigen by multimerization. Antibodies of the same type may be multimerized, or a plurality of antibodies recognizing a plurality of epitopes, respectively, of the same antigen may be multimerized. Examples of a method for multimerizing these antibodies can include the binding of two scFvs to an IgG CH3 domain, the binding thereof to streptavidin, and the introduction of a helix-turn-helix motif.

The antibody used in the present invention may be a polyclonal antibody which is a mixture of plural types of anti-ALK2 antibodies differing in amino acid sequence. One example of the polyclonal antibody can include a mixture of plural types of antibodies differing in CDRs. An antibody obtained by culturing a mixture of cells producing different antibodies, followed by purification from the cultures can be used as such a polyclonal antibody (see WO2004/061104).

The antibody used in the present invention may be an antibody having 80% to 99% or higher identity as compared with the heavy and/or light chains of the antibody. Herein the term "identity" has general definition used in the art. The % identity refers to the percentage of the number of identical amino acids relative to the total number of amino acids (including gaps) when two amino acid sequences are aligned so as to give the largest consistency of amino acids. Antibodies that have an ability to bind to the antigen, a property of forming an ALK2 homodimer (e.g., cross-linking ability), a property of inhibiting the formation of an ALK2-type II receptor heterodimer, an inhibitory effect on ALK2 kinase activation and/or an inhibitory effect on BMP signal transduction at analogous levels to the antibodies described above can be selected by combining sequences that exhibit high identity to the amino acid sequences of the heavy and light chains. Such identity is generally 80% higher or 85% or higher identity, preferably 90% or higher, 91% or higher, 92% or higher, 93% or higher, or 94% or higher identity, more preferably 95% or higher, 96% or higher, 97% or higher, or 98% or higher identity, most preferably 99% or higher identity. Alternatively, antibodies that have various effects equivalent to the antibodies described above may be selected by combining amino acid sequences that comprise a substitution(s), a deletion(s), and/or an addition(s) of one or several amino acid residues in the amino acid sequences of the heavy and/or light chains. The number of amino acid residues to be substituted, deleted, and/or added is generally 10 or less amino acid residues, preferably 5 or 6 or less amino acid residues, more preferably 2 or 3 or less amino acid residues, most preferably 1 amino acid residue.

The heavy chain of an antibody produced by cultured mammalian cells is known to lack a carboxyl-terminal lysine residue (Journal of Chromatography A, 705: 129-134 (1995)). Also, the heavy chain of such an antibody is known to lack two carboxyl-terminal amino acid residues (glycine and lysine) and instead have an amidated proline residue at the carboxy terminus (Analytical Biochemistry, 360: 75-83 (2007)).

An N-terminal glutamine or glutamic acid residue in the heavy or light chain of an antibody is known to be modified by pyroglutamylation during preparation of the antibody, and the antibody used in the present invention may have such a modification (WO2013/147153).

Such deletion in the heavy chain sequence or modification in the heavy or light chain sequence does not influence the ability of the antibody to bind to the antigen and its effector functions (complement activation, antibody-dependent cytotoxic effects, etc.).

Thus, the antibody used in the present invention also encompasses an antibody that has received the deletion or the modification. Examples thereof can include a deletion variant derived from a heavy chain by the deletion of 1 or 2 amino acids at its carboxyl terminus, an amidated form of the deletion variant (e.g., a heavy chain having an amidated proline residue at the carboxyl-terminal site), and an antibody having a pyroglutamylated N-terminal amino acid residue in a heavy or light chain thereof. However, the deletion variant at the carboxyl terminus of the antibody heavy chain used in the present invention is not limited to the types described above as long as the deletion variant maintains the ability to bind to the antigen and the effector functions. Two heavy chains constituting the antibody used in the present invention may be heavy chains of any one type selected from the group consisting of the full-length heavy chain and the deletion variants described above, or may be a combination of heavy chains of any two types selected therefrom. The quantitative ratio of each deletion variant may be influenced by the type of cultured mammalian cells producing the antibody according to the present invention, and culture conditions. Examples of such a case can include the deletion of one carboxyl-terminal amino acid residue each in both the two heavy chains as main components of the antibody.

The identity between two types of amino acid sequences can be determined using the default parameters of Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm is also available by access to www.ncbi.nlm.nih.gov/blast on the Internet. Two types of percentage values, Identity (or Identities) and Positivity (or Positivities), are calculated according to the Blast algorithm. The former is a value that indicates identical amino acid residues between two types of amino acid sequences between which the identity should be determined. The latter is a numerical value determined by also taking into consideration similar amino acid residues in terms of their chemical structures. Herein, the value of identity is defined as the value of "Identity" when amino acid residues are identical between the amino acid sequences.

An antibody conjugated with any of various molecules such as polyethylene glycol (PEG) can also be used as a modified form of the antibody.

The antibody used in the present invention may further be any of conjugates formed by these antibodies with other drugs (immunoconjugates). Examples of such an antibody can include an antibody conjugated with a radioactive material or a compound having a pharmacological effect (Nature Biotechnology (2005) 23, p. 1137-1146).

The obtained antibody can be purified until homogeneous. A protein separation and purification method usually used can be used for the separation and purification of the antibody. The antibody can be separated and purified by appropriately selected or combined approaches, for example, column chromatography, filtration through a filter, ultrafiltration, salting-out, dialysis, preparative polyacrylamide gel electrophoresis, isoelectric focusing, or the like (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)), though the separation and purification method is not limited thereto.

Examples of the chromatography can include affinity chromatography, ion-exchange chromatography, hydrophobic chromatography, gel filtration chromatography, reverse-phase chromatography, and adsorption chromatography.

These chromatography approaches can be carried out using liquid chromatography such as HPLC or FPLC.

Examples of the column for use in the affinity chromatography can include protein A columns and protein G columns.

Examples of the protein A columns can include Hyper D, POROS, and Sepharose F.F. (GE Healthcare Bio-Sciences Corp.).

Also, the antibody may be purified by exploiting its binding activity to the antigen using an antigen-immobilized carrier.

The $K_D$ value that indicates the binding affinity of the anti-ALK2 antibody according to the present invention for ALK2 is preferably $10^{-6}$ M or less, for example, $10^{-7}$ M or less, $10^{-8}$ M or less, $10^{-9}$ M or less, $10^{-10}$ M or less, $10^{-11}$ M or less, or $10^{-12}$ M or less.

4. Pharmaceutical Composition

The present invention provides a pharmaceutical composition comprising at least any one anti-ALK2 antibody or antigen-binding fragment thereof.

The anti-ALK2 antibody of the present invention encompasses, for example, the following antibody or antigen-binding fragment thereof.

An antibody or an antigen-binding fragment thereof which specifically recognizes polypeptides consisting of the following amino acid sequences (a) to (c) and inhibits BMP signal transduction:

(a) an amino acid sequence consisting of amino acid numbers 21 to 123 of the amino acid sequence of SEQ ID NO: 1;

(b) an amino acid sequence consisting of amino acid numbers 21 to 123 of the amino acid sequence of SEQ ID NO: 2; and (c) an amino acid sequence consisting of amino acid numbers 21 to 123 of the amino acid sequence of SEQ ID NO: 3.

The anti-ALK2 antibody is at least one of the following (1) to (7):

(1) an antibody or an antigen-binding fragment thereof in which the heavy chain sequence comprises a variable region comprising CDR sequences consisting of the amino acid sequences of SEQ ID NO: 13 (CDRH1), SEQ ID NO: 14 (CDRH2) and SEQ ID NO: 15 (CDRH3), and the light chain sequence comprises a variable region comprising CDR sequences consisting of the amino acid sequences of SEQ ID NO: 16 (CDRL1), SEQ ID NO: 17 (CDRL2) and SEQ ID NO: 18 (CDRL3);

(2) an antibody comprising a heavy chain variable region sequence consisting of the amino acid sequence of SEQ ID NO: 9 and a light chain variable region sequence consisting of the amino acid sequence of SEQ ID NO: 11, or an antigen-binding fragment thereof;

(3) an antibody or an antigen-binding fragment thereof which cross-competes, for binding to an extracellular region of ALK2 protein, with the antibody or the antigen-binding fragment thereof described in (1) or (2);

(4) an antibody or an antigen-binding fragment thereof which comprises an amino acid sequence having at least 95% identity to any of the amino acid sequences in (1) to (3);

(5) an antibody or an antigen-binding fragment thereof which comprises an amino acid sequence having at least 99% identity to any of the amino acid sequences in (1) to (3);

(6) an antibody or an antigen-binding fragment thereof which comprises an amino acid sequence comprising a substitution(s), a deletion(s), or an addition(s) of one or several amino acid residues in any of the amino acid sequences in (1) to (3); and (7) the antibody or the antigen-binding fragment thereof according to any of (1) to (6) which comprises a modification.

The "modification" in (7) is listed in the section 3. "Anti-ALK2 antibody and production thereof".

Examples of the disease caused by an activating mutation in ALK2 can include fibrodysplasia ossificans progressiva (FOP), progressive osseous heteroplasia (POH), diffuse idiopathic skeletal hyperostosis (DISH), traumatic ectopic ossification, ectopic ossification after implant arthroplasty, diffuse intrinsic pontine glioma (DIPG), spondyloarthritis (SpA), ankylosing spondylitis (AS), anemia, and thinning hair. The disease is preferably fibrodysplasia ossificans progressiva (FOP), progressive osseous heteroplasia (POH), traumatic ectopic ossification, or ectopic ossification after implant arthroplasty, more preferably fibrodysplasia ossificans progressiva (FOP), though the disease is not limited thereto as long as the disease is caused by an activating mutation in ALK2. In FOP patients, finger or toe fusion or deformity, cervical fusion or deformity, or the like is also found, and hearing loss is also manifested. These conditions are also included in the disease caused by an activating mutation in ALK2.

In such diseases, ectopic ossification and/or ossification of tendon and ligament and/or brain tumor is induced by ALK2-mediated BMP signal transduction.

The pharmaceutical composition of the present invention is, for example, a therapeutic and/or prophylactic drug for ectopic ossification and/or ossification of tendon and ligament and/or brain tumor (e.g., diffuse intrinsic pontine glioma (DIPG)).

The "ectopic ossification" means bone formation at a site where the bone is originally absent. The ectopic ossification is preferably fibrodysplasia ossificans progressiva (FOP).

Activating mutations in ALK2 have been confirmed in FOP patients, and 10 or more types of mutations have been reported so far. All of these mutations have been found to be amino acid mutations (missense mutations) present in the intracellular region of the ALK2 protein and do not cause any change in the amino acid sequence of the extracellular region. Thus, use of the anti-ALK2 antibody binding to the extracellular region of ALK2 produces therapeutic and/or prophylactic effects on FOP, without depending on the types of mutations.

The treatment of FOP means cure of FOP symptoms, amelioration of the symptoms, mitigation of the symptoms, or suppression of progression of the symptoms.

The prevention of FOP means avoidance or suppression of onset of flare-up or ectopic ossification.

As used herein, the "brain tumor" can include, for example, diffuse intrinsic pontine glioma (DIPG), brain stem glioma, glioblastoma, glioblastoma multiforme (GBM), non-glioblastoma brain tumor, meningioma, central nervous system lymphoma, glioma, astroglioma, anaplastic astrocytoma, oligodendroglioma, oligoastrocytoma, medulloblastoma, and ependymoma. Diffuse intrinsic pontine glioma (DIPG) is preferred.

Activating mutations in ALK2 have also been confirmed in DIPG patients. R206H, R258G, G328E, G328V, G328W, and G356D mutants are known as mutants of human ALK2. These mutations, except for the G328V mutation, are also common in FOP patients. The anti-ALK2 antibody exhibits ALK2 inhibitory activity except that the G328V mutation is present. Therefore, the anti-ALK2 antibody used in the present invention has therapeutic and/or prophylactic effects on DIPG in a patient having an activating mutation other than G328V mutation in ALK2.

The present invention also provides use of the antibody or the antigen-binding fragment thereof as a therapeutic and/or prophylactic drug for ectopic ossification and/or diffuse intrinsic pontine glioma (DIPG).

The biological activity of ALK2 (BMP signal inhibitory activity) of the anti-ALK2 antibody can be confirmed in vitro, for example, by luciferase assay using reporter plasmids having an insert of a BMP-responsive sequence, SMAD1/5/8 phosphorylation, expression analysis of BMP target genes, or measurement of alkaline phosphatase activity in mouse myoblasts C2C12 induced to differentiate into osteoblasts by stimulation with a BMP ligand.

The culture of myoblasts (C2C12 cells) in the presence of BMP suppresses their differentiation into mature muscle cells through an intracellular signal transduction mechanism specific for BMP and instead induces the differentiation into osteoblasts. Thus, ALK2-mediated BMP signal transduction can be analyzed with models of induction of differentiation of C2C12 cells into osteoblasts by BMP.

The therapeutic or prophylactic effects of the anti-ALK2 antibody on ectopic ossification can be confirmed in vivo using laboratory animals, for example, by subcutaneously or intravenously administering the anti-ALK2 antibody to ectopic ossification-induced models with BMP ligand-containing pellets transplanted to mouse muscle, or FOP mouse models harboring mutated ALK2, and analyzing ectopic bone formation. Alternatively, the therapeutic or prophylactic effects on brain tumor can be confirmed, for example, by subcutaneously or intravenously administering the anti-ALK2 antibody to models prepared by the administration of patient-derived tumor cells to the brain or under the skin of immunodeficient mice, and analyzing tumor growth or survival days of the mice.

The anti-ALK2 antibody used in the present invention can be administered alone or in combination with at least one additional therapeutic drug for ectopic ossification in the treatment or prevention of ectopic ossification, and can be administered alone or in combination with at least one additional therapeutic drug for brain tumor, radiotherapy, immunotherapy or chemotherapy, etc. in the treatment or prevention of brain tumor.

Examples of the additional therapeutic drug for ectopic ossification that can be administered in combination with the anti-ALK2 antibody can include, but are not limited to, anti-inflammatory drugs, steroids, bisphosphonates, muscle relaxants, and retinoic acid receptor (RAR) γ agonists.

Examples of the anti-inflammatory drug can include aspirin, diclofenac, indomethacin, ibuprofen, ketoprofen, naproxen, piroxicam, rofecoxib, celecoxib, azathioprine, penicillamine, methotrexate, sulfasalazine, leflunomide, infliximab, and etanercept. Indomethacin, ibuprofen, piroxicam, or celecoxib is preferred.

Examples of the steroid can include prednisolone, beclomethasone, betamethasone, fluticasone, dexamethasone, and hydrocortisone. Prednisolone is preferred.

Examples of the bisphosphonate can include alendronate, cimadronate, clodronate, etidronate, ibandronate, incadronate, minodronate, neridronate, olpadronate, pamidronate, piridronate, risedronate, tiludronate, and zoledronate. Pamidronate or zoledronate is preferred.

Examples of the muscle relaxant can include cyclobenzaprine, metaxalone, and baclofen. Baclofen is preferred.

Examples of the retinoic acid receptor γ agonist can include palovarotene.

Examples of the additional therapeutic drug for brain tumor that can be administered in combination with the anti-ALK2 antibody can include temozolomide, bevacizumab, carmustine, lomustine, procarbazine hydrochloride, and vincristine.

Depending on the condition of ectopic ossification or brain tumor or the intended degree of treatment and/or prevention, two or three or more additional therapeutic drugs can be administered, and these additional therapeutic drugs may be included in the same preparation and thereby administered at the same time. The additional therapeutic drug and the anti-ALK2 antibody may also be included in the same preparation and thereby administered at the same time. Also, the anti-ALK2 antibody and the additional therapeutic drug may be included in separate preparations and administered at the same time. Alternatively, the additional agent and the anti-ALK2 antibody may be separately administered one after another. Specifically, a therapeutic drug comprising the anti-ALK2 antibody or the antigen-binding fragment thereof as an active ingredient may be administered after administration of the additional therapeutic drug, or the additional therapeutic drug may be administered after administration of the therapeutic drug containing the anti-ALK2 antibody or the antigen-binding fragment thereof as an active ingredient. For administration in gene therapy, a gene for a protein serving as a therapeutic drug for ectopic ossification or brain tumor and the gene for the anti-ALK2 antibody can be inserted at a site downstream of different promoter regions or the same promoter region and can be introduced to different vectors or the same vector.

The anti-ALK2 antibody or the fragment thereof can be conjugated with a therapeutic drug for ectopic ossification or brain tumor to produce a targeted drug conjugate described in M. C. Garnet "Targeted drug conjugates: principles and progress", Advanced Drug Delivery Reviews, (2001) 53, 171-216. For this purpose, an antibody molecule as well as any antibody fragment is applicable unless their ability to bind to ALK 2 (or ALK2-recognizing property) is completely deleted. Examples of the antibody fragment can include fragments such as Fab and $F(ab')_2$. The conjugation manner of the anti-ALK2 antibody or the fragment of the antibody with the therapeutic drug for FOP can take various forms described in, for example, M. C. Garnet "Targeted drug conjugates: principles and progress", Advanced Drug Delivery Reviews, (2001) 53, 171-216, G. T. Hermanson "Bioconjugate Techniques" Academic Press, California (1996), Putnam and J. Kopecek "Polymer Conjugates with Anticancer Activity" Advances in Polymer Science (1995) 122, 55-123. Specific examples thereof can include a manner in which the anti-ALK2 antibody is chemically conjugated with the therapeutic drug for ectopic ossification or brain tumor either directly or via a spacer such as oligopeptide, and a manner in which the anti-ALK2 antibody is conjugated with the therapeutic drug for ectopic ossification or brain tumor via an appropriate drug carrier. Examples of the drug carrier can include drug delivery systems such as liposomes, nanoparticles, nanomicelles, and water-soluble polymers (e.g., X. Yu et al., J Nanomater. 2016; 2016:doi: 10.1155/2016/1087250; and J. Wang et al., Drug Delivery, 25: 1, 1319-1327, D01:10.1080/10717544.2018.1477857). Examples of such a manner via the drug carrier can more specifically include a manner in which the therapeutic drug for ectopic ossification or brain tumor is encapsulated in a liposome and the liposome is conjugated with the antibody, and a manner in which the therapeutic drug for ectopic ossification or brain tumor is chemically conjugated with a water-soluble polymer (a compound having a molecular weight from approximately 1000 to approximately 100,000) either directly or via a spacer such as oligopeptide and the water-soluble polymer is conjugated with the antibody. The conjugation of the antibody (or the fragment) with the therapeutic drug for ectopic ossification or brain tumor or the drug carrier (e.g., a liposome or a water-soluble polymer) can be carried out by a method well known to those skilled in the art, such as a method described in G. T. Hermanson "Bioconjugate Techniques" Academic Press, California (1996), and Putnam and J. Kopecek "Polymer Conjugates with Anticancer Activity" Advances in Polymer Science (1995) 122, 55-123. The encapsulation of the therapeutic drug for ectopic ossification or brain tumor in the liposome can be carried out by a method well known to those skilled in the art, such as a method described in, for example, D. D. Lasic "Liposomes: From Physics to Applications", Elsevier Science Publishers B.V., Amsterdam (1993). The conjugation of the therapeutic drug for ectopic ossification or brain tumor with the water-soluble polymer can be carried out by a method well known to those skilled in the art, such as a method described in D. Putnam and J Kopecek "Polymer Conjugates with Anticancer Activity" Advances in Polymer Science (1995) 122, 55-123. The conjugate of the antibody (or the fragment) with the protein as a therapeutic drug for ectopic ossification or brain tumor (e.g., an antibody or a fragment thereof) can be prepared by any of the methods described above or a genetic engineering method well known to those skilled in the art.

For the administration of the human type anti-ALK2 antibody to a patient, the dose of the anti-ALK2 antibody used in the present invention is, for example, approximately 0.1 to 100 mg/kg body weight, which can be administered once or twice or more per 1 to 180 days. However, the dose and the number of doses should generally be determined in consideration of the sex, body weight, and age of a patient, symptoms, severity, adverse reactions, etc., and therefore, are not limited to the dose or usage described above.

Non-limiting examples of the anti-ALK2 antibody used in the present invention can include injections including intravenous drips, suppositories, transnasal formulations, sublingual formulations, and transdermal absorption formulations. The administration route is an oral administration route or a parenteral administration route. Non-limiting examples of the parenteral administration route include intravenous, intraarterial, intramuscular, intrarectal, transmucosal, intradermal, intraperitoneal, and intraventricular routes.

5. Method for Inhibiting Activation of ALK2 Kinase or BMP Signal Transduction The antibody of the present invention includes an antibody or an antigen-binding fragment thereof having a property of specifically binding to an extracellular region of ALK2 to form an ALK2 homodimer, a property of inhibiting the formation of an ALK2-type II receptor heterodimer, and a property of inhibiting the activation of ALK2 kinase, or an antibody or an antigen-binding fragment thereof having a property of specifically binding to an extracellular region of ALK2 to form an ALK2 homodimer, a property of inhibiting the formation of an ALK2-type II receptor heterodimer, and a property of inhibiting BMP signal transduction.

Such an antibody is based on the new finding that the antibody brings about structural change in BMP receptor (tetramer composed of ALK2 and type II receptor) and thereby inhibit the interaction between ALK2/ACVR1 (type I receptor) and type II receptor, thereby exerting an inhibitory effect on receptor activation. The interaction means that the type II receptor phosphorylates the GS domain of the type I receptor to activate the type I receptor. Thus, the structural change is incomplete (loose) conformational change in the tetramer to an extent that cannot cause the phosphorylation of the GS domain.

Thus, the present invention provides a method for inhibiting the activation of ALK2 kinase in a cell expressing ALK2 on cell surface, characterized by inhibiting the activation using an antibody having a property of specifically binding to an extracellular region of ALK2 to form an ALK2 homodimer, and a property of inhibiting the formation of an ALK2-type II receptor heterodimer.

The present invention also provides a method for inhibiting BMP signal transduction in a cell expressing ALK2 on cell surface, characterized by inhibiting the BMP signal transduction using an antibody having a property of specifically binding to an extracellular region of ALK2 to form an ALK2 homodimer, and a property of inhibiting the formation of an ALK2-type II receptor heterodimer.

The amino acid residue at amino acid number 330 of ALK2 is desirably natural proline for humans. ALK2 may have an activating mutation. Example of the activating mutation of ALK2 can include at least one selected from L196P, delP197_F198insL, R2021, R206H, Q207E, R258S, R258G, G325A, G328E, G328R, G328W, G356D, and R375P. At least one selected from R206H, R258G, G328E, G328W, G356D, and K400E is preferred, and R206H is more preferred. In other words, even if ALK2 is the natural one or has an activating mutation, the antibody of the present invention can inhibit the activation of ALK2 kinase or inhibit BMP signal transduction.

The antibody is preferably a monoclonal antibody or an antigen-binding fragment thereof because of being easily characterized both structurally and biologically.

The monoclonal antibody or the antigen-binding fragment thereof that can be used in the method described above is, for example, at least one antibody or antigen-binding fragment thereof described in the following (1) to (8):

(1) an antibody or an antigen-binding fragment thereof comprising a heavy chain variable region comprising CDRs consisting of the amino acid sequences of SEQ ID NO: 13 (CDRH1), SEQ ID NO: 14 (CDRH2) and SEQ ID NO: 15 (CDRH3), and a light chain variable region comprising CDRs consisting of the amino acid sequences of SEQ ID NO: 16 (CDRL1), SEQ ID NO: 17 (CDRL2) and SEQ ID NO: 18 (CDRL3), or an antibody or an antigen-binding fragment thereof which cross-competes, for binding to an extracellular region of ALK2 protein, with the antibody or the antigen-binding fragment thereof;

(2) an antibody or an antigen-binding fragment thereof comprising a heavy chain variable region comprising CDRs consisting of the amino acid sequences of SEQ ID NO: 29 (CDRH1), SEQ ID NO: 30 (CDRH2) and SEQ ID NO: 31 (CDRH3), and a light chain variable region comprising CDRs consisting of the amino acid sequences of SEQ ID NO: 32 (CDRL1), SEQ ID NO: 33 (CDRL2) and SEQ ID NO: 34 (CDRL3), or an antibody or an antigen-binding fragment thereof which cross-competes, for binding to an extracellular region of ALK2 protein, with the antibody or the antigen-binding fragment thereof;

(3) an antibody or an antigen-binding fragment thereof comprising a heavy chain variable region comprising CDRs consisting of the amino acid sequences of SEQ ID NO: 35 (CDRH1), SEQ ID NO: 36 (CDRH2) and SEQ ID NO: 37 (CDRH3), and a light chain variable region comprising CDRs consisting of the amino acid sequences of SEQ ID NO: 38 (CDRL1), SEQ ID NO: 39 (CDRL2) and SEQ ID NO: 40 (CDRL3), or an antibody or an antigen-binding fragment thereof which cross-competes, for binding to an extracellular region of ALK2 protein, with the antibody or the antigen-binding fragment thereof;

(4) an antibody or an antigen-binding fragment thereof comprising a heavy chain variable region comprising CDRs consisting of the amino acid sequences of SEQ ID NO: 41 (CDRH1), SEQ ID NO: 42 (CDRH2) and SEQ ID NO: 43 (CDRH3), and a light chain variable region comprising CDRs consisting of the amino acid sequences of SEQ ID NO: 44 (CDRL1), SEQ ID NO: 45 (CDRL2) and SEQ ID NO: 46 (CDRL3), or an antibody or an antigen-binding fragment thereof which cross-competes, for binding to an extracellular region of ALK2 protein, with the antibody or the antigen-binding fragment thereof;

(5) an antibody or an antigen-binding fragment thereof comprising a heavy chain variable region comprising CDRs consisting of the amino acid sequences of SEQ ID NO: 47 (CDRH1), SEQ ID NO: 48 (CDRH2) and SEQ ID NO: 49 (CDRH3), and a light chain variable region comprising CDRs consisting of the amino acid sequences of SEQ ID NO: 50 (CDRL1), SEQ ID NO: 51 (CDRL2) and SEQ ID NO: 52 (CDRL3), or an antibody or an antigen-binding fragment thereof which cross-competes, for binding to an extracellular region of ALK2 protein, with the antibody or the antigen-binding fragment thereof;

(6) an antibody or an antigen-binding fragment thereof which comprises an amino acid sequence having at least 95% identity to any of the amino acid sequences in (1) to (5);

(7) an antibody or an antigen-binding fragment thereof which comprises an amino acid sequence having at least 99% identity to any of the amino acid sequences in (1) to (5); and (8) an antibody or an antigen-binding fragment thereof which comprises an amino acid sequence comprising a substitution(s), a deletion(s), or an addition(s) of one or several amino acid residues in any of the amino acid sequences in (1) to (5).

Particular antibodies of (2) to (5) are A2-11E, A2-15A, A2-25C, and A2-27D described by the present inventors in WO2016/121908. These antibodies have a property of forming an ALK2 homodimer (FIG. 7B), and a property of inhibiting the formation of an ALK2-type II receptor heterodimer (FIG. 8B), as in the antibody of (1).

A humanized antibody derived from the A2-15A antibody is included in the antibody used in the present invention as long as the humanized antibody comprises all of the six CDR sequences of A2-15A and has binding activity and cross-linking ability to ALK2, and the ability to inhibit the formation of an ALK2-type II receptor heterodimer. The heavy chain variable region of the A2-15A antibody comprises CDRH1 consisting of the amino acid sequence of SEQ ID NO: 29 (GFTFSHYYMA), CDRH2 consisting of the amino acid sequence of SEQ ID NO: 30 (SITNSGGSINYRDSVKG), and CDRH3 consisting of the amino acid sequence of SEQ ID NO: 31 (EGGENYGGYPPFAY). The light chain variable region of the A2-15A antibody comprises CDRL1 consisting of the amino acid sequence of SEQ ID NO: 32 (RANQGVSLSRYNLMH), CDRL2 consisting of the amino acid sequence of SEQ ID NO: 33 (RSSNLAS), and CDRL3 consisting of the amino acid sequence of SEQ ID NO: 34 (QQSRESPFT). CDRL2 includes CDRL2 consisting of the amino acid sequence of SEQ ID NO: 55 (RSSNLAQ) comprising a substitution of one amino acid in the amino acid sequence of SEQ ID NO: 33. Furthermore, an antibody that competes with the A2-15A antibody for binding to the ALK2 is also included therein.

Actual examples of the humanized antibody derived from the A2-15A antibody can include an antibody consisting of a heavy chain comprising an amino acid sequence consisting of amino acid numbers 20 to 468 of the amino acid sequence of SEQ ID NO: 56 and a light chain comprising an amino acid sequence consisting of amino acid numbers 21 to 238 of the amino acid sequence of SEQ ID NO: 57.

A humanized antibody derived from the A2-27D antibody is included in the antibody used in the present invention as long as the humanized antibody comprises all of the six CDR sequences of A2-27D and has binding activity and cross-linking ability to ALK2, and the ability to inhibit the formation of an ALK2-type II receptor heterodimer. The heavy chain variable region of the A2-27D antibody comprises CDRH1 consisting of the amino acid sequence of SEQ ID NO: 35 (GSTFSNYGMK), CDRH2 consisting of the amino acid sequence of SEQ ID NO: 36 (SISRSSTYIYYADTVKG), and CDRH3 consisting of the amino acid sequence of SEQ ID NO: 37 (AISTPFYWYFDF). The light chain variable region of the A2-27D antibody comprises CDRL1 consisting of the amino acid sequence of SEQ ID NO: 38 (LASSSVSYMT), CDRL2 consisting of the amino acid sequence of SEQ ID NO: 39 (GTSNLAS), and CDRL3 consisting of the amino acid sequence of SEQ ID NO: 40 (LHLTSYPPYT). Furthermore, an antibody that competes with the A2-27D antibody for binding to the ALK2 is also included therein.

Actual examples of the humanized antibody derived from the A2-27D antibody can include an antibody consisting of a heavy chain comprising an amino acid sequence consisting of amino acid numbers 20 to 470 of the amino acid sequence of SEQ ID NO: 58 and a light chain comprising an amino acid sequence consisting of amino acid numbers 21 to 234 of the amino acid sequence of SEQ ID NO: 59, and an antibody consisting of a heavy chain comprising an amino acid sequence consisting of amino acid numbers 20 to 470 of the amino acid sequence of SEQ ID NO: 60 and a light chain comprising an amino acid sequence consisting of amino acid numbers 21 to 234 of the amino acid sequence of SEQ ID NO: 61.

A humanized antibody derived from the A2-11E antibody is included in the antibody used in the present invention as long as the humanized antibody comprises all of the six CDR sequences of A2-11E and has binding activity and cross-linking ability to ALK2, and the ability to inhibit the formation of an ALK2-type II receptor heterodimer. The heavy chain variable region of the A2-11E antibody comprises CDRH1 consisting of the amino acid sequence of SEQ ID NO: 41 (GFTFSNYYMY), CDRH2 consisting of the amino acid sequence of SEQ ID NO: 42 (SINTDGGSTYYPDSVKG), and CDRH3 consisting of the amino acid sequence of SEQ ID NO: 43 (STPNIPLAY). The light chain variable region of the A2-11E antibody comprises CDRL1 consisting of the amino acid sequence of SEQ ID NO: 44 (KASQNIYKYLN), CDRL2 consisting of the amino acid sequence of SEQ ID NO: 45 (YSNSLQT), and CDRL3 consisting of the amino acid sequence of SEQ ID NO: 46 (FQYSSGPT). Furthermore, an antibody that competes with the A2-11E antibody for binding to the ALK2 is also included therein.

A humanized antibody derived from the A2-25C antibody is included in the antibody used in the present invention as long as the humanized antibody comprises all of the six CDR sequences of A2-25C and has binding activity and cross-linking ability to ALK2, and the ability to inhibit the formation of an ALK2-type II receptor heterodimer. The heavy chain variable region of the A2-25C antibody comprises CDRH1 consisting of the amino acid sequence of SEQ ID NO: 47 (GFTFSYYAMS), CDRH2 consisting of the amino acid sequence of SEQ ID NO: 48 (SISRGGDNTYYRDTVKG), and CDRH3 consisting of the amino acid sequence of SEQ ID NO: 49 (LNYNNYFDY). The light chain variable region of the A2-25C antibody comprises CDRL1 consisting of the amino acid sequence of SEQ ID NO: 50 (QASQDIGNWLS), CDRL2 consisting of the amino acid sequence of SEQ ID NO: 51 (GATSLAD), and CDRL3 consisting of the amino acid sequence of SEQ ID NO: 52 (LQAYSAPFT). Furthermore, an antibody that competes with the A2-25C antibody for binding to the ALK2 is also included therein.

6. Composition for Diagnosis

The present invention provides a composition for testing or diagnosis (hereinafter, collectively referred to as a "composition for diagnosis") comprising an anti-ALK2 antibody or an antigen-binding fragment thereof.

The composition for diagnosis of the present invention is useful in the testing or diagnosis of ALK2-related diseases such as FOP or of ALK2 expression. In the present invention, the testing or the diagnosis includes, for example, the determination or measurement of a risk of developing a disease, the determination of the presence or absence of a disease, the measurement of the degree of progression or exacerbation of a disease, the measurement or determination of the effect of drug therapy using the pharmaceutical composition comprising the anti-ALK2 antibody or the like, the measurement or determination of the effect of therapy other than drug therapy, the measurement of a risk of recurrence of a disease, and the determination of the presence or absence of recurrence of a disease. However, the testing or the diagnosis according to the present invention is not limited to these, and any approach can be used.

The composition for diagnosis of the present invention is useful in the identification of a recipient individual for the antibody of the present invention or the antigen-binding fragment thereof, a composition comprising the same, or a pharmaceutical composition comprising the same.

The composition for diagnosis can contain a pH buffer, an osmoregulator, salts, a stabilizer, an antiseptic, a color developer, a sensitizer, an aggregation inhibitor, and the like.

The present invention also provides a method for testing or diagnosing ALK2-related diseases such as FOP, use of the antibody of the present invention for preparing a composition for diagnosis of the diseases, and use of the antibody of the present invention for testing or diagnosing the diseases. The present invention also encompasses a kit for testing or diagnosis comprising the antibody of the present invention.

The desirable testing or diagnosis method involving the antibody of the present invention is sandwich ELISA. Any usual detection method using antibodies, such as ELISA, RIA, enzyme-linked immunospot (ELISPOT) assay, dot blotting, Ouchterlony test, counterimmunoelectrophoresis (CIE), chemiluminescent immunoassay (CLIA), or flow cytometry (FCM), may be used. The antibodies can be labeled by a method using biotin or by any other labeling method that can be performed in biochemical analysis using, for example, a label such as HRP, alkaline phosphatase, a fluorophore (e.g., FITC and ALEXA), or a radioisotope. A chromogenic substrate such as TMB (3,3',5,5'-tetramethylbenzidine), BCIP (5-bromo-4-chloro-3-indolyl phosphate), p-NPP (p-nitrophenyl phosphate), OPD (o-phenylenediamine), ABTS (3-ethylbenzothiazoline-6-sulfonic acid), and SuperSignal ELISA Pico Chemiluminescent Substrate (Thermo Fisher Scientific Inc.), a fluorescent substrate QuantaBlu™ Fluorogenic Peroxidase Substrate (Thermo Fisher Scientific Inc.), and a chemiluminescent substrate can be used in detection using enzymatic labeling. Samples from humans or non-human animals as well as artificially treated samples such as recombinant proteins can be subjected to this assay. Examples of test samples from individual organisms can include, but are not limited to, blood, synovial fluids, ascites, lymph, cerebrospinal fluids, tissue homogenate supernatants, and tissue sections.

The sandwich ELISA kit for testing or diagnosis comprising the antibody of the present invention may comprise a solution of ALK2 protein standards, a coloring reagent, a buffer solution for dilution, an antibody for solid phase, an antibody for detection, and a washing solution, and the like. The amount of the antibody bound to the antigen can be suitably measured by the application of a method such as an absorbance, fluorescence, luminescence, or radioisotope (RI) method. An absorbance plate reader, a fluorescence plate reader, a luminescence plate reader, an RI liquid scintillation counter, or the like is suitably used in the measurement.

The composition for diagnosis, etc. of the present invention can be used not only in these immunohistological tests but in Western blotting or dot blot which involves preparing soluble proteins according to a routine method from cells, tissues, or an organ in a sample, or a portion thereof, and reacting the soluble proteins with a labeled antibody to confirm the presence or absence of ALK2 in the soluble proteins.

The present invention provides an antibody or an antigen-binding fragment thereof useful for immunohistochemistry (IHC) analysis, and a composition comprising the same. Such a composition is also encompassed by the "composition for diagnosis" of the present invention.

The immunohistochemistry is not particularly limited as long as this approach involves reacting a tissue section with an antigen-binding antibody (primary antibody) and detecting the primary antibody bound with the antigen.

The tissue section is suitably fixed in formalin and then treated by paraffin embedding. The tissue section thus paraffin-embedded is sliced and then deparaffinized, followed by antigen activating treatment and nonspecific reaction suppressing treatment. Examples of methods for the antigen activating treatment can include heat treatment and enzymatic treatment with protease. Heat treatment is preferred. The heat treatment is usually performed under suitable conditions involving a temperature of 90 to 110° C., pH 8 to 10, and a treatment time in the range of 20 to 60 minutes. A Tris-EDTA buffer solution (e.g., a 10 mM Tris buffer solution containing 1 mM EDTA) or the like can be used in pH adjustment. A method for inactivating an endogenous enzyme having the same or similar catalytic activity as an enzyme used in color development is usually used as the nonspecific reaction suppressing treatment. For color development through peroxidase reaction, endogenous peroxidase present in tissues is preferably inhibited in advance using $H_2O_2$ or the like. A solvent such as water or methanol can be used for $H_2O_2$. The concentration of $H_2O_2$ is 0.1 to 3%, preferably 0.3 to 3%. The $H_2O_2$ solution can be supplemented with sodium azide. Also, a blocking method using serum or casein can be used as the nonspecific reaction suppressing treatment. Tissues can be treated with serum or casein before the primary antibody reaction. Alternatively, serum or casein may be contained in a solvent for diluting the primary antibody.

The reaction conditions for the primary antibody are not particularly limited and involve a temperature of 4 to 50° C., preferably 20 to 37° C., more preferably 24° C. The reaction time is 5 minutes to all night and all day, preferably 10 minutes to 4 hours, more preferably 30 minutes to 1 hour.

An antibody (secondary antibody) that can be visualized and binds to the primary antibody can be suitably used in the detection of the primary antibody. Where needed, a further reaction may be performed three or more times using an antibody (tertiary antibody) that binds to the secondary antibody itself. A method comprising binding an enzyme such as peroxidase or alkaline phosphatase to the antibody or adding biotin or the like to the antibody and binding thereto streptavidin or the like conjugated with the enzyme, followed by reaction with a chromogenic substrate compatible with the enzyme, can be suitably used as a method for visualizing the secondary antibody or the tertiary antibody. Examples of the method of binding an enzyme to the secondary antibody or the tertiary antibody can include a method using a reagent comprising a dextrin polymer or an amino acid polymer to which multiple molecules of the enzyme and the secondary antibody are attached (polymer method). A chromogenic substrate such as DAB can be used in the method of reacting a biotinylated secondary antibody with peroxidase-labeled streptavidin (LSAB method). Also, a secondary antibody labeled with a fluorescent dye or the like can be used. After treatment with the fluorescently labeled secondary antibody, positive cells are detected using a fluorescence microscope.

A smear method comprises separating isolated cells into cellular components and fluid components by application to glass or centrifugation, and immunostaining the cellular components. Specifically, the cellular components can be applied onto a glass slide, fixed in an ethanol solution, a 10% formalin solution, or the like, and then immunostained in the same way as in the tissue section.

A freeze embedding method comprises embedding isolated tissues in an OCT compound or the like, then rapidly freezing the embedded tissues in liquid nitrogen or the like, and slicing the frozen tissues using a cryostat to prepare a slide preparation. This preparation can be fixed in a 10% formalin solution, an ethanol solution, or the like and then immunostained in the same way as in the tissue section.

The immunohistochemistry procedure can be performed automatically using an immunological apparatus programmed with a reaction solution, reaction conditions, the number of washing runs, etc.

For diagnostic imaging, an antibody is labeled with a pharmaceutically acceptable radionuclide or luminescent material and administered to a test subject, and images can be taken using a diagnostic imaging technique such as PET/CT to determine or test the presence of ALK2.

The antibody or the antigen-binding fragment thereof contained in the composition for diagnosis of the present invention is preferably an antibody that binds to or recognizes ALK2, i.e., an antibody having ALK2 selectivity, or an antigen-binding fragment thereof.

The antibody having ALK2 selectivity is, for example, at least one of the following:

(1) an antibody or an antigen-binding fragment thereof in which the heavy chain sequence comprises a variable region comprising CDR sequences consisting of the amino acid sequences of SEQ ID NO: 13 (CDRH1), SEQ ID NO: 14 (CDRH2) and SEQ ID NO: 15 (CDRH3), and the light chain sequence comprises a variable region comprising CDR sequences consisting of the amino acid sequences of SEQ ID NO: 16 (CDRL1), SEQ ID NO: 17 (CDRL2) and SEQ ID NO: 18 (CDRL3);

(2) an antibody comprising a heavy chain variable region sequence consisting of the amino acid sequence of SEQ ID NO: 9 and a light chain variable region sequence consisting of the amino acid sequence of SEQ ID NO: 11, or an antigen-binding fragment thereof;

(3) an antibody or an antigen-binding fragment thereof which cross-competes, for binding to an extracellular region of ALK2 protein, with the antibody or the antigen-binding fragment thereof described in (1) or (2);

(4) an antibody or an antigen-binding fragment thereof having binding activity to ALK2 protein, where the antibody or the fragment is: an antibody or an antigen-binding fragment thereof in which the heavy chain sequence comprises a variable region comprising CDR sequences consisting of the amino acid sequences of SEQ ID NO: 23 (CDRH1), SEQ ID NO: 24 (CDRH2) and SEQ ID NO: 25 (CDRH3), and the light chain sequence comprises a variable region comprising CDR sequences consisting of the amino acid sequences of SEQ ID NO: 26 (CDRL1), SEQ ID NO: 27 (CDRL2) and SEQ ID NO: 28 (CDRL3); or an antibody or an antigen-binding fragment thereof which cross-competes, for binding to an extracellular region of the ALK2 protein, with the antibody or the antigen-binding fragment;

(5) an antibody consisting of a heavy chain comprising a heavy chain variable region sequence consisting of the amino acid sequence of SEQ ID NO: 19 and a light chain comprising a light chain variable region sequence consisting of the amino acid sequence of SEQ ID NO: 21, or an antigen-binding fragment thereof, or an antibody or an antigen-binding fragment thereof which cross-competes, for binding to an extracellular region of the ALK2 protein, with the antibody or the antigen-binding fragment;

(6) an antibody or an antigen-binding fragment thereof which comprises an amino acid sequence having at least 95% identity to any of the amino acid sequences in (1) to (5);

(7) an antibody or an antigen-binding fragment thereof which comprises an amino acid sequence having at least 99% identity to any of the amino acid sequences in (1) to (5); and (8) an antibody or an antigen-binding fragment thereof which comprises an amino acid sequence comprising a substitution(s), a deletion(s), or an addition(s) of one or several amino acid residues in any of the amino acid sequences in (1) to (5).

In a preferred aspect of the present invention, the composition for diagnosis is for ALK2 detection or measurement.

7. Other Use of Antibody

In the present invention, other use is use of the anti-ALK2 antibody of the present invention or the antigen-binding fragment thereof as a phosphorylation inhibitor for SMAD1, SMAD5 and/or SMAD8.

The phosphorylation of the transcriptional factors SMAD1, SMAD5 and/or SMAD8 activates BMP signal transduction into cells. The phosphorylation inhibitor for SMAD1, SMAD5 and/or SMAD8 can be used, for example, for preparing cells that are induced by differentiation from pluripotent cells and are useful in regenerative medicine (e.g., retinal pigment epithelial cells) (WO2015/087231).

The antibody or the antigen-binding fragment thereof is, for example, at least one of the following:

(1) an antibody or an antigen-binding fragment thereof which specifically recognizes polypeptides consisting of the following amino acid sequences (a) to (c) and inhibits BMP signal transduction:

(a) an amino acid sequence consisting of amino acid numbers 21 to 123 of the amino acid sequence of SEQ ID NO: 1;

(b) an amino acid sequence consisting of amino acid numbers 21 to 123 of the amino acid sequence of SEQ ID NO: 2; and (c) an amino acid sequence consisting of amino acid numbers 21 to 123 of the amino acid sequence of SEQ ID NO: 3;

(2) an antibody or an antigen-binding fragment thereof in which the heavy chain sequence comprises a variable region comprising CDR sequences consisting of the amino acid sequences of SEQ ID NO: 13 (CDRH1), SEQ ID NO: 14 (CDRH2) and SEQ ID NO: 15 (CDRH3), and the light chain sequence comprises a variable region comprising CDR sequences consisting of the amino acid sequences of SEQ ID NO: 16 (CDRL1), SEQ ID NO: 17 (CDRL2) and SEQ ID NO: 18 (CDRL3), or an antibody or an antigen-binding fragment thereof which cross-competes, for binding to an extracellular region of ALK2 protein, with the antibody or the antigen-binding fragment thereof;

(3) an antibody comprising a heavy chain variable region sequence consisting of the amino acid sequence of SEQ ID NO: 9 and a light chain variable region sequence consisting of the amino acid sequence of SEQ ID NO: 11, or an antigen-binding fragment thereof, or an antibody or an antigen-binding fragment thereof which cross-competes, for binding to an extracellular region of ALK2 protein, with the antibody or the antigen-binding fragment thereof;

(4) an antibody comprising a heavy chain variable region comprising CDRs consisting of the amino acid sequences of SEQ ID NO: 29 (CDRH1), SEQ ID NO: 30 (CDRH2) and SEQ ID NO: 31 (CDRH3), and a light chain variable region comprising CDRs consisting of the amino acid sequences of SEQ ID NO: 32 (CDRL1), SEQ ID NO: 33 (CDRL2) and SEQ ID NO: 34 (CDRL3), or an antigen-binding fragment thereof, or an antibody or an antigen-binding fragment thereof which cross-competes, for binding to an extracellular region of ALK2 protein, with the antibody or the antigen-binding fragment thereof;

(5) an antibody comprising a heavy chain variable region comprising CDRs consisting of the amino acid sequences of SEQ ID NO: 35 (CDRH1), SEQ ID NO: 36 (CDRH2) and SEQ ID NO: 37 (CDRH3), and a light chain variable region comprising CDRs consisting of the amino acid sequences of SEQ ID NO: 38 (CDRL1), SEQ ID NO: 39 (CDRL2) and SEQ ID NO: 40 (CDRL3), or an antigen-binding fragment thereof, or an antibody or an antigen-binding fragment thereof which cross-competes, for binding to an extracellular region of ALK2 protein, with the antibody or the antigen-binding fragment thereof;

(6) an antibody comprising a heavy chain variable region comprising CDRs consisting of the amino acid sequences of SEQ ID NO: 41 (CDRH1), SEQ ID NO: 42 (CDRH2) and SEQ ID NO: 43 (CDRH3), and a light chain variable region comprising CDRs consisting of the amino acid sequences of SEQ ID NO: 44 (CDRL1), SEQ ID NO: 45 (CDRL2) and SEQ ID NO: 46 (CDRL3), or an antigen-binding fragment thereof, or an antibody or an antigen-binding fragment thereof which cross-competes, for binding to an extracellular region of ALK2 protein, with the antibody or the antigen-binding fragment thereof;

(7) an antibody comprising a heavy chain variable region comprising CDRs consisting of the amino acid sequences of SEQ ID NO: 47 (CDRH1), SEQ ID NO: 48 (CDRH2) and SEQ ID NO: 49 (CDRH3), and a light chain variable region comprising CDRs consisting of the amino acid sequences of SEQ ID NO: 50 (CDRL1), SEQ ID NO: 51 (CDRL2) and SEQ ID NO: 52 (CDRL3), or an antigen-binding fragment thereof, or an antibody or an antigen-binding fragment thereof which cross-competes, for binding to an extracellular region of ALK2 protein, with the antibody or the antigen-binding fragment thereof;

(8) an antibody or an antigen-binding fragment thereof which comprises an amino acid sequence having at least 95% identity to any of the amino acid sequences in (1) to (7);

(9) an antibody or an antigen-binding fragment thereof which comprises an amino acid sequence having at least 99% identity to any of the amino acid sequences in (1) to (7); and

(10) an antibody or an antigen-binding fragment thereof which comprises an amino acid sequence comprising a substitution(s), a deletion(s), or an addition(s) of one or several amino acid residues in any of the amino acid sequences in (1) to (7).

EXAMPLES

Hereinafter, the present invention will be described further specifically with reference to Examples. However, the scope of the present invention is not limited by these Examples.

[Example 1] Preparation of Rat Anti-Human ALK2 Antibodies (#109 and #200)

1)-1 Preparation of an Antigen

Human ALK2-His (Cat. #10227-H088) from Sino Biological Inc. was used as human ALK2-His, which is the antigen.

1)-2 Immunization of Animals

One (1) mg/mL of human ALK2-His was mixed with an equal volume of TiterMaxGold (TiterMax, USA) to prepare an emulsion. To two 6-week-old Wister female rats, 100 μg per animal of the antigen was subcutaneously administered with the adjuvant in two divided doses. After 1 to 2 weeks, 40 μg of only the antigen solution was subcutaneously administered, and after 3 days, spleen cells and various lymph glands were aseptically removed as antibody-producing cells, and subjected to the following cell fusion.

1)-3 Cell Fusion with Myeloma Cells

The above-described antibody-producing cells were mixed with a myeloma cell line (P3U1 cells) derived from BALB/c mice at a ratio of 5:1 to 10:1, and fused for 3 minutes using 50% polyethylene glycol 1500, and then diluted over 6 minutes. The fused cells were seeded with feeder cells (thymocytes) into ten 96-well plates per animal. The cells were cultured in 15% FBS-containing RPMI1640 medium (containing glutamine, pyruvic acid, penicillin, and streptomycin) containing HAT supplement.

1)-4 Selection of Hybridomas

One week after the cell fusion, using each culture supernatant, clones recognizing human ALK2-His used as the antigen were selected by the enzyme-linked immunosorbent assay (ELISA), and clones recognizing human ALK1-His (Sino Biological Inc.) were excluded. ELISA was performed as follows.

First, the antigen diluted to 1 μg/ml with PBS was immobilized onto a 96-well ELISA plate (NUNC, Cat. #442404) for 2 hours at room temperature or overnight at 4° C. The immobilized solution was removed, and the plate was blocked with a 0.5% skim milk solution dissolved in PBS for 30 minutes at room temperature. Next, the above-described culture supernatant of hybridomas was added, and the plate was left for 1 hour at room temperature. After the plate was washed, an ALP-labeled anti-rat IgG antibody (SAB, Inc.) diluted with a 0.5% skim milk solution to 1:2500 was added, and the plate was further left for 1 hour at room temperature. After the plate was washed, a phenyl phosphate substrate was reacted at room temperature, and then absorbance at a wavelength of 492 nm was measured.

Selected hybridomas were cloned twice or more by limiting dilution. Through the above-described operations, hybridoma cell lines producing monoclonal antibodies #109 and #200 were isolated.

[Example 2] Nucleotide Sequencing of cDNAs Encoding Variable Regions of Rat Anti-Human ALK2 Antibodies (#109 and #200)

1)-1 Nucleotide Sequencing of cDNAs Encoding Variable Regions of Clone #109 or #200

1)-1-1 Preparation of Total RNA from Hybridomas Producing Clone #109 or #200

To amplify cDNAs containing variable regions of clone #109 or #200, total RNA was prepared from the hybridomas producing clone #109 or #200, using Direct-zol RNA Miniprep kit (ZYMO RESEARCH Corp.).

1)-1-2 Amplification by 5'-RACE PCR and Sequencing of cDNA Containing a Light Chain Variable Region of Clone #109 or #200

The following reaction was performed using SMARTer RACE 5'/3' Kit (CLONTECH LABORATORIES, INC.).

The 1st strand cDNA was synthesized from the total RNA by the SMARTer method. Then, a PCR product containing the light chain variable region of clone #109 or #200 was obtained by 5'-RACE PCR using the following primers in combination and the synthesized cDNA as a template. The primers used were oligonucleotides having the sequences of UPM (included in 10× Universal Primer A Mix, SMARTer RACE 5'/3' Kit) and 5'-GATTACGC-CAAGCTTTCAGTAACACTGTCCAGGACACCATCTC-3' (Inf-RKRS) (SEQ ID NO: 53). Inf-RKRS was designed from the sequence of a rat light chain constant region on a database. The sequence analysis of each PCR product thus obtained was performed. Inf-RKRS was used as a sequence primer.

In-Fusion cloning (included in SMARTer RACE 5'/3' Kit) was performed using the PCR product obtained by 5'-RACE PCR. The sequence analysis of the nucleotide sequence of the cloned cDNA containing the light chain variable region was performed. M13-Forward and Inf-RKRS were used as sequence primers. As a result, the same sequence as that of the variable region obtained by 5'-RACE PCR was able to be confirmed.

The determined nucleotide sequences of the light chain variable regions of #109 and #200 are shown in SEQ ID NOs: 22 and 12, respectively, in the Sequence Listing, and the amino acid sequences are shown in SEQ ID NOs: 21 and 11, respectively, in the Sequence Listing.

1)-1-3 Amplification by 5'-RACE PCR and Sequencing of cDNA Containing a Heavy Chain Variable Region of Clone #109 or #200

The following reaction was performed using SMARTer RACE 5'/3' Kit (CLONTECH LABORATORIES, INC.).

The 1st strand cDNA was synthesized from the total RNA by the SMARTer method. Then, a PCR product containing the heavy chain variable region of clone #109 or #200 was obtained by 5'-RACE PCR using the following primers in combination and the synthesized cDNA as a template. The primers used were oligonucleotides having the sequences of UPM (included in 10× Universal Primer A Mix, SMARTer RACE 5'/3' Kit) and 5'-GATTACGC-CAAGCTTCTCCAGAGTTCCAGGT-CACGGTGACTGGC-3' (Inf-RG2AR3) (SEQ ID NO: 54). Inf-RKRS was designed from the sequence of a rat heavy chain constant region on a database. The sequence analysis of each PCR product thus obtained was performed. Inf-RG2AR3 was used as a sequence primer.

In-Fusion cloning (included in SMARTer RACE 5'/3' Kit) was performed using the PCR product obtained by 5'-RACE PCR. The sequence analysis of the nucleotide sequence of the cloned cDNA containing the light chain variable region was performed. M13-Forward and Inf-RG2AR3 were used as sequence primers. As a result, the same sequence as that of the variable region obtained by 5'-RACE PCR was able to be confirmed.

The determined nucleotide sequences of the heavy chain variable regions of #109 and #200 are shown in SEQ ID NOs: 20 and 10, respectively, in the Sequence Listing, and the amino acid sequences are shown in SEQ ID NOs: 19 and 9, respectively, in the Sequence Listing.

The nucleotide sequences encoding the heavy chain variable regions and the light chain variable regions of the rat anti-human ALK2 antibodies #109 and #200 and the amino acid sequences are as described below. The underlines represent CDR1, CDR2, and CDR3 in order from the N-terminal side in each sequence. The CDR sequences were determined by the definition of Abm.

Amino Acid Sequence of the Heavy Chain Variable Region of Clone #109 (SEQ ID NO: 19):

[Formula 1]
EVQLVESGGDLVQPGRSMKLSCAASGFTFSNYGMA

WVRQAPTKGLEWVATISYDGSGTYYRDSVEGRFTI

SRDNAKITLYLQMNSLRSEDTATYYCTRHGYSRVP

YFDYVVGQGVMVTVSS

Amino Acid Sequence of the Light Chain Variable Region of Clone #109 (SEQ ID NO: 21):

[Formula 2]
NIVLTQSPATLSVTPGESVSLSCRASQSISTNIHW

YQQKSNESPRLLIKYASQSISGIPSRFSGSGSGTD

FTLTINRVESEDFSIYYCQQSYSSQLTFGSGTKLE

IKR

Nucleotide Sequence of cDNA Encoding the Heavy Chain Variable Region of Clone #109 (SEQ ID NO: 20):

```
[Formula 3]
GAGGTGCAGCTGGTAGAGTCTGGGGGCGATTTAGT
GCAGCCTGGAAGGTCCATGAAACTCTCCTGTGCAG
CCTCAGGATTCACTTTCAGTAACTATGGCATGGCC
TGGGTCCGCCAGGCTCCAACGAAGGGCCTGGAGTG
GGTTGCAACCATTAGTTATGATGGTAGTGGCACTT
ACTATCGAGACTCCGTGGAGGGCCGATTCACTATC
TCCAGGGATAATGCAAAAATCACCCTATACCTGCA
AATGAACAGTCTGAGGTCTGAGGACACGGCCACTT
ATTACTGTACAAGACACGGCTATAGCAGAGTCCCT
TACTTTGATTACTGGGGCCAAGGAGTCATGGTCAC
AGTCTCCTCA
```

Nucleotide Sequence of cDNA Encoding the Light Chain Variable Region of Clone #109 (SEQ ID NO: 22):

```
[Formula 4]
AACATTGTGTTGACTCAGTCTCCAGCCACCCTGTC
TGTGACTCCAGGAGAGAGTGTCAGTCTCTCCTGCA
GGGCCAGTCAGAGTATTAGCACAAACATACATTGG
TATCAGCAAAAATCAAATGAGTCTCCAAGGCTTCT
CATCAAATATGCTTCCCAGTCCATCTCTGGAATCC
CCTCCAGGTTCAGTGGCAGCGGATCCGGGACAGAT
TTCACTCTCACTATCAACAGAGTAGAGTCTGAAGA
TTTTTCAATTTATTACTGTCAACAGAGTTACAGCA
GCCAGCTCACGTTCGGTTCTGGGACCAAGCTGGAG
ATCAAACGG
```

Amino Acid Sequence of the Heavy Chain Variable Region of Clone #200 (SEQ ID NO: 9):

```
[Formula 5]
QVKLLQSGAALVKPGDSIRMSCKASGYTFTDYIIHWVKQSHGKSLEWIG
YINPYSGGTNYNEKFKSKATLTVDKSSSTAYMEFCRLTSEDSAIYYCVR
RGHDGTGFDYWGQGVMVTVSS
```

Amino Acid Sequence of the Light Chain Variable Region of Clone #200 (SEQ ID NO: 11):

```
[Formula 6]
DVVMTQTPVSLPVSLGGQASISCRSSQSLVHSNGE
TYLHWYLQKPGQSPQLLIYRVSNRFSGVPDRFSGS
GSGTDFTLKLSRVEPEDLGDYYCLQSTHLPLTFGS
GTKLEIKR
```

Nucleotide Sequence of cDNA Encoding the Heavy Chain Variable Region of Clone #200 (SEQ ID NO: 10):

```
[Formula 7]
CAGGTCAAGCTGCTGCAGTCTGGGGCTGCACTGGT
GAAGCCTGGGGACTCTATAAGGATGTCTTGCAAAG
CTTCTGGTTATACATTCACTGACTACATTATACAC
TGGGTGAAGCAGAGTCATGGAAAGAGCCTTGAGTG
GATTGGTTATATTAATCCTTACAGTGGTGGTACTA
ACTACAATGAAAAGTTCAAGAGCAAGGCCACATTG
ACTGTAGACAAATCCAGCAGCACAGCCTATATGGA
GTTTTGCAGATTGACATCTGAGGATTCTGCAATCT
ATTACTGTGTAAGAAGGGGACATGATGGCACCGGC
TTTGATTACTGGGGCCAAGGAGTCATGGTCACAGT
CTCCTCA
```

Nucleotide Sequence of cDNA Encoding the Light Chain Variable Region of Clone #200 (SEQ ID NO: 12):

```
[Formula 8]
GATGTTGTGATGACACAAACTCCAGTCTCCCTGCC
TGTCAGCCTTGGAGGTCAAGCCTCTATCTCTTGCC
GGTCAAGTCAGAGCCTGGTACACAGTAATGGAGAA
ACCTACTTGCATTGGTACCTGCAGAAGCCAGGCCA
GTCTCCACAGCTCCTCATCTATCGGGTTTCCAACA
GATTTTCTGGGGTGCCAGACAGGTTCAGTGGCAGT
GGGTCAGGGACAGATTTCACCCTCAAGCTCAGCAG
AGTAGAGCCTGAGGACTTGGGAGATTATTACTGCT
TACAAAGTACACATTTGCCGCTCACGTTCGGTTCT
GGGACCAAGCTGGAGATCAAACGG
```

[Example 3] BMP Signaling Inhibitory Activity of Rat Anti-Human ALK2 Antibodies (#109 and #200) (Human, Mouse and Rat ALK2)

The ALK2-mediated intracellular signaling inhibitory activity of each of the monoclonal antibodies was analyzed using a BMP-specific luciferase reporter. HEK293A cells were seeded into a 96-well white plate for luciferase assay (manufactured by Greiner Bio-One International GmbH) at $1\times10^4$ cells/well, and cultured overnight in 10% FBS-containing DMEM medium under the conditions of 5% $CO_2$ at 37° C. On the following day, the HEPG2 cells were transfected with pcDEF3/human ALK2(WT)-VS-His, pcDEF3/mouse ALK2(WT)-V5-His, or pcDEF3/rat ALK2(WT)-VS-His, pGL4.26/1dlWT4F-luc (Genes Cells, 7, 949 (2002); Biochem Biophys Res Commun, 407, 213 (2011)), and phRL-SV40 (manufactured by Promega Corp.), using Lipofectamine 2000 (manufactured by Thermo Fisher Scientific Inc.). After 2.5 hours, the medium was replaced with OPTI-MEM I (manufactured by Thermo Fisher Scientific Inc.) containing the monoclonal antibody and 10 ng/mL BMP7 (manufactured by Miltenyi Biotec Inc.), and the cells were further cultured overnight. On the following day, the Firefly and *Renilla* luciferase activity was measured with the plate reader GENios (manufactured by TECAN TRADING AG), using Dual-Glo Luciferase Assay System (manufactured by Promega Corp.).

The results are shown in FIG. 1. Each antibody rarely influenced luciferase activity in the absence of BMP7 (open columns) and inhibited luciferase activity induced in a manner dependent on 10 ng/ml BMP7 (filled columns) as follows. The monoclonal antibody produced by the hybridoma #200 inhibited BMP-specific luciferase activity in HEK293A cells overexpressing human ALK2 and mouse ALK2, as in monoclonal antibodies produced by hybridomas A2-11E, A2-15A, A2-25C, and A2-27D. Unlike monoclonal antibodies produced by hybridomas A2-11E, A2-15A, A2-25C, and A2-27D, the monoclonal antibody produced by the hybridoma #200 also inhibited the BMP-specific luciferase activity of rat ALK2. On the other hand, the monoclonal antibody produced by the hybridoma #109 rarely inhibited human, mouse, and rat ALK2. These results demonstrated that the monoclonal antibody produced by the hybridoma #200 is an antibody that binds to human, mouse, and rat ALK2 and inhibits BMP-mediated intracellular signals.

[Example 4] Test on Influence of Amino Acid Substitution at the Amino Acid Number 64 (Sequence Comparison Among Human, Monkey, Dog, Rat, and Mouse)

Figure 3:
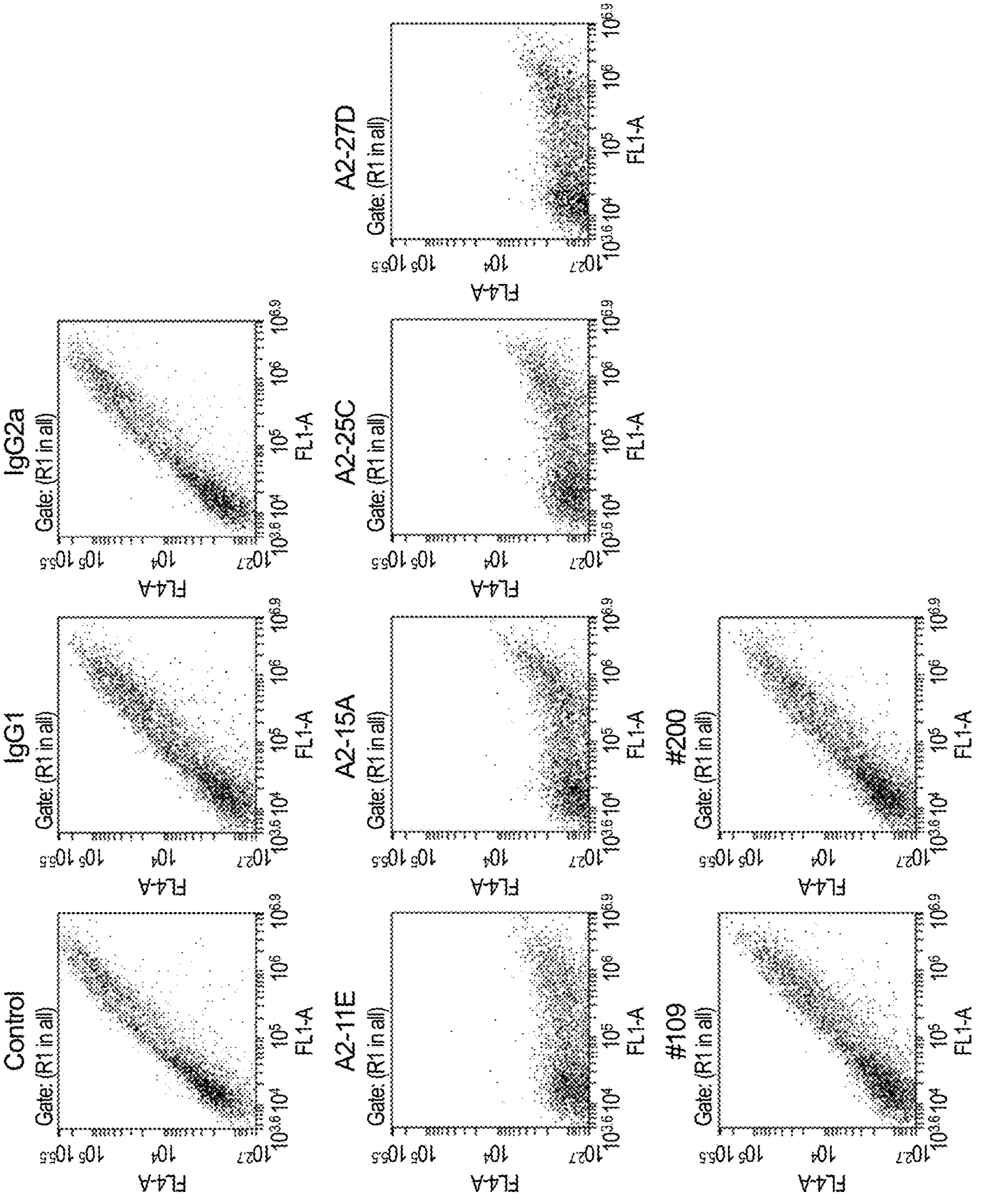
FIG. 3 This figure shows overlap analysis results of epitopes for various rat anti-human ALK2 antibodies relative to an epitope for antibody A2-27D. The antibodies are IgG1, IgG2a, A2-11E, A2-15A, A2-25C, A2-27D, #109, and #200. The figure shows that sites of an ALK2 extracellular region that are bound by the antibodies produced by the hybridomas A2-11E, A2-15A, and A2-25C overlap with a site that is bound by the hybridoma A2-27D, and shows that the antibodies produced by the hybridomas #109 and #200 bind to an extracellular region of ALK2 at a position different from that for A2-27D.

The monoclonal antibody produced by the hybridoma A2-27D was analyzed for its important amino acid residue for inhibiting BMP signals. FIG. 3 shows amino acid sequences (from amino acid numbers 1 to 140) comprising the extracellular regions of human ALK2 (GenBank NM_001104537), monkey ALK2 (GenBank XP_014965630), dog ALK2 (GenBank XM_549615), rat ALK2 (GenBank NP_077812), and mouse ALK2 (GenBank NP_001103674). In these ALK2 after cleavage of the signal peptide (from amino acid numbers 1 to 20), E25, V59, R64, V103, R106, and 5117 were identified as amino acid residues specific for rat ALK2. Expression vectors harboring any one residue of amino acid substitutions K25E, I59V, H64R, I103V, Q106R, and T117S specific for rat ALK2 were constructed using pcDEF3/human ALK2-V5-His as a template, and expression vectors harboring R64H mutation corresponding to human, monkey, dog, or mouse ALK2 were constructed using pcDEF3/rat ALK2-V5-His as a template. In the same manner as in Example 3, HEK293A cells seeded on the previous day were transfected with each of these ALK2 expression vectors and a luciferase reporter plasmid, using Lipofectamine 2000, and the effect of each antibody on BMP-specific luciferase activity induced by BMP7 was measured.

Figure 2:
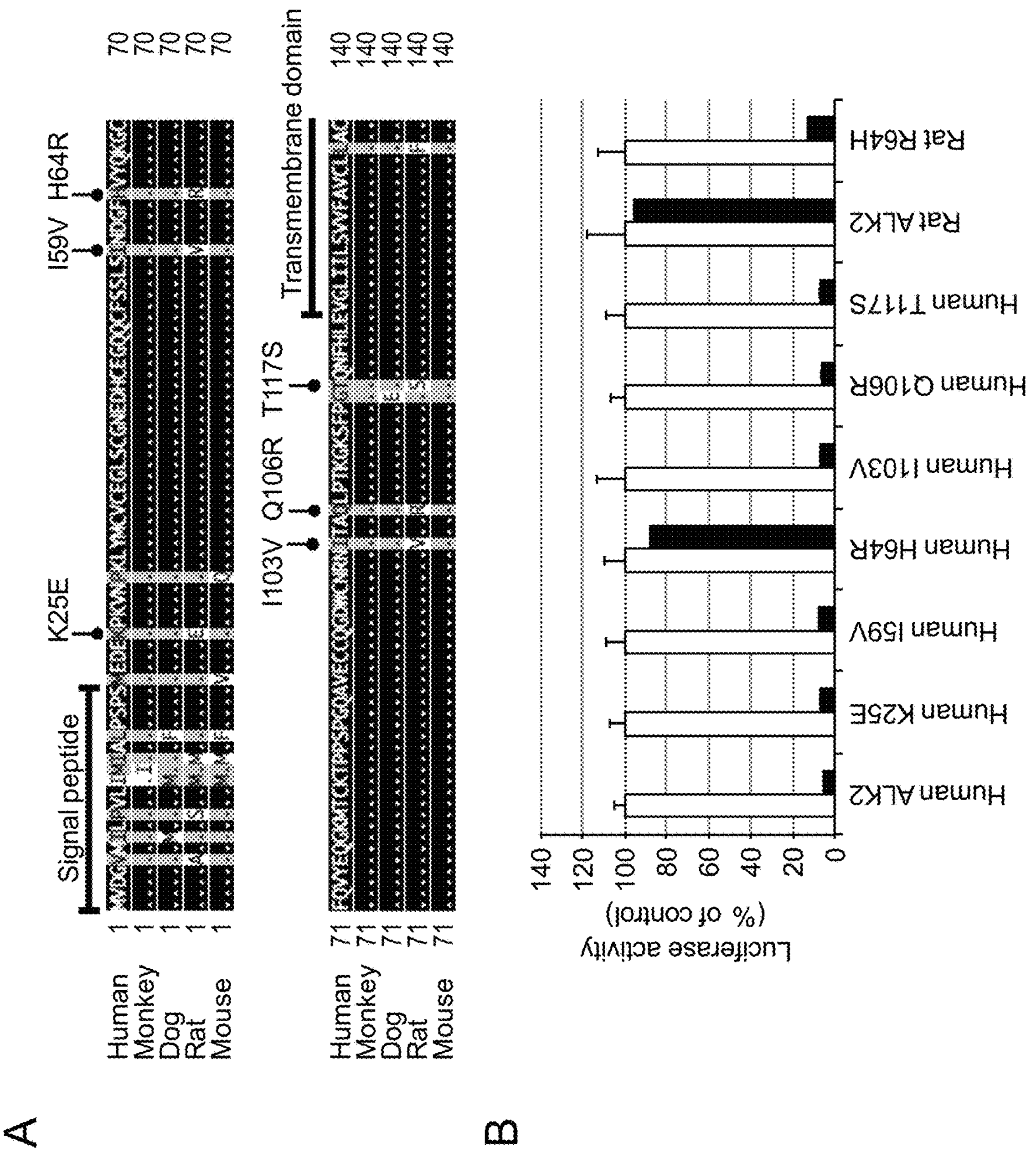
FIG. 2 This figure shows the sequence comparison of the amino acid numbers 1 to 140 of ALK2 among a human, a monkey, a dog, a rat and a mouse (SEQ ID NOs: 4 to 8, respectively; (A)) and the influence of an amino acid substitution at the amino acid number 64 of ALK2 on the BMP signaling inhibitory activity of antibody A2-27D (B). A control antibody is IgG2a. The BMP signal activity was measured using a BMP-specific luciferase reporter.

The results are shown in FIG. 2. The luciferase activity of each ALK2 is indicated by relative activity when the monoclonal antibody produced by the hybridoma A2-D27 was added (filled columns) to the activity when control IgG2a was added (open columns). The monoclonal antibody produced by the hybridoma A2-D27 inhibited BMP intracellular signals activating each human ALK2 harboring any one of the K25E, I59V, I103V, Q106R, and T117S mutations. On the other hand, the antibody did not inhibit BMP signals activating rat wild-type ALK2 or human ALK2 harboring the H64R mutation. However, when the R64H mutation was introduced to rat ALK2, the antibody inhibited BMP signals. These results demonstrated that histidine at the amino acid number 64 (H64) in the extracellular region is important for inhibiting the intracellular signals of ALK2 by the monoclonal antibody produced by the hybridoma A2-27D.

[Example 5] Overlap Analysis of Epitopes for Rat Anti-Human ALK2 Antibodies (#109 and #200)

In the same manner as in Example 3, HEK293A cells were transiently transfected with pcDEF3/human ALK2-EGFP using Lipofectamine 2000 (manufactured by Thermo Fisher Scientific Inc.). After 2.5 hours, the medium was replaced with fresh 10% FBS-containing DMEM medium, and the cells were cultured overnight. On the following day, 1004 each of the cell suspensions adjusted to $1\times10^6$ cells/mL was dispensed into a 1.5-mL microfuge and centrifuged at 500 g for 5 minutes, and then the supernatant was removed. To the cells, 100 µL of a mixed solution of Alexa fluor 647-labeled A2-27D diluted to 1 µg/mL and 10 µg/mL purified IgG was added, and the cells were left for 30 minutes at 4° C. After the cells were washed with PBS three times, fluorescence was detected by a flow cytometer (BD Accuri C6; manufactured by BD Biosciences). The intensity of EGFP expressed by the cells and the fluorescence intensity of stained Alexa flour 647 were plotted.

The results are shown in FIG. 3. Purified IgG1 and IgG2a serving as controls did not inhibit the binding of fluorescently labeled A2-27D to ALK2, whereas the rat anti-ALK2 antibodies produced by the hybridomas A2-11E, A2-15A, A2-25C, and A2-27D each inhibited the binding of fluorescently labeled A2-27D to ALK2. On the other hand, the antibodies produced by the hybridomas #109 and #200 did not inhibit the binding of fluorescently labeled A2-27D to ALK2. These results show that sites of the ALK2 extracellular region that are bound by the antibodies produced by the hybridomas A2-11E, A2-15A, and A2-25C overlap with a site that is bound by the hybridoma A2-27D. On the other hand, it was found that the antibodies produced by the hybridomas #109 and #200 bind to the extracellular region of ALK2 at a position different from that for A2-27D.

[Example 6] Western Blot Analysis with Rat Anti-Human ALK2 Antibody (#109)

In the same manner as in Example 3, HEK293A cells were transiently transfected with each of pcDEF3, pcDEF3/human ALK2(WT)-V5-His, pcDEF3/mouse ALK2(WT)-V5-His, and pcDEF3/rat ALK2(WT)-V5-His, using Lipofectamine 2000. After 2.5 hours, the medium was replaced with fresh 10% FBS-containing DMEM medium, and the cells were cultured overnight. On the following day, cell extracts were prepared, reduced or denatured, and then fractionated using 7% polyacrylamide gel, followed by transfer to a PVDF membrane for Western blot (J Biol Chem, 285, 15577 (2010); and Sci Rep, 4, 7596 (2014)). The primary antibodies used were an anti-VS tag antibody (manufactured by Cell Signaling Technology, Inc., Cat. #13202), an anti-tubulin antibody (manufactured by Cell Signaling Technology, Inc., Cat. #2144), and the rat anti-ALK2 antibodies produced by the hybridomas #109, A2-11E, A2-15A, A2-25C, and A2-27D (10 µg/ml). The secondary antibodies used were a HRP-conjugated anti-rabbit IgG antibody (manufactured by Cell Signaling Technology, Inc., Cat. #7074) fort the anti-V5 tag antibody and the anti-tubulin antibody, and a HRP-conjugated anti-rat IgG antibody (manufactured by Cell Signaling Technology, Inc., Cat. #7077) for the rat anti-ALK2 antibodies.

Figure 4:
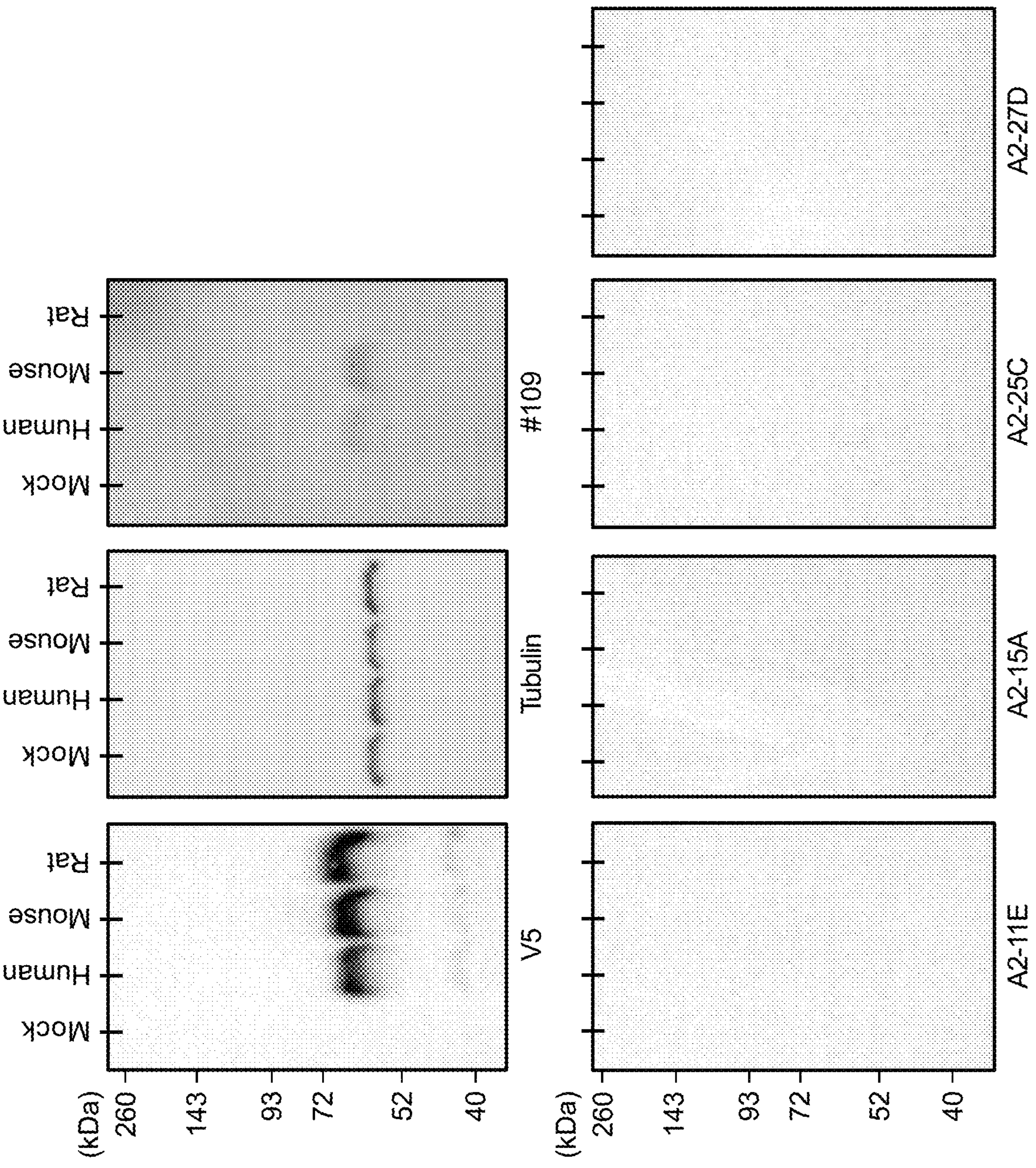
FIG. 4 This figure shows Western blot analysis results of ALK2 using various rat anti-ALK2 antibodies. The antibodies are A2-15A, A2-25C, A2-27D, A2-11E, and #109. The anti-ALK2 monoclonal antibody produced by the hybridoma #109 detected human ALK2 and mouse ALK2 of approximately 65 kDa, whereas the other antibodies did not detect any of the human and mouse ALK2.

The results are shown in FIG. 4. Human, mouse, and rat ALK2 was detected at approximately 65 kDa by the anti-VS antibody. However, the rat anti-ALK2 antibodies produced by the hybridomas A2-11E, A2-15A, A2-25C, and A2-27D did not detect any of human, mouse and rat ALK2. On the other hand, the anti-ALK2 monoclonal antibody produced by the hybridoma #109 detected human ALK2 and mouse ALK2 of approximately 65 kDa, but did not detect rat ALK2, demonstrating that this antibody recognizes human ALK2 and mouse ALK2 in a reduced or denatured state.

[Example 7] Immunohistological Staining of Frozen Sections with Rat Anti-Human ALK2 Antibodies (#109, #200, Etc.)

C57BL/6 mouse newborns were each fixed in a 4% paraformaldehyde-phosphate buffer solution for 2 days and then freeze-embedded in O.C.T Compound (manufactured by Sakura Finetek Japan Co., Ltd.), and frozen sections were prepared with a thickness of 5 μm using a cryostat (manufactured by Leica Biosystems Nussloch GmbH, Cat. #CM3050S). The sections were washed with PBS three time and reacted with an endogenous enzyme activity blocking solution (manufactured by Vector Laboratories, Inc., Cat. #SP-6000) for 10 minutes. Then, the sections were washed with PBS-T (0.2% Tween 20-containing PBS) three times, reacted with Blocking One Histo (manufactured by Nacalai Tesque, Inc., Cat. #06349-64) for 5 minutes, and reacted overnight at 4° C. with each of the rat anti-ALK2 antibodies produced by the hybridomas A2-11E, A2-15A, A2-25C, A2-27D, #109, and #200 (10 μg/ml) as a primary antibody. On the following day, the sections were washed with PBS-T three times and reacted with HRP-conjugated anti-rat IgG antibody ImmPRESS Reagent (manufactured by Vector Laboratories, Inc., Cat. #MP-7444) as a secondary antibody for 30 minutes at 37° C. Then, the sections were washed with PBS-T three times, and DAB color development (manufactured by Vector Laboratories, Inc., Cat. #SK-4100) was performed. After washing with distilled water, the sections were counter-stained with hematoxylin, mounted on a glass cover according to a standard method, and observed under BZ-9000 (manufactured by Keyence Corp.).

Figure 5:
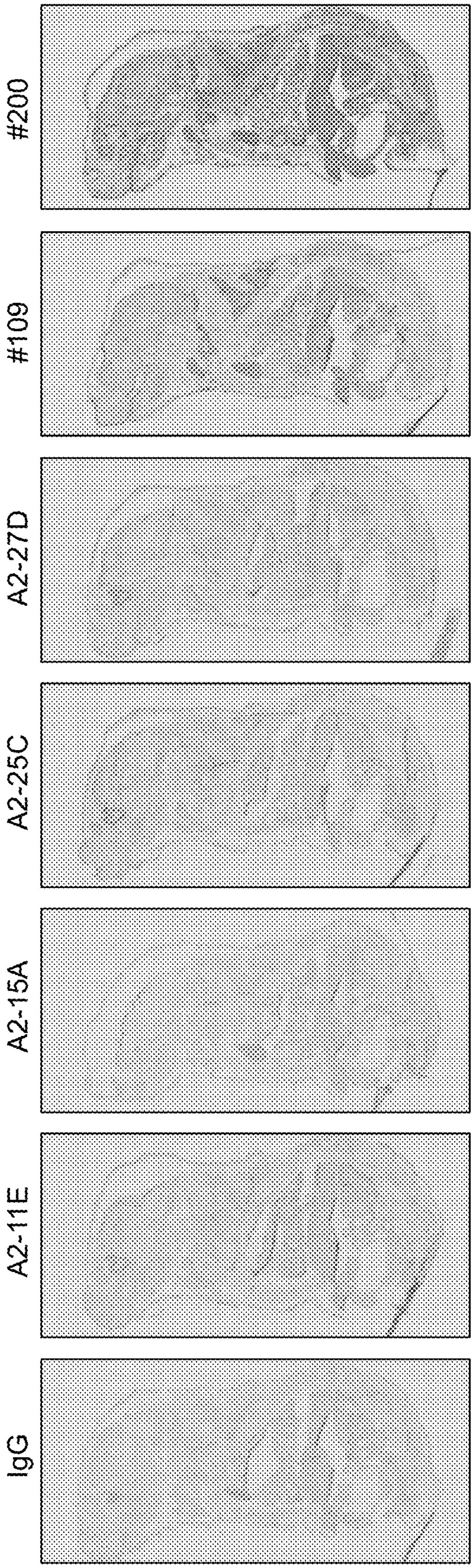
FIG. 5 This figure shows results of immunohistological staining of frozen sections of mouse newborn organs with various rat anti-human ALK2 antibodies. The antibodies are IgG, A2-11E, A2-15A, A2-25C, A2-27D, #109, and #200. The rat anti-ALK2 antibodies produced by the hybridomas A2-11E, A2-15A, A2-25C, and A2-27D were negative in immunostaining to all the mouse newborn organs in the frozen sections, as in control IgG, whereas the antibodies produced by the hybridomas #109 and #200 exhibited an immunostaining positive image for a plurality of mouse newborn organs.

The results are shown in FIG. 5. The rat anti-ALK2 antibodies produced by the hybridomas A2-11E, A2-15A, A2-25C, and A2-27D were negative in immunostaining to all the mouse newborn organs in the frozen sections, as in control IgG. On the other hand, the antibodies produced by the hybridomas #109 and #200 exhibited an immunostaining positive image for a plurality of mouse newborn organs, demonstrating that these antibodies recognize, on frozen sections, ALK2 expressed in mice.

[Example 8] Immunohistological Staining of Paraffin Sections with Rat Anti-Human ALK2 Antibodies (#109, #200, Etc.)

C57BL/6 mouse newborns were each fixed in a 4% paraformaldehyde-phosphate buffer solution for 2 days, then subjected to dehydration and replacement according to standard methods, and embedded in paraffin. Paraffin sections were prepared with a thickness of 4 μm using a rotary microtome (manufactured by Leica Biosystems Nussloch GmbH, Cat. #RM2125RT), and then dried overnight at 37° C. The sections were washed with PBS three time and reacted with an endogenous enzyme activity blocking solution (manufactured by Vector Laboratories, Inc., Cat. #SP-6000) for 10 minutes. Then, the sections were washed with PBS-T (0.2% Tween 20-containing PBS) three times, reacted with Blocking One Histo (manufactured by Nacalai Tesque, Inc., Cat. #06349-64) for 5 minutes, and reacted overnight at 4° C. with each of the rat anti-ALK2 antibodies produced by the hybridomas A2-11E, A2-15A, A2-25C, A2-27D, #109, and #200 (10 μg/ml) as a primary antibody. On the following day, the sections were washed with PBS-T three times and reacted with HRP-conjugated anti-rat IgG antibody ImmPRESS Reagent (manufactured by Vector Laboratories, Inc., Cat. #MP-7444) as a secondary antibody for 30 minutes at 37° C. Then, the sections were washed with PBS-T three times, and DAB color development (manufactured by Vector Laboratories, Inc., Cat. #SK-4100) was performed. After washing with distilled water, the sections were counter-stained with hematoxylin, mounted on a glass cover according to a standard method, and observed under BZ-9000 (manufactured by Keyence Corp.).

Figure 6:
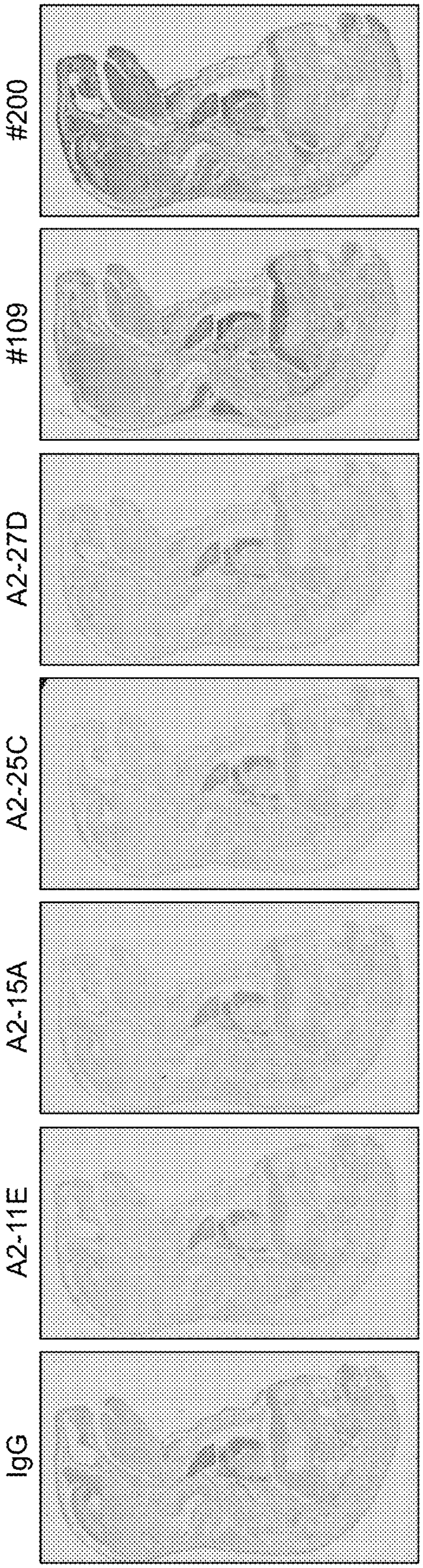
FIG. 6 This figure shows results of immunohistological staining of paraffin sections of mouse newborn organs with various rat anti-human ALK2 antibodies. The antibodies are IgG, A2-11E, A2-15A, A2-25C, A2-27D, #109, and #200. The rat anti-ALK2 antibodies produced by the hybridomas A2-11E, A2-15A, A2-25C, and A2-27D were negative in immunostaining to all the mouse newborn organs in the paraffin sections, as in control IgG, whereas the antibodies produced by the hybridomas #109 and #200 exhibited an immunostaining positive image for a plurality of mouse newborn organs.

The results are shown in FIG. 6. The rat anti-ALK2 antibodies produced by the hybridomas A2-11E, A2-15A, A2-25C, and A2-27D were negative in immunostaining to all the mouse newborn organs in the paraffin sections, as in control IgG. On the other hand, the antibodies produced by the hybridomas #109 and #200 exhibited an immunostaining positive image for a plurality of mouse newborn organs, demonstrating that these antibodies recognize, on paraffin sections, ALK2 expressed in mice.

[Example 9] Formation of ALK2 Homodimer by Rat Anti-Human ALK2 Antibodies (#109, #200, Etc.)

The homodimer formation of human ALK2 by each monoclonal antibody was measured using NanoBIT® Protein:Protein Interaction System (manufactured by Promega Corp.). Human ALK2 cDNA was cloned into each of pBIT1.1-C[TK/LgBIT] vector and pBIT2.1-C[TK/SmBIT] vector. In the same manner as in Example 3, HEK293A cells seeded into a 96-well white plate for luciferase assay (manufactured by Greiner Bio-One International GmbH) on the previous day were transfected with pBIT1.1-C[TK/LgBIT] and pBIT2.1-C[TK/SmBIT] for human ALK2 expression, using Lipofectamine 2000 (Thermo Fisher Scientific Inc.). After 2.5 hours, the medium was replaced with fresh OPTI-MEM I, and the cells were further cultured overnight. On the following day, NanoLuc® luciferase activity induced 14 minutes after addition of 100 ng/ml BMP7 (manufactured by Miltenyi Biotec Inc.) or 10 μg/ml monoclonal antibody using Nano-GLO® Live Cell Assay System (manufactured by Promega Corp.) was measured with plate reader FLUOstar Omega (manufactured by BMG Labtech).

Figure 7:
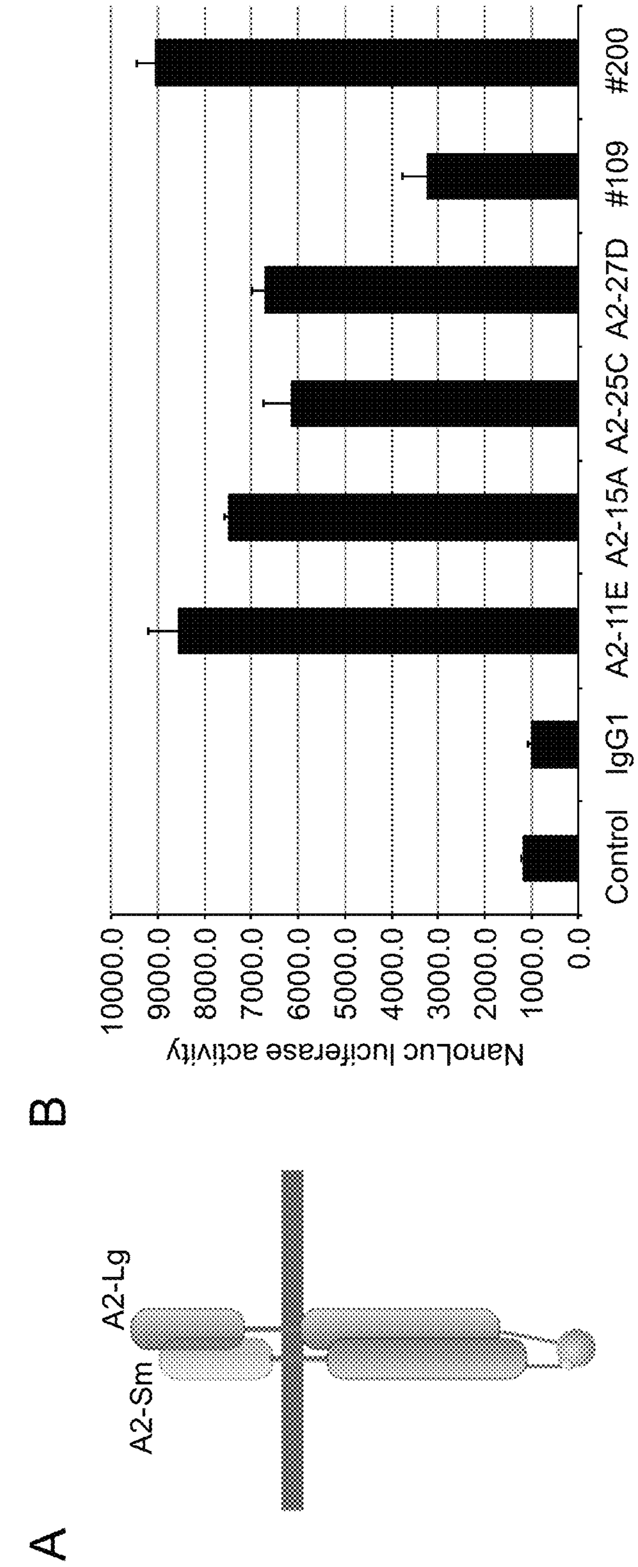
FIG. 7 This figure shows results of examining the formation of an ALK2 homodimer by various rat anti-human ALK2 antibodies. The rat anti-ALK2 antibodies produced by the hybridomas #109, #200, A2-11E, A2-15A, A2-25C, and A2-27D promoted the activity of NanoLuc® luciferase and were therefore found to induce the homodimer formation of human ALK2 (FIGS. 7A and 7B). A control antibody is IgG1. A2-Sm represents a fusion of ALK2 and SmBiT, and A2-Lg represents a fusion of ALK2 and LgBiT.

The results are shown in FIG. 7. The rat anti-ALK2 antibodies produced by the hybridomas #109, #200, and A2-11E, A2-15A, A2-25C, and A2-27D promoted the activity of NanoLuc® luciferase, demonstrating that these antibodies induce the homodimer formation of human ALK2.

[Example 10] Inhibition of ALK2-Type II Receptor Heterodimer Formation by Rat Anti-Human ALK2 Antibodies (#109, #200, Etc.)

The heterodimer formation of human ALK2 and mouse ActR-IIB by each monoclonal antibody was measured using NanoBIT® Protein:Protein Interaction System (manufactured by Promega Corp.). Mouse ActR-IIB cDNA was cloned into pBIT1.1-C[TK/LgBIT] vector, and human ALK2 cDNA was cloned into pBIT2.1-C[TK/SmBIT] vector, respectively. In the same manner as in Example 9, HEK293A cells were transfected with the human ALK2 and mouse ActR-IIB expression vectors, using Lipofectamine 2000 (manufactured by Invitrogen Corp.). After 2.5 hours, the medium was replaced with fresh OPTI-MEM I, and the cells were further cultured overnight. On the following day, the effect of monoclonal antibody on the NanoLuc® luciferase activity induced by 100 ng/ml BMP7 (manufactured by Miltenyi Biotec Inc.) using Nano-GLO® Live Cell Assay System (manufactured by Promega Corp.) was measured with plate reader FLUOstar Omega (manufactured by BMG Labtech).

Figure 8:
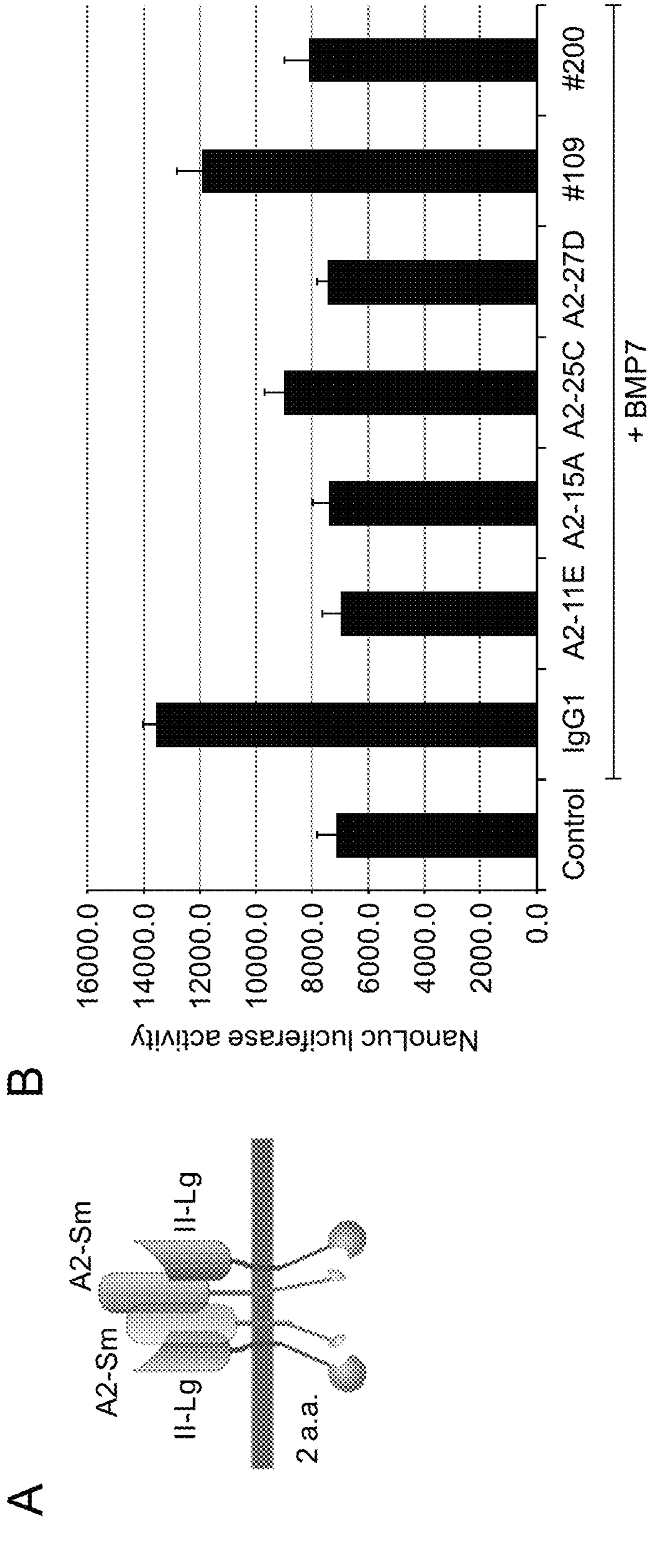
FIG. 8 This figure shows results of examining the inhibition of an ALK2-type II receptor heterodimer formation by various rat anti-human ALK2 antibodies in the presence of BMP7. The rat anti-ALK2 antibodies produced by the hybridomas #200, A2-11E, A2-15A, A2-25C, and A2-27D were found to suppress the heterodimer formation of ALK2 and ActR-IIB receptor induced by BMP7 (FIGS. 8A and 8B). A control antibody is IgG1. A2-Sm represents a fusion of ALK2 and SmBiT, II-Lg represents a fusion of type II receptor and LgBiT, and 2a.a. represents two amino acids.

The results are shown in FIG. 8. The rat anti-ALK2 antibodies produced by the hybridomas #200, and A2-11E, A2-15A, A2-25C, and A2-27D inhibited the NanoLuc® luciferase activity of an ALK2-mouse ActR-IIB heterodimer induced by BMP7. On the other hand, the monoclonal antibody produced by the hybridoma #109 did not inhibit the NanoLuc® luciferase activity. These results demonstrated that the rat anti-ALK2 antibodies produced by the hybridomas #200, and A2-11E, A2-15A, A2-25C, and A2-27D inhibit ALK2-ActR-IIB receptor heterodimer formation induced by BMP7.

INDUSTRIAL APPLICABILITY

The antibody of the present invention can be not only used as a therapeutic drug or a prophylactic drug for BMP-related diseases FOP, DISH, and DIPG but used as a tool of immunological and immunohistological analysis such as immunostaining or Western blot on biological materials such as tissues.

FREE TEXT OF SEQUENCE LISTING

SEQ ID NO: 1: Amino acid sequence of human ALK2 protein
SEQ ID NO: 2: Amino acid sequence of mouse ALK2 protein
SEQ ID NO: 3: Amino acid sequence of rat ALK2 protein
SEQ ID NO: 4: Amino acid sequence of amino acid numbers 1 to 140 of human ALK2
SEQ ID NO: 5: Amino acid sequence of amino acid numbers 1 to 140 of monkey ALK2
SEQ ID NO: 6: Amino acid sequence of amino acid numbers 1 to 140 of dog ALK2
SEQ ID NO: 7: Amino acid sequence of amino acid numbers 1 to 140 of rat ALK2
SEQ ID NO: 8: Amino acid sequence of amino acid numbers 1 to 140 of mouse ALK2
SEQ ID NO: 9: Amino acid sequence of ALK2_#200_VH
SEQ ID NO: 10: cDNA sequence of ALK2_#200_VH
SEQ ID NO: 11: Amino acid sequence of ALL2_#200_VL
SEQ ID NO: 12: cDNA sequence of ALK2_#200_VL
SEQ ID NO: 13: Amino acid sequence of ALK2_#200_VH_CDRH1
SEQ ID NO: 14: Amino acid sequence of ALK2_#200_VH_CDRH2
SEQ ID NO: 15: Amino acid sequence of ALK2_#200_VH_CDRH3
SEQ ID NO: 16: Amino acid sequence of ALK2_#200_VL_CDRL1
SEQ ID NO: 17: Amino acid sequence of ALK2_#200_VL_CDRL2
SEQ ID NO: 18: Amino acid sequence of ALK2_#200_VL_CDRL3
SEQ ID NO: 19: Amino acid sequence of ALK2_#109_VH
SEQ ID NO: 20: cDNA sequence of ALK2_#109_VH
SEQ ID NO: 21: Amino acid sequence of ALK2_#109_VL
SEQ ID NO: 22: cDNA sequence of ALK2_#109_VL
SEQ ID NO: 23: Amino acid sequence of ALK2_#109_VH_CDRH1
SEQ ID NO: 24: Amino acid sequence of ALK2_#109_VH_CDRH2
SEQ ID NO: 25: Amino acid sequence of ALK2_#109_VH_CDRH3
SEQ ID NO: 26: Amino acid sequence of ALK2_#109_VL_CDRL1
SEQ ID NO: 27: Amino acid sequence of ALK2_#109_VL_CDRL2
SEQ ID NO: 28: Amino acid sequence of ALK2_#109_VL_CDRL3
SEQ ID NO: 29: Amino acid sequence of ALK2_A2-15A_VH_CDRH1
SEQ ID NO: 30: Amino acid sequence of ALK2_A2-15A_VH_CDRH2
SEQ ID NO: 31: Amino acid sequence of ALK2_A2-15A_VH_CDRH3
SEQ ID NO: 32: Amino acid sequence of ALK2_A2-15A_VL_CDRL1
SEQ ID NO: 33: Amino acid sequence of ALK2_A2-15A_VL_CDRL2
SEQ ID NO: 34: Amino acid sequence of ALK2_A2-15A_VL_CDRL3
SEQ ID NO: 35: Amino acid sequence of ALK2_A2-27D_VH_CDRH1
SEQ ID NO: 36: Amino acid sequence of ALK2_A2-27D_VH_CDRH2
SEQ ID NO: 37: Amino acid sequence of ALK2_A2-27D_VH_CDRH3
SEQ ID NO: 38: Amino acid sequence of ALK2_A2-27D_VL_CDRL1
SEQ ID NO: 39: Amino acid sequence of ALK2_A2-27D_VL_CDRL2
SEQ ID NO: 40: Amino acid sequence of ALK2_A2-27D_VL_CDRL3
SEQ ID NO: 41: Amino acid sequence of ALK2_A2-11E_VH_CDRH1
SEQ ID NO: 42: Amino acid sequence of ALK2_A2-11E_VH_CDRH2
SEQ ID NO: 43: Amino acid sequence of ALK2_A2-11E_VH_CDRH3
SEQ ID NO: 44: Amino acid sequence of ALK2_A2-11E_VL_CDRL1
SEQ ID NO: 45: Amino acid sequence of ALK2_A2-11E_VL_CDRL2
SEQ ID NO: 46: Amino acid sequence of ALK2_A2-11E_VL_CDRL3
SEQ ID NO: 47: Amino acid sequence of ALK2_A2-25C_VH_CDRH1
SEQ ID NO: 48: Amino acid sequence of ALK2_A2-25C_VH_CDRH2
SEQ ID NO: 49: Amino acid sequence of ALK2_A2-25C_VH_CDRH3
SEQ ID NO: 50: Amino acid sequence of ALK2_A2-25C_VL_CDRL1
SEQ ID NO: 51: Amino acid sequence of ALK2_A2-25C_VL_CDRL2
SEQ ID NO: 52: Amino acid sequence of ALK2_A2-25C_VL_CDRL3
SEQ ID NO: 53: Nucleotide sequence of a primer (Inf-RKRS)
SEQ ID NO: 54: Nucleotide sequence of a primer (Inf-RG2AR3)

SEQ ID NO: 55: Amino acid sequence of altered CDRL2 of A2-15A antibody

SEQ ID NO: 56: Amino acid sequence of humanized hA2-15A-H4 (IgG2)

SEQ ID NO: 57: Amino acid sequence of humanized hA2-15A-L6

SEQ ID NO: 58: Amino acid sequence of humanized hA2-27D-H2-LALA (IgG1)

SEQ ID NO: 59: Amino acid sequence of humanized hA2-27D-L2

SEQ ID NO: 60: Amino acid sequence of humanized hA2-27D-H3-LALA (IgG1)

SEQ ID NO: 61: Amino acid sequence of humanized hA2-27D-L4

All publications, patents and patent applications cited herein are incorporated herein by reference in their entirety.

The invention claimed is:

1. An antibody or an antigen-binding fragment thereof having binding activity to ALK2 protein, where the antibody or the fragment is: an antibody or an antigen-binding fragment thereof in which the heavy chain sequence comprises a variable region comprising CDR sequences consisting of the amino acid sequences of SEQ ID NO: 13 (CDRH1), SEQ ID NO: 14 (CDRH2) and SEQ ID NO: 15 (CDRH3), and the light chain sequence comprises a variable region comprising CDR sequences consisting of the amino acid sequences of SEQ ID NO: 16 (CDRL1), SEQ ID NO: 17 (CDRL2) and SEQ ID NO: 18 (CDRL3).

2. An antibody or an antigen-binding fragment thereof having binding activity to ALK2 protein, where the antibody or the fragment is: an antibody or an antigen-binding fragment thereof in which the heavy chain sequence comprises a variable region comprising CDR sequences consisting of the amino acid sequences of SEQ ID NO: 23 (CDRH1), SEQ ID NO: 24 (CDRH2) and SEQ ID NO: 25 (CDRH3), and the light chain sequence comprises a variable region comprising CDR sequences consisting of the amino acid sequences of SEQ ID NO: 26 (CDRL1), SEQ ID NO: 27 (CDRL2) and SEQ ID NO: 28 (CDRL3).

3. The antibody of claim 1, consisting of a heavy chain comprising a heavy chain variable region sequence consisting of the amino acid sequence of SEQ ID NO: 9 and a light chain comprising a light chain variable region sequence consisting of the amino acid sequence of SEQ ID NO: 11, or an antigen-binding fragment thereof.

4. The antibody of claim 2, consisting of a heavy chain comprising a heavy chain variable region sequence consisting of the amino acid sequence of SEQ ID NO: 19 and a light chain comprising a light chain variable region sequence consisting of the amino acid sequence of SEQ ID NO: 21, or an antigen-binding fragment thereof.

5. A method of immunostaining comprising contacting a s ample with an antibody or antigen-binding fragment thereof according to claim 1.

6. A method of immunostaining comprising contacting a sample with an antibody or antigen-binding fragment thereof according to claim 3.

7. A method of immunostaining or Western blotting comprising contacting a sample with an antibody or antigen-binding fragment thereof according to claim 2.

8. A method of immunostaining or Western blotting comprising contacting a sample with an antibody or antigen-binding fragment thereof according to claim 4.

9. A method of treating ectopic ossification and/or diffuse intrinsic pontine glioma (DIPG), comprising administering to an individual with ectopic ossification and/or DIPG an antibody or antigen-binding fragment thereof according to claim 1.

10. A method of treating ectopic ossification and/or diffuse intrinsic pontine glioma (DIPG), comprising administering to an individual with ectopic ossification and/or DIPG an antibody or antigen-binding fragment thereof according to claim 3.

11. A method of inhibiting phosphorylation of SMAD1, SMAD5, and/or SMAD8, comprising administering to an individual an antibody or antigen-binding fragment thereof according to claim 1.

12. A method of inhibiting phosphorylation of SMAD1, SMAD5, and/or SMAD8, comprising administering to an individual an antibody or antigen-binding fragment thereof according to claim 3.

* * * * *

SEQUENCE LISTING

```
<160> NUMBER OF SEQ ID NOS: 61

<210> SEQ ID NO 1
<211> LENGTH: 509
<212> TYPE: PRT
<213> ORGANISM: Homo sapiens

<400> SEQUENCE: 1

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
```

```
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505


<210> SEQ ID NO 2
<211> LENGTH: 509
<212> TYPE: PRT
<213> ORGANISM: Mus musculus

<400> SEQUENCE: 2

Met Val Asp Gly Val Met Ile Leu Pro Val Leu Met Met Met Ala Phe
1               5                   10                  15

Pro Ser Pro Ser Val Glu Asp Glu Lys Pro Lys Val Asn Gln Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Ile Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175
```

-continued

```
Asp Ser Thr Leu Ala Glu Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Ser Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505


<210> SEQ ID NO 3
<211> LENGTH: 509
<212> TYPE: PRT
<213> ORGANISM: Rattus norvegicus

<400> SEQUENCE: 3

Met Val Asp Gly Ala Met Ile Leu Ser Val Leu Met Met Met Ala Leu
1               5                   10                  15

Pro Ser Pro Ser Met Glu Asp Glu Glu Pro Lys Val Asn Pro Lys Leu
            20                  25                  30

Tyr Met Cys Val Cys Glu Gly Leu Ser Cys Gly Asn Glu Asp His Cys
        35                  40                  45
```

```
Glu Gly Gln Gln Cys Phe Ser Ser Leu Ser Val Asn Asp Gly Phe Arg
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Val Thr Ala Arg Leu Pro Thr Lys Gly Lys
            100                 105                 110

Ser Phe Pro Gly Ser Gln Asn Phe His Leu Glu Val Gly Leu Ile Ile
        115                 120                 125

Leu Ser Val Val Phe Ala Val Cys Leu Phe Ala Cys Ile Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Glu Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Ser Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460
```

```
Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505


<210> SEQ ID NO 4
<211> LENGTH: 140
<212> TYPE: PRT
<213> ORGANISM: Homo sapiens

<400> SEQUENCE: 4

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys
    130                 135                 140


<210> SEQ ID NO 5
<211> LENGTH: 140
<212> TYPE: PRT
<213> ORGANISM: Macca mulatta

<400> SEQUENCE: 5

Met Val Asp Gly Val Met Ile Leu Pro Val Leu Ile Ile Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys
    130                 135                 140
```

```
<210> SEQ ID NO 6
<211> LENGTH: 140
<212> TYPE: PRT
<213> ORGANISM: Canis lupus

<400> SEQUENCE: 6

Met Val Asp Gly Val Met Met Leu Pro Val Leu Met Met Ile Ala Phe
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Glu Thr Gln Asn Phe His Leu Glu Val Gly Leu Ile Ile
        115                 120                 125

Leu Ser Val Val Phe Ala Val Cys Leu Leu Ala Cys
    130                 135                 140


<210> SEQ ID NO 7
<211> LENGTH: 140
<212> TYPE: PRT
<213> ORGANISM: Rattus norvegicus

<400> SEQUENCE: 7

Met Val Asp Gly Ala Met Ile Leu Ser Val Leu Met Met Met Ala Leu
1               5                   10                  15

Pro Ser Pro Ser Met Glu Asp Glu Glu Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Val Asn Asp Gly Phe Arg
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Val Thr Ala Arg Leu Pro Thr Lys Gly Lys
            100                 105                 110

Ser Phe Pro Gly Ser Gln Asn Phe His Leu Glu Val Gly Leu Ile Ile
        115                 120                 125

Leu Ser Val Val Phe Ala Val Cys Leu Phe Ala Cys
    130                 135                 140


<210> SEQ ID NO 8
<211> LENGTH: 140
<212> TYPE: PRT
<213> ORGANISM: Mus musculus

<400> SEQUENCE: 8

Met Val Asp Gly Val Met Ile Leu Pro Val Leu Met Met Met Ala Phe
```

```
1               5                   10                  15

Pro Ser Pro Ser Val Glu Asp Glu Lys Pro Lys Val Asn Gln Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys
    130                 135                 140


<210> SEQ ID NO 9
<211> LENGTH: 119
<212> TYPE: PRT
<213> ORGANISM: Rattus norvegicus

<400> SEQUENCE: 9

Gln Val Lys Leu Leu Gln Ser Gly Ala Ala Leu Val Lys Pro Gly Asp
1               5                   10                  15

Ser Ile Arg Met Ser Cys Lys Ala Ser Gly Tyr Thr Phe Thr Asp Tyr
            20                  25                  30

Ile Ile His Trp Val Lys Gln Ser His Gly Lys Ser Leu Glu Trp Ile
        35                  40                  45

Gly Tyr Ile Asn Pro Tyr Ser Gly Gly Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Glu Phe Cys Arg Leu Thr Ser Glu Asp Ser Ala Ile Tyr Tyr Cys
                85                  90                  95

Val Arg Arg Gly His Asp Gly Thr Gly Phe Asp Tyr Trp Gly Gln Gly
            100                 105                 110

Val Met Val Thr Val Ser Ser
        115


<210> SEQ ID NO 10
<211> LENGTH: 357
<212> TYPE: DNA
<213> ORGANISM: Rattus norvegicus

<400> SEQUENCE: 10

caggtcaagc tgctgcagtc tggggctgca ctggtgaagc ctggggactc tataaggatg      60

tcttgcaaag cttctggtta tacattcact gactacatta tacactgggt gaagcagagt     120

catggaaaga gccttgagtg gattggttat attaatcctt acagtggtgg tactaactac     180

aatgaaaagt tcaagagcaa ggccacattg actgtagaca aatccagcag cacagcctat     240

atggagtttt gcagattgac atctgaggat tctgcaatct attactgtgt aagaagggga     300

catgatggca ccggctttga ttactggggc caaggagtca tggtcacagt ctcctca        357
```

<210> SEQ ID NO 11
<211> LENGTH: 113
<212> TYPE: PRT
<213> ORGANISM: Rattus norvegicus

<400> SEQUENCE: 11

```
Asp Val Val Met Thr Gln Thr Pro Val Ser Leu Pro Val Ser Leu Gly
1               5                   10                  15

Gly Gln Ala Ser Ile Ser Cys Arg Ser Ser Gln Ser Leu Val His Ser
            20                  25                  30

Asn Gly Glu Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Leu
65                  70                  75                  80

Ser Arg Val Glu Pro Glu Asp Leu Gly Asp Tyr Tyr Cys Leu Gln Ser
                85                  90                  95

Thr His Leu Pro Leu Thr Phe Gly Ser Gly Thr Lys Leu Glu Ile Lys
            100                 105                 110

Arg
```

<210> SEQ ID NO 12
<211> LENGTH: 339
<212> TYPE: DNA
<213> ORGANISM: Rattus norvegicus

<400> SEQUENCE: 12

```
gatgttgtga tgacacaaac tccagtctcc ctgcctgtca gccttggagg tcaagcctct     60

atctcttgcc ggtcaagtca gagcctggta cacagtaatg gagaaaccta cttgcattgg    120

tacctgcaga agccaggcca gtctccacag ctcctcatct atcgggtttc caacagattt    180

tctggggtgc cagacaggtt cagtggcagt gggtcaggga cagatttcac cctcaagctc    240

agcagagtag agcctgagga cttgggagat tattactgct tacaaagtac acatttgccg    300

ctcacgttcg gttctgggac caagctggag atcaaacgg                           339
```

<210> SEQ ID NO 13
<211> LENGTH: 10
<212> TYPE: PRT
<213> ORGANISM: Rattus norvegicus

<400> SEQUENCE: 13

```
Gly Tyr Thr Phe Thr Asp Tyr Ile Ile His
1               5                   10
```

<210> SEQ ID NO 14
<211> LENGTH: 10
<212> TYPE: PRT
<213> ORGANISM: Rattus norvegicus

<400> SEQUENCE: 14

```
Tyr Ile Asn Pro Tyr Ser Gly Gly Thr Asn
1               5                   10
```

<210> SEQ ID NO 15
<211> LENGTH: 10
<212> TYPE: PRT
<213> ORGANISM: Rattus norvegicus

<400> SEQUENCE: 15

```
Arg Gly His Asp Gly Thr Gly Phe Asp Tyr
1               5                   10


<210> SEQ ID NO 16
<211> LENGTH: 16
<212> TYPE: PRT
<213> ORGANISM: Rattus norvegicus

<400> SEQUENCE: 16

Arg Ser Ser Gln Ser Leu Val His Ser Asn Gly Glu Thr Tyr Leu His
1               5                   10                  15


<210> SEQ ID NO 17
<211> LENGTH: 7
<212> TYPE: PRT
<213> ORGANISM: Rattus norvegicus

<400> SEQUENCE: 17

Arg Val Ser Asn Arg Phe Ser
1               5


<210> SEQ ID NO 18
<211> LENGTH: 9
<212> TYPE: PRT
<213> ORGANISM: Rattus norvegicus

<400> SEQUENCE: 18

Leu Gln Ser Thr His Leu Pro Leu Thr
1               5


<210> SEQ ID NO 19
<211> LENGTH: 120
<212> TYPE: PRT
<213> ORGANISM: Rattus norvegicus

<400> SEQUENCE: 19

Glu Val Gln Leu Val Glu Ser Gly Gly Asp Leu Val Gln Pro Gly Arg
1               5                   10                  15

Ser Met Lys Leu Ser Cys Ala Ala Ser Gly Phe Thr Phe Ser Asn Tyr
            20                  25                  30

Gly Met Ala Trp Val Arg Gln Ala Pro Thr Lys Gly Leu Glu Trp Val
        35                  40                  45

Ala Thr Ile Ser Tyr Asp Gly Ser Gly Thr Tyr Tyr Arg Asp Ser Val
    50                  55                  60

Glu Gly Arg Phe Thr Ile Ser Arg Asp Asn Ala Lys Ile Thr Leu Tyr
65                  70                  75                  80

Leu Gln Met Asn Ser Leu Arg Ser Glu Asp Thr Ala Thr Tyr Tyr Cys
                85                  90                  95

Thr Arg His Gly Tyr Ser Arg Val Pro Tyr Phe Asp Tyr Trp Gly Gln
            100                 105                 110

Gly Val Met Val Thr Val Ser Ser
        115                 120


<210> SEQ ID NO 20
<211> LENGTH: 360
<212> TYPE: DNA
<213> ORGANISM: Rattus norvegicus

<400> SEQUENCE: 20

gaggtgcagc tggtagagtc tgggggcgat ttagtgcagc ctggaaggtc catgaaactc     60
```

```
tcctgtgcag cctcaggatt cactttcagt aactatggca tggcctgggt ccgccaggct    120

ccaacgaagg gcctggagtg ggttgcaacc attagttatg atggtagtgg cacttactat    180

cgagactccg tggagggccg attcactatc tccagggata atgcaaaaat caccctatac    240

ctgcaaatga acagtctgag gtctgaggac acggccactt attactgtac aagacacggc    300

tatagcagag tcccttactt tgattactgg ggccaaggag tcatggtcac agtctcctca    360


<210> SEQ ID NO 21
<211> LENGTH: 108
<212> TYPE: PRT
<213> ORGANISM: Rattus norvegicus

<400> SEQUENCE: 21

Asn Ile Val Leu Thr Gln Ser Pro Ala Thr Leu Ser Val Thr Pro Gly
1               5                   10                  15

Glu Ser Val Ser Leu Ser Cys Arg Ala Ser Gln Ser Ile Ser Thr Asn
            20                  25                  30

Ile His Trp Tyr Gln Gln Lys Ser Asn Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Arg Val Glu Ser
65                  70                  75                  80

Glu Asp Phe Ser Ile Tyr Tyr Cys Gln Gln Ser Tyr Ser Ser Gln Leu
                85                  90                  95

Thr Phe Gly Ser Gly Thr Lys Leu Glu Ile Lys Arg
            100                 105


<210> SEQ ID NO 22
<211> LENGTH: 324
<212> TYPE: DNA
<213> ORGANISM: Rattus norvegicus

<400> SEQUENCE: 22

aacattgtgt tgactcagtc tccagccacc ctgtctgtga ctccaggaga gagtgtcagt     60

ctctcctgca gggccagtca gagtattagc acaaacatac attggtatca gcaaaaatca    120

aatgagtctc caaggcttct catcaaatat gcttcccagt ccatctctgg aatcccctcc    180

aggttcagtg gcagcggatc cgggacagat ttcactctca ctatcaacag agtagagtct    240

gaagattttt caatttatta ctgtcaacag agttacagca gccagctcac gttcggttct    300

gggaccaagc tggagatcaa acgg                                           324


<210> SEQ ID NO 23
<211> LENGTH: 10
<212> TYPE: PRT
<213> ORGANISM: Rattus norvegicus

<400> SEQUENCE: 23

Gly Phe Thr Phe Ser Asn Tyr Gly Met Ala
1               5                   10


<210> SEQ ID NO 24
<211> LENGTH: 10
<212> TYPE: PRT
<213> ORGANISM: Rattus norvegicus

<400> SEQUENCE: 24

Thr Ile Ser Tyr Asp Gly Ser Gly Thr Tyr
```

1 5 10

<210> SEQ ID NO 25
<211> LENGTH: 10
<212> TYPE: PRT
<213> ORGANISM: Rattus norvegicus

<400> SEQUENCE: 25

His Gly Tyr Ser Arg Val Pro Tyr Phe Asp
1 5 10

<210> SEQ ID NO 26
<211> LENGTH: 11
<212> TYPE: PRT
<213> ORGANISM: Rattus norvegicus

<400> SEQUENCE: 26

Arg Ala Ser Gln Ser Ile Ser Thr Asn Ile His
1 5 10

<210> SEQ ID NO 27
<211> LENGTH: 7
<212> TYPE: PRT
<213> ORGANISM: Rattus norvegicus

<400> SEQUENCE: 27

Tyr Ala Ser Gln Ser Ile Ser
1 5

<210> SEQ ID NO 28
<211> LENGTH: 9
<212> TYPE: PRT
<213> ORGANISM: Rattus norvegicus

<400> SEQUENCE: 28

Gln Gln Ser Tyr Ser Ser Gln Leu Thr
1 5

<210> SEQ ID NO 29
<211> LENGTH: 10
<212> TYPE: PRT
<213> ORGANISM: Rattus norvegicus

<400> SEQUENCE: 29

Gly Phe Thr Phe Ser His Tyr Tyr Met Ala
1 5 10

<210> SEQ ID NO 30
<211> LENGTH: 17
<212> TYPE: PRT
<213> ORGANISM: Rattus norvegicus

<400> SEQUENCE: 30

Ser Ile Thr Asn Ser Gly Gly Ser Ile Asn Tyr Arg Asp Ser Val Lys
1 5 10 15

Gly

<210> SEQ ID NO 31
<211> LENGTH: 14
<212> TYPE: PRT
<213> ORGANISM: Rattus norvegicus

<400> SEQUENCE: 31

Glu Gly Gly Glu Asn Tyr Gly Gly Tyr Pro Pro Phe Ala Tyr 1 5 10

<210> SEQ ID NO 32
<211> LENGTH: 15
<212> TYPE: PRT
<213> ORGANISM: Rattus norvegicus

<400> SEQUENCE: 32

Arg Ala Asn Gln Gly Val Ser Leu Ser Arg Tyr Asn Leu Met His
1 5 10 15

<210> SEQ ID NO 33
<211> LENGTH: 7
<212> TYPE: PRT
<213> ORGANISM: Rattus norvegicus

<400> SEQUENCE: 33

Arg Ser Ser Asn Leu Ala Ser
1 5

<210> SEQ ID NO 34
<211> LENGTH: 9
<212> TYPE: PRT
<213> ORGANISM: Rattus norvegicus

<400> SEQUENCE: 34

Gln Gln Ser Arg Glu Ser Pro Phe Thr
1 5

<210> SEQ ID NO 35
<211> LENGTH: 10
<212> TYPE: PRT
<213> ORGANISM: Rattus norvegicus

<400> SEQUENCE: 35

Gly Ser Thr Phe Ser Asn Tyr Gly Met Lys
1 5 10

<210> SEQ ID NO 36
<211> LENGTH: 17
<212> TYPE: PRT
<213> ORGANISM: Rattus norvegicus

<400> SEQUENCE: 36

Ser Ile Ser Arg Ser Ser Thr Tyr Ile Tyr Tyr Ala Asp Thr Val Lys
1 5 10 15

Gly

<210> SEQ ID NO 37
<211> LENGTH: 12
<212> TYPE: PRT
<213> ORGANISM: Rattus norvegicus

<400> SEQUENCE: 37

Ala Ile Ser Thr Pro Phe Tyr Trp Tyr Phe Asp Phe
1 5 10

<210> SEQ ID NO 38
<211> LENGTH: 10
<212> TYPE: PRT
<213> ORGANISM: Rattus norvegicus

<400> SEQUENCE: 38

Leu Ala Ser Ser Ser Val Ser Tyr Met Thr 1 5 10

<210> SEQ ID NO 39
<211> LENGTH: 7
<212> TYPE: PRT
<213> ORGANISM: Rattus norvegicus

<400> SEQUENCE: 39

Gly Thr Ser Asn Leu Ala Ser
1 5

<210> SEQ ID NO 40
<211> LENGTH: 10
<212> TYPE: PRT
<213> ORGANISM: Rattus norvegicus

<400> SEQUENCE: 40

Leu His Leu Thr Ser Tyr Pro Pro Tyr Thr
1 5 10

<210> SEQ ID NO 41
<211> LENGTH: 10
<212> TYPE: PRT
<213> ORGANISM: Rattus norvegicus

<400> SEQUENCE: 41

Gly Phe Thr Phe Ser Asn Tyr Tyr Met Tyr
1 5 10

<210> SEQ ID NO 42
<211> LENGTH: 17
<212> TYPE: PRT
<213> ORGANISM: Rattus norvegicus

<400> SEQUENCE: 42

Ser Ile Asn Thr Asp Gly Gly Ser Thr Tyr Tyr Pro Asp Ser Val Lys
1 5 10 15

Gly

<210> SEQ ID NO 43
<211> LENGTH: 9
<212> TYPE: PRT
<213> ORGANISM: Rattus norvegicus

<400> SEQUENCE: 43

Ser Thr Pro Asn Ile Pro Leu Ala Tyr
1 5

<210> SEQ ID NO 44
<211> LENGTH: 11
<212> TYPE: PRT
<213> ORGANISM: Rattus norvegicus

<400> SEQUENCE: 44

Lys Ala Ser Gln Asn Ile Tyr Lys Tyr Leu Asn
1 5 10

<210> SEQ ID NO 45
<211> LENGTH: 7
<212> TYPE: PRT
<213> ORGANISM: Rattus norvegicus

<400> SEQUENCE: 45

Tyr Ser Asn Ser Leu Gln Thr 1 5

<210> SEQ ID NO 46
<211> LENGTH: 8
<212> TYPE: PRT
<213> ORGANISM: Rattus norvegicus

<400> SEQUENCE: 46

Phe Gln Tyr Ser Ser Gly Pro Thr
1 5

<210> SEQ ID NO 47
<211> LENGTH: 10
<212> TYPE: PRT
<213> ORGANISM: Rattus norvegicus

<400> SEQUENCE: 47

Gly Phe Thr Phe Ser Tyr Tyr Ala Met Ser
1 5 10

<210> SEQ ID NO 48
<211> LENGTH: 17
<212> TYPE: PRT
<213> ORGANISM: Rattus norvegicus

<400> SEQUENCE: 48

Ser Ile Ser Arg Gly Gly Asp Asn Thr Tyr Tyr Arg Asp Thr Val Lys
1 5 10 15

Gly

<210> SEQ ID NO 49
<211> LENGTH: 9
<212> TYPE: PRT
<213> ORGANISM: Rattus norvegicus

<400> SEQUENCE: 49

Leu Asn Tyr Asn Asn Tyr Phe Asp Tyr
1 5

<210> SEQ ID NO 50
<211> LENGTH: 11
<212> TYPE: PRT
<213> ORGANISM: Rattus norvegicus

<400> SEQUENCE: 50

Gln Ala Ser Gln Asp Ile Gly Asn Trp Leu Ser
1 5 10

<210> SEQ ID NO 51
<211> LENGTH: 7
<212> TYPE: PRT
<213> ORGANISM: Rattus norvegicus

<400> SEQUENCE: 51

Gly Ala Thr Ser Leu Ala Asp
1 5

<210> SEQ ID NO 52
<211> LENGTH: 9
<212> TYPE: PRT
<213> ORGANISM: Rattus norvegicus

<400> SEQUENCE: 52

Leu Gln Ala Tyr Ser Ala Pro Phe Thr

```
1               5


<210> SEQ ID NO 53
<211> LENGTH: 43
<212> TYPE: DNA
<213> ORGANISM: Artificial
<220> FEATURE:
<223> OTHER INFORMATION: primer

<400> SEQUENCE: 53

gattacgcca agctttcagt aacactgtcc aggacaccat ctc                       43


<210> SEQ ID NO 54
<211> LENGTH: 44
<212> TYPE: DNA
<213> ORGANISM: Artificial
<220> FEATURE:
<223> OTHER INFORMATION: primer

<400> SEQUENCE: 54

gattacgcca agcttctcca gagttccagg tcacggtgac tggc                      44


<210> SEQ ID NO 55
<211> LENGTH: 7
<212> TYPE: PRT
<213> ORGANISM: Rattus norvegicus

<400> SEQUENCE: 55

Arg Ser Ser Asn Leu Ala Gln
1               5


<210> SEQ ID NO 56
<211> LENGTH: 468
<212> TYPE: PRT
<213> ORGANISM: Artificial
<220> FEATURE:
<223> OTHER INFORMATION: amino acid sequence of humanized hA2-15A-H4
      (IgG2)

<400> SEQUENCE: 56

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser His Tyr Tyr Met Ala Trp Val Arg Gln Ala Pro Gly Lys Gly Leu
    50                  55                  60

Glu Trp Val Ala Ser Ile Thr Asn Ser Gly Gly Ser Ile Asn Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asn Ser Leu Arg Ala Glu Asp Thr Ala Thr
            100                 105                 110

Tyr Tyr Cys Thr Arg Glu Gly Gly Glu Asn Tyr Gly Gly Tyr Pro Pro
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
```

```
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 57
<211> LENGTH: 238
<212> TYPE: PRT
<213> ORGANISM: Artificial
<220> FEATURE:
<223> OTHER INFORMATION: Amino acid sequence of humanized hA2-15A-L6
<220> FEATURE:
<221> NAME/KEY: SIGNAL
<222> LOCATION: (1)..(20)
<220> FEATURE:
<221> NAME/KEY: V_region
<222> LOCATION: (21)..(133)
<220> FEATURE:
<221> NAME/KEY: C_region
<222> LOCATION: (134)..(238)

<400> SEQUENCE: 57

Met Val Leu Gln Thr Gln Val Phe Ile Ser Leu Leu Leu Trp Ile Ser
```

```
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Asn Cys Arg Ala Asn Gln Gly
        35                  40                  45

Val Ser Leu Ser Arg Tyr Asn Leu Met His Trp Tyr Gln Gln Lys Pro
    50                  55                  60

Gly Gln Lys Pro Lys Leu Leu Ile Tyr Arg Ser Ser Asn Leu Ala Gln
65                  70                  75                  80

Gly Ile Pro Ala Arg Phe Ser Gly Ser Gly Ser Gly Thr Asp Phe Thr
                85                  90                  95

Leu Thr Ile Ser Ser Val Gln Ala Asp Asp Ile Ala Val Tyr Tyr Cys
            100                 105                 110

Gln Gln Ser Arg Glu Ser Pro Phe Thr Phe Gly Gln Gly Thr Lys Leu
        115                 120                 125

Glu Leu Lys Arg Ala Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

```
<210> SEQ ID NO 58
<211> LENGTH: 470
<212> TYPE: PRT
<213> ORGANISM: Artificial
<220> FEATURE:
<223> OTHER INFORMATION: amino acid sequence of humanized hA2-27D-H2-
      LALA (IgG1)

<400> SEQUENCE: 58

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
        35                  40                  45

Ser Asn Tyr Gly Met Lys Trp Ile Arg Gln Ala Pro Gly Lys Gly Leu
    50                  55                  60

Glu Trp Val Ser Ser Ile Ser Arg Ser Ser Thr Tyr Ile Tyr Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Ala Ala Ile Ser Thr Pro Phe Tyr Trp Tyr Phe Asp
        115                 120                 125
```

```
Phe Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

<210> SEQ ID NO 59
<211> LENGTH: 234
<212> TYPE: PRT
<213> ORGANISM: Artificial
<220> FEATURE:
<223> OTHER INFORMATION: Amino acid sequence of humanized hA2-27D-L2
<220> FEATURE:
<221> NAME/KEY: SIGNAL
<222> LOCATION: (1)..(20)
<220> FEATURE:
<221> NAME/KEY: V_region
<222> LOCATION: (21)..(129)

<220> FEATURE:
<221> NAME/KEY: C_region
<222> LOCATION: (130)..(234)

<400> SEQUENCE: 59

```
Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Gly Thr Leu Ser
            20                  25                  30

Leu Ser Pro Gly Glu Arg Ala Thr Leu Ser Cys Leu Ala Ser Ser Ser
        35                  40                  45

Val Ser Tyr Met Thr Trp Tyr Gln Gln Lys Pro Gly Gln Ser Pro Arg
    50                  55                  60

Leu Trp Ile Tyr Gly Thr Ser Asn Leu Ala Ser Gly Val Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Leu His Leu Thr Ser
            100                 105                 110

Tyr Pro Pro Tyr Thr Phe Gly Gln Gly Thr Lys Val Glu Ile Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 60
<211> LENGTH: 470
<212> TYPE: PRT
<213> ORGANISM: Artificial
<220> FEATURE:
<223> OTHER INFORMATION: amino acid sequence of humanized hA2-27D-H3-
LALA (IgG1)

<400> SEQUENCE: 60

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
        35                  40                  45

Ser Asn Tyr Gly Met Lys Trp Ile Arg Gln Ala Pro Gly Lys Gly Leu
    50                  55                  60

Glu Trp Val Ala Ser Ile Ser Arg Ser Ser Thr Ile Tyr Tyr Ala
65                  70                  75                  80

Asp Thr Val Lys Gly Arg Phe Thr Ile Ser Arg Asp Asn Ser Lys Asn
                85                  90                  95
```

```
Thr Leu Tyr Leu Gln Met Asn Ser Leu Arg Ala Glu Asp Thr Ala Val
            100                 105                 110

Tyr Tyr Cys Ala Ala Ala Ile Ser Thr Pro Phe Tyr Trp Tyr Phe Asp
        115                 120                 125

Phe Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

<210> SEQ ID NO 61
<211> LENGTH: 234
<212> TYPE: PRT
<213> ORGANISM: Artificial
<220> FEATURE:

-continued

```
<223> OTHER INFORMATION: Amino acid sequence of humanized hA2-27D-L4
<220> FEATURE:
<221> NAME/KEY: SIGNAL
<222> LOCATION: (1)..(20)
<220> FEATURE:
<221> NAME/KEY: V_region
<222> LOCATION: (21)..(129)
<220> FEATURE:
<221> NAME/KEY: C_region
<222> LOCATION: (130)..(234)

<400> SEQUENCE: 61

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Gly Thr Met Ser
            20                  25                  30

Ala Ser Pro Gly Glu Arg Val Thr Leu Ser Cys Leu Ala Ser Ser Ser
        35                  40                  45

Val Ser Tyr Met Thr Trp Tyr Gln Gln Lys Pro Gly Ala Ser Pro Arg
    50                  55                  60

Leu Trp Ile Tyr Gly Thr Ser Asn Leu Ala Ser Gly Val Pro Asp Arg
65                  70                  75                  80

Phe Ser Gly Ser Gly Ser Gly Thr Asp Tyr Thr Leu Thr Ile Ser Arg
                85                  90                  95

Met Glu Pro Glu Asp Phe Ala Thr Tyr Tyr Cys Leu His Leu Thr Ser
            100                 105                 110

Tyr Pro Pro Tyr Thr Phe Gly Ala Gly Thr Lys Leu Glu Leu Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```